United States Patent
Kim et al.

(10) Patent No.: US 10,751,381 B2
(45) Date of Patent: *Aug. 25, 2020

(54) COMPOSITION FOR PREVENTING, RELIEVING OR TREATING COLITIS, CONTAINING COMPLEX EXTRACTS

(71) Applicant: UNIVERSITY-INDUSTRY COOPERATION GROUP OF KYUNG HEE UNIVERSITY, Gyeonggi-Do (KR)

(72) Inventors: Dong Hyun Kim, Seoul (KR); Myung Joo Han, Seoul (KR)

(73) Assignee: UNIVERSITY-INDUSTRY COOPERATION GROUP OF KYUNG HEE UNIVERSITY, Gyeonggi-Do (KR)

( * ) Notice: Subject to any disclaimer, the term of this patent is extended or adjusted under 35 U.S.C. 154(b) by 77 days.

This patent is subject to a terminal disclaimer.

(21) Appl. No.: 16/216,093

(22) Filed: Dec. 11, 2018

(65) Prior Publication Data

US 2019/0105365 A1 Apr. 11, 2019

Related U.S. Application Data

(63) Continuation of application No. 14/786,754, filed as application No. PCT/KR2014/001252 on Feb. 17, 2014, now Pat. No. 10,195,244.

(30) Foreign Application Priority Data

Apr. 23, 2013 (KR) .................. 10-2013-0044990

(51) Int. Cl.
| | |
|---|---|
| *A61K 36/8964* | (2006.01) |
| *A23L 2/02* | (2006.01) |
| *A23L 2/52* | (2006.01) |
| *A23L 7/10* | (2016.01) |
| *A23L 33/105* | (2016.01) |
| *A23L 13/40* | (2016.01) |
| *A23L 23/00* | (2016.01) |
| *A61K 36/718* | (2006.01) |
| *A61K 31/7048* | (2006.01) |

(52) U.S. Cl.
CPC ............ *A61K 36/8964* (2013.01); *A23L 2/02* (2013.01); *A23L 2/52* (2013.01); *A23L 7/10* (2016.08); *A23L 13/428* (2016.08); *A23L 23/00* (2016.08); *A23L 33/105* (2016.08); *A61K 31/7048* (2013.01); *A61K 36/718* (2013.01); *A23V 2002/00* (2013.01)

(58) Field of Classification Search
None
See application file for complete search history.

(56) References Cited

U.S. PATENT DOCUMENTS 10,195,244 B2 *  2/2019  Kim .................. A23L 33/105
2002/0025348 A1  2/2002  Basu et al.

FOREIGN PATENT DOCUMENTS

| CN | 1113791 A | 12/1995 |
|---|---|---|
| KR | 10-2001-0085669 A | 9/2001 |
| KR | 10-0778078 B1 | 11/2007 |
| KR | 10-0856335 B1 | 9/2008 |
| KR | 10-2009-0029022 A | 3/2009 |
| KR | 10-0923953 B1 | 10/2009 |
| KR | 10-0970739 B1 | 7/2010 |
| KR | 10-1075742 B1 | 10/2011 |
| KR | 10-2013-0022733 A | 3/2013 |

OTHER PUBLICATIONS

Jang, et al. "Anticolitic effect of the rhizome mixture of *Anemarrhena asphodeloides* and *Coptidis chinensis* (AC-mix) in mice.", *Biomol. Ther.*, (Sep. 30, 2013) 21(5):398-404.
Leiro, et al. "Expression profiles of genes involved in the mouse nuclear factor-kappa B signal transduction pathway are modulated by mangiferin.", *International Immunopharmacology*, (2004) 4:763-778.
Li, et al. "Berberine attenuates proinflammatory Cytokineinduced tight junction disruption in an in vitro model of intestinal epithelial cells.", *European Journal of Pharmaceutical Sciences*, (2010) 40:1-8.
Miura, et al. "Antidiabetic activity of a xanthone compound, mangiferin." *Phytomedicine*, (2001) 8(2):85-87.
Morais, et al. "Mangiferin, a natural xanthone, accelerates gastrointestinal transit in mice involving cholinergic mechanism." *World J. Gastroenterol.*, (Jul. 7, 2012) 18(25):3207-3214.
Shin, et al. "Mangiferin isolated from the rhizome of Anemarrhena asphodeloides inhibits the LPS-induced nitric oxide and prostagladin E2 via the NF-κB inactivation in inflammatory macrophages." *Natural Product Sciences*, (2008) 14(3):206-213.
Tjong, et al. "Analgesic effect of *Coptis chinensis* rhizomes (Coptidis Rhizoma) extract on rat model of irritable bowel syndrome." *Journal of Ethnopharmacology*, (2011) 135:754-761.
Zhou, et al. "The effect of berberine chloride on experimental colitis in rats in vivo and in vitro." *The Journal of Pharmacology and Experimental Therapeutics* (JPET), (2000) 294(3):822-829.

(Continued)

*Primary Examiner* — Susan Hoffman
(74) *Attorney, Agent, or Firm* — Harness, Dickey & Pierce, P.L.C.

(57) ABSTRACT

The present invention relates to a novel use of an *Anemarrhena asphodeloides* Bunge extract, and the like, and a *Rhizoma Coptidis* extract, and the like, and specifically, provides a composition for preventing, relieving, or treating colitis, including, as active ingredients: one or more selected from the *Anemarrhena asphodeloides* Bunge extract, a C3 to C8-alcohol-soluble fraction of the *Anemarrhena asphodeloides* Bunge extract, mangiferin, a pharmaceutically acceptable salt of mangiferin, neomangiferin, or a pharmaceutically acceptable salt of neomangiferin; and one or more selected from a *Rhizoma Coptidis* extract and a C3 to C8-alcohol-soluble fraction of the *Rhizoma Coptidis* extract.

18 Claims, 28 Drawing Sheets

(56) References Cited

OTHER PUBLICATIONS

International Search Report (ISR) dated May 22, 2013 in PCT/KR2014/001252, with English translation.
Office Action (Non-Final) from corresponding U.S. Appl. No. 14/786,754, dated Dec. 18, 2017.

* cited by examiner

Mangiferin     $R_1$=Glc $R_2$= H
Neomangiferin     $R_1$=Glc $R_2$= Glc

COMPOSITION FOR PREVENTING, RELIEVING OR TREATING COLITIS, CONTAINING COMPLEX EXTRACTS

CROSS-REFERENCE TO RELATED APPLICATIONS

This application is a continuation application of U.S. application Ser. No. 14/786,754, filed on 23 Oct. 2015, now U.S. Pat. No. 10,195,244, which is a national phase application of PCT Application No. PCT/KR2014/001252, filed on 17 Feb. 2014, which claims benefit of Korean Patent Application KR 10-2013-0044990, filed on 23 Apr. 2013. The entire disclosure of the application identified in this paragraph is incorporated herein by reference.

TECHNICAL FIELD

The present invention relates to novel uses of an *Anemarrhena asphodeloides* Bunge extract, and the like, and a *Rhizoma Coptidis* extract, and the like, and more specifically, to a composition for preventing, improving, or treating colitis including an *Anemarrhena asphodeloides* Bunge extract, and the like, and a *Rhizoma Coptidis* extract, and the like.

BACKGROUND

Colitis is a disease which involves an inflammation of colon. Colitis occurs due to various reasons, and major symptoms include tenesmus, abdominal distension, lower abdominal pain, diarrhea, and the like, and in some cases may accompany symptoms that include mucus, pus, or bloody excreta. Colitis may largely be divided into infectious colitis and non-infectious colitis depending on the cause, and may be divided into acute colitis and chronic colitis according to the onset period. Acute colitis includes amoebic dysentery, shigellosis, pseudomembranous enteritis due to Salmonellas or antibiotic materials, and the like, and chronic colitis includes ulcerative colitis, and those due to Crohn's disease, tuberculosis, syphilis, X-ray, and the like. Additionally, colitis not only includes inflammatory bowel disease (IBD) but also irritable bowel syndrome (IBS), and the like. Causes of the ulcerative colitis (UC) and Crohn's disease (CD), which are the representative diseases among the inflammatory bowel diseases (IBD), have not been identified, and they may cause severe chronic diarrhea and bloody diarrhea along with abdominal pain, may not be completely cured, and are characterized in that improvement and aggravation of symptoms are repeated. Ulcerative colitis is a disease that causes a continuous formation of erosion (inflammation) or ulcer on the mucous membrane of colon, and causes bloody feces, mucous and bloody feces, diarrhea, and abdominal pain, and in severe cases, it cause systemic symptoms such as fever, weight loss, anemia, and the like. Additionally, ulcerative colitis can occur in any region of the gastrointestinal tract. Crohn's disease is a disease where lesions such as ulcer occur non-consecutively on any areas of the digestive tract spanning from the mouth to the anus, and accompanies abdominal pain, diarrhea, and bloody excreta, and in severe cases, accompanies symptoms such as fever, melena, weight loss, systemic boredom, anemia, and the like. Although ulcerative colitis and Crohn's disease exhibit difference in the lesions and the inflammatory symptoms, they exhibit similar features in various aspects and thus the two diseases are often difficult to distinguish from each other.

Conventionally, the incidence rate of ulcerative colitis and Crohn's disease have been known to be high in western people, however, patients of these diseases are also rapidly increasing in oriental hemisphere including Korea due to the recent change in daily customs including dietary habits. However, the fundamental therapies have not yet been established because there are also reasons where the reasons are not clear. In this regard, the current therapy is focused on using drugs to alleviate symptoms and maintain the alleviated state as long as possible, instead of aiming at perfect cure. As drugs for the public remedies, amino salicylic acid formulation, adrenal corticosteroids formulations, immune suppressive drugs, immunosuppressive agents are mainly used but they are reportedly have various side effects. For example, salazosulfapyridine, which is frequently used as an amino salicylic acid formulation, has been reported to have side effects such as nausea, vomiting, anorexia, rash, headache, liver injury, leukopenia, abnormality of red blood cells, proteinuria, diarrhea, and the like. Additionally, adrenal corticosteroids formulations are generally used for oral administration of prednisolone, enema, suppositories, intravenous injection, and the like, but they have severe side effects such as ulcer or osteonecrosis of femoral head due to a long-term use. However, cessation of administration causes relapse of symptoms, and thus administration of these drugs cannot be stopped but should be continued. Accordingly, there is a need for the development of a therapeutic agent for treating colitis such as ulcerative colitis, Crohn's disease, and the like, with excellent effects and safety without side effects. Similarly, an irritable bowel syndrome (IBS) is a chronic celiopathy, the cause of which is still not clear. Until now, a fundamental treatment for the IBS has not been developed, and only a symptomatic treatment is being performed to alleviate the symptoms of each of the IBS types. For example, an anticholinergic drug having a spasmolytic function that suppresses the contraction of a smooth muscle is used for the treatment of a diarrhea IBS, saline cathartics are used for a constipation IBS, and a drug for enhancing the movement of alimentary tract is basically used for the treatment of alternative IBS because it is difficult to control the alternative IBS using a drug.

Meanwhile, *Anemarrhena asphodeloides* Bunge is a perennial monocotyledon plant belonging to the Family *Anemarrhena asphodeloides* Bunge of the Order *Liliales*, and the root stock of the *Anemarrhena asphodeloides* Bunge dried with the skin thereon or the rhizome thereof is used as a drug. It has been reported that the rhizome of the *Anemarrhena asphodeloides* Bunge is used as a fever reducer in the field of oriental drug, and has an effect on chronic bronchitis or diabetes. Regarding the pharmaceutical use of the *Anemarrhena asphodeloides* Bunge, Korean Patent No. 10-0856335 discloses that the compound isolated from the *Anemarrhena asphodeloides* Bunge has an effect on preventing and treating respiratory diseases; Korean Patent No. 10-0923953 discloses that an *Anemarrhena asphodeloides* Bunge extract has an effect on alleviating the damage of choline nervous system; and Korean Patent No. 10-1075742 discloses that the compound isolated from the *Anemarrhena asphodeloides* Bunge has an effect on preventing and treating lipid metabolic diseases. Additionally, *Coptis* is an evergreen perennial dicotyledon plant belonging to the Family Ranunculaceae of the Order Ranunculales, and specific examples include *Coptis teeta, Coptis japonica, Coptis chinensis, Coptis deltoidea, Coptis omeiensis*, and the like. In oriental drug, Rhizoma Coptidis which is the rhizome of *Coptis* dried in the sunlight is used as a drug. Berberine, coptisine, worenine, palmatine, and the like, have been known as drug ingredients, and they have been reported to have the effects of antibacteria, anti-inflammation, fever-reduction, promoting bile acid secretion, lowering blood pressure, and the like. Regarding the pharmaceutical use of the *Coptis*, Korean Patent Application Publication No. 10-2001-0085669 discloses a pharmaceutical composition for preventing and treating drug addiction including a *Coptis* extract as an active ingredient; Korean Patent Application Publication No. 10-2009-0029022 discloses a composition for preventing and treating skin diseases due to UV rays including a *Coptis* extract as an active ingredient; Korean Patent Application Publication No. 10-2013-0022733 discloses a composition for treating pancreatic cancer including a *Coptis chinensis* extract; Korean Patent No. 10-0970739 discloses a composition for preventing and treating respiratory diseases including a *Coptis* extract as an active ingredient; and additionally, there have been disclosed a composition for treating periodontal diseases including a *Coptis* extract, a composition for preventing and treating diabetic complications including a *Coptis* extract, a composition for protecting and regenerating neurons including a *Coptis* extract, and the like.

SUMMARY

Technical Problem

The present invention was contrived under the conventional technological background, and an object of the present invention is to provide novel uses of an *Anemarrhena asphodeloides* Bunge extract, and the like, and a Rhizoma Coptidis extract, and the like, and more specifically, to provide uses of a combined extract including an *Anemarrhena asphodeloides* Bunge extract, and the like, and a Rhizoma Coptidis extract, and the like, regarding preventing, improving, or treating colitis.

Technical Solution

The present inventors performed research to develop an extract having the effects of preventing or treating colitis using numerous natural substances that have secured safety compared with synthetic chemical substances. As a result, the inventors found that a combined extract consisting of an *Anemarrhena asphodeloides* Bunge extract, and the like, and a Rhizoma Coptidis extract, and the like, has excellent effects of preventing or treating colitis in a colitis-induced animal model, and thereby completed the present invention.

In order to achieve the above objects, the present invention provides a pharmaceutical composition for preventing or treating colitis, including as active ingredients one or more selected from an *Anemarrhena asphodeloides* Bunge extract, a C3 to C8-alcohol-soluble fraction of the *Anemarrhena asphodeloides* Bunge extract, mangiferin, a pharmaceutically acceptable salt of mangiferin, neomangiferin, and a pharmaceutically acceptable salt of neomangiferin; and one or more selected from a Rhizoma Coptidis extract and a C3 to C8-alcohol-soluble fraction of the Rhizoma Coptidis extract. In this case, the composition for preventing, improving, or treating colitis preferably is in the form of a pharmaceutical composition or food composition.

Additionally, the weight ratio between one or more selected from an *Anemarrhena asphodeloides* Bunge extract, a C3 to C8-alcohol-soluble fraction of the *Anemarrhena asphodeloides* Bunge extract, mangiferin, a pharmaceutically acceptable salt of mangiferin, neomangiferin, and a pharmaceutically acceptable salt of neomangiferin; and one or more selected from a Rhizoma Coptidis extract and a C3 to C8-alcohol-soluble fraction of the Rhizoma Coptidis extract may be in the range of from 10:1 to 1:10, preferably from 1:1 to 5:1, more preferably from 1:1 to 4:1, and most preferably from 2:1 to 4:1. For example, the active ingredients of the composition for preventing, improving, or treating colitis may be composed of a combination of an *Anemarrhena asphodeloides* Bunge extract and a Rhizoma Coptidis extract, and in this case, the weight ratio between the *Anemarrhena asphodeloides* Bunge extract and the Rhizoma Coptidis extract is preferably in the range of from 1:1 to 5:1, more preferably from 1:1 to 4:1, and most preferably from 2:1 to 4:1. Additionally, the active ingredients of the composition for preventing, improving, or treating colitis may be composed of a combination of a C3 to C8-alcohol-soluble fraction of the *Anemarrhena asphodeloides* Bunge extract and a C3 to C8-alcohol-soluble fraction of the Rhizoma Coptidis extract, and the weight ratio between the alcohol-soluble fraction of the *Anemarrhena asphodeloides* Bunge extract and the alcohol-soluble fraction of the Rhizoma Coptidis extract is in the range of from 1:1 to 5:1, more preferably from 1:1 to 4:1, and most preferably from 2:1 to 4:1.

Additionally, the extraction solvent for the *Anemarrhena asphodeloides* Bunge extract may be water, an alcohol having a carbon number of 1 to 2, or a mixed solvent thereof. Additionally, the alcohol-soluble fraction of the *Anemarrhena asphodeloides* Bunge extract is obtained by suspending the *Anemarrhena asphodeloides* Bunge extract by adding water thereto followed by fractionation after adding an alcohol having a carbon number of 3 to 8 thereto, and more preferably a butanol-soluble fraction of the *Anemarrhena asphodeloides* Bunge extract. The *Anemarrhena asphodeloides* Bunge extract or the alcohol-soluble fraction of the *Anemarrhena asphodeloides* Bunge extract may include mangiferin or neomangiferin as an active ingredient.

Additionally, the source material of the Rhizoma Coptidis extract is preferably *Coptis chinensis*. Additionally, the extraction solvent for the Rhizoma Coptidis extract may be water, an alcohol having a carbon number of 1 to 2, or a mixed solvent thereof. Additionally, the alcohol-soluble fraction of the Rhizoma Coptidis extract is obtained by suspending the Rhizoma Coptidis extract by adding water thereto followed by fractionation after adding an alcohol having a carbon number of 3 to 8 thereto, and more preferably a butanol-soluble fraction of the Rhizoma Coptidis extract. Preferably, the Rhizoma Coptidis extract or the alcohol-soluble fraction of the Rhizoma Coptidis extract may include berberine as an active ingredient.

Additionally, the specific kinds of colitis which may be treated, improved, or prevented by applying the composition of the present invention may not be largely limited to acute colitis, chronic colitis, or the like, and may be an inflammatory bowel disease or an irritable bowel syndrome.

Advantageous Effects

The combined extract comprising the *Anemarrhena asphodeloides* Bunge extract, and the like, and the Rhizoma Coptidis extract, and the like, according to the present invention, have excellent effects of preventing or treating colitis in colitis-induced animal models, and thus can be used as food and pharmaceutical materials constituting a pharmaceutical composition or a functional food composition. The pharmaceutical composition or the functional food composition can be used for effectively preventing, delaying, improving, or treating acute colitis or chronic colitis, in this case, an inflammatory bowel disease (IBD) or an irritable bowel syndrome (IBS).

Meanwhile, various conventional herb drugs extracted or fractionated from medicinal crops have been reported not to have better effects than Mesalazine®, a representative colitis treatment. Accordingly, the fact that the combined use of an *Anemarrhena asphodeloides* Bunge extract, and the like and a Rhizoma Coptidis extract, and the like have a higher anti-colitis effect than Mesalazine® is due to the synergistic effect and the synergistic effect can be hardly anticipated.

DETAILED DESCRIPTION

Figure 1:
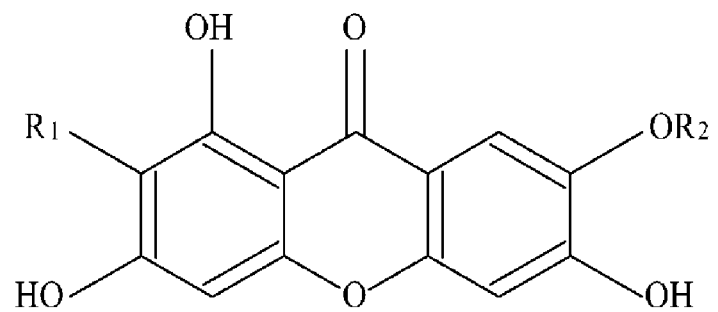
FIG. 1 illustrates chemical structures for mangiferin and neomangiferin.

Hereinafter, the terms used in the present invention will be described.

As used herein, the terms "pharmaceutically acceptable" and "sitologically acceptable" refer to neither significantly stimulating a biological organism nor inhibiting of a biological activity and characteristics of an active material to be administered.

As used herein, the term "prevention" refers to all activities that can suppress the symptoms of a specific disease (for example, colitis) or delay the progression of the specific disease by administering the composition of the present invention.

As used herein, the term "improvement" refers to all activities that can at least reduce parameters related to the state being treated, for example, the degree of symptoms.

As used herein, the term "treatment" refers to all activities that can improve or beneficially change the symptoms of a specific disease (for example, colitis) by administering the composition of the present invention.

As used herein, the term "administration" refers to the supply of the predetermined composition of the present invention to a subject in any appropriate method. In this case, the subject refers to all kinds of animals including such as humans, monkeys, dogs, goats, pigs, and rats having a particular disease, the symptoms of which can be improved by administering the composition of the present invention.

As used herein, the term "a pharmaceutically effective amount" refers to an amount sufficient for the treatment of a disease at a reasonable benefit/risk ratio applicable to a medical treatment without causing any adverse effects, and the level of the effective dose may be determined based on the factors including the kind of a subject, severity of illness, drug activity, drug sensitivity, administration time, administration route and dissolution rate, length of treatment, drug(s) used concurrently, and other factors well known in the medical field.

Hereinafter, the present invention will be described in detail.

The present invention provides a composition for preventing or treating colitis including a combined extract consisting of extracts of at least two herb drugs as an active ingredient. The combined extract includes a pharmaceutical composition for preventing or treating colitis, including as active ingredients one or more (hereinafter, "a first active ingredient") selected from an *Anemarrhena asphodeloides* Bunge extract, a C3 to C8-alcohol-soluble fraction of the *Anemarrhena asphodeloides* Bunge extract (hereinafter, "an alcohol-soluble fraction of the *Anemarrhena asphodeloides* Bunge extract"), mangiferin, a pharmaceutically (or sitologically) acceptable salt of mangiferin, neomangiferin, and a pharmaceutically (or sitologically) acceptable salt of neomangiferin; and one or more (hereinafter, "a second active ingredient") selected from a Rhizoma Coptidis extract and a C3 to C8-alcohol-soluble fraction of the Rhizoma Coptidis extract (hereinafter, "an alcohol-soluble fraction of the Rhizoma Coptidis extract"). In this case, the mixing ratio between the first active ingredient and the second active ingredient, which constitute the combined extract, is not much limited. For example, the weight ratio between the first active ingredient and the second active ingredient may be in the range of from 10:1 to 1:10, preferably from 1:1 to 5:1 in consideration of the effects of preventing, improving, or treating colitis, more preferably from 1:1 to 4:1, and most preferably from 2:1 to 4:1. Additionally, the combined extract for preventing, improving, or treating colitis as an active ingredient according to the present invention may be selected from various combinations. For example, the composition of the present invention for preventing, improving, or treating colitis may include an *Anemarrhena asphodeloides* Bunge extract and a Rhizoma Coptidis extract as active ingredients. Additionally, the composition of the present invention for preventing, improving, or treating colitis may include an *Anemarrhena asphodeloides* Bunge extract and an alcohol-soluble fraction of the Rhizoma Coptidis extract as active ingredients. Additionally, the composition of the present invention for preventing, improving, or treating colitis may include an alcohol-soluble fraction of the *Anemarrhena asphodeloides* Bunge extract and a Rhizoma Coptidis extract as active ingredients. Additionally, the composition of the present invention for preventing, improving, or treating colitis may include an alcohol-soluble fraction of the *Anemarrhena asphodeloides* Bunge extract and an alcohol-soluble fraction of the Rhizoma Coptidis extract as active ingredients. Additionally, the composition of the present invention for preventing, improving, or treating colitis may include mangiferin and a Rhizoma Coptidis extract as active ingredients. Additionally, the composition of the present invention for preventing, improving, or treating colitis may include mangiferin and an alcohol-soluble fraction of the Rhizoma Coptidis extract as active ingredients. Additionally, the composition of the present invention for preventing, improving, or treating colitis may include neomangiferin and a Rhizoma Coptidis extract as active ingredients. Additionally, the composition of the present invention for preventing, improving, or treating colitis may include neomangiferin and an alcohol-soluble fraction of the Rhizoma Coptidis extract as active ingredients. Among them, considering the economical aspect according to the commercialization and the effects of preventing, improving, or treating colitis, the active ingredients of the composition for preventing, improving, or treating colitis may preferably be comprised of a combination between the *Anemarrhena asphodeloides* Bunge extract and the Rhizoma Coptidis extract, or between the alcohol-soluble fraction of the *Anemarrhena asphodeloides* Bunge extract and the alcohol-soluble fraction of the Rhizoma Coptidis extract. When the active ingredients of the composition for preventing, improving, or treating colitis of the present invention are comprised of the combination between the *Anemarrhena asphodeloides* Bunge extract and the Rhizoma Coptidis extract, the weight ratio between the *Anemarrhena asphodeloides* Bunge extract and the Rhizoma Coptidis extract is preferably in the range of from 1:1 to 5:1, more preferably from 1:1 to 4:1, and most preferably from 2:1 to 4:1, considering the effects of preventing, improving, or treating colitis. Additionally, when the active ingredients of the composition for preventing, improving, or treating colitis of the present invention are comprised of the alcohol-soluble fraction of the *Anemarrhena asphodeloides* Bunge extract and the alcohol-soluble fraction of the Rhizoma Coptidis extract, the weight ratio between the alcohol-soluble fraction of the *Anemarrhena asphodeloides* Bunge extract and the alcohol-soluble fraction of the Rhizoma Coptidis extract is preferably in the range of from 1:1 to 5:1, more preferably from 1:1 to 4:1, and most preferably from 2:1 to 4:1, considering the effects of preventing, improving, or treating colitis.

Additionally, in the present invention, *Coptis* which is the source of the Rhizoma Coptidis is not much limited in its kind as long as it belongs to the genus *Coptis*, and may be selected from *Coptis teeta, Coptis japonica, Coptis chinensis, Coptis deltoidea, Coptis omeiensis*, and the like, and among them, *Coptis chinensis* is preferable, considering the amount of active ingredients included in root stock and their constituting ratio relating to their effects of preventing, improving, or treating colitis.

Additionally, the colitis in the present invention refers to the condition having the inflammation of colon caused by bacterial infection or pathologic fermentation of intestinal contents, and it is a concept including infectious colitis and non-infectious colitis. A specific kind of colitis that can be prevented or treated by the combined extract of the present invention includes an acute colitis and a chronic colitis, but the present invention is not limited thereto, and more specifically, includes an inflammatory bowel disease, an irritable bowel syndrome, and the like. Examples of the inflammatory bowel disease include ulcerative colitis, Crohn's disease, and the like. The acute colitis refers to an inflammation in colon or large intestine, which mainly illustrates symptoms such as mucus diarrhea and fresh blood symptom because of the damage in the mucous membrane caused by inflammation. In the present invention, the acute colitis includes acute pseudomembranous colitis and acute ulcerative colitis as well as general acute infectious colitis. The combined extract according to the present invention can improve the external appearance of the colon and inhibit the contraction of colon in an animal model with acute colitis induced by 2,4,6-trinitrobenzenesulfonic acid (TNBS), an animal model with acute colitis induced by dextran sulfate sodium (DSS), an animal model with chronic colitis induced by oxazolone, and an animal model with chronic colitis induced by dextran sulfate sodium (DSS), and can also maintain myeloperoxidase (MPO) activity at low level thereby capable of preventing, improving, or treating colitis.

The combined extract as an active ingredient of the composition for preventing, improving, or treating colitis according to the present invention may be prepared in various methods. For example, the combined extract may be prepared by mixing an *Anemarrhena asphodeloides* Bunge and Rhizoma Coptidis, adding an extraction solvent thereto, and then extracting a mixed extract; or by adding an alcohol having a carbon number of 3 to 8 to the mixed extract. Additionally, the combined extract may be prepared by obtaining an *Anemarrhena asphodeloides* Bunge extract and a Rhizoma Coptidis extract, respectively, and then mixing them; or by obtaining an alcohol-soluble fraction of the *Anemarrhena asphodeloides* Bunge extract and an alcohol-soluble fraction of the Rhizoma Coptidis extract and then mixing them. Specifically, the *Anemarrhena asphodeloides* Bunge extract and the Rhizoma Coptidis extract, which constitute the combined extract, may be prepared using a conventional extraction method known in the art, for example, a solvent extraction method. The extraction solvent to be used for the solvent extraction method may be selected from the group consisting of water, low alcohol having 1 to 4 carbon atoms (for example, methanol, ethanol, propanol, and butanol), or a mixture thereof, i.e., water-containing low alcohol, propyleneglycol, 1,3-butyleneglycol, glycerin, acetone, diethylether, ethyl acetate, butyl acetate, dichloromethane, chloroform, hexane, and a mixture thereof, and among them, preferably, may be selected from water, alcohol, and water-containing alcohol, which is a mixture thereof, and more preferably, from water-containing alcohol. When water is used as an extraction solvent, the water is preferably hot water. Additionally, when alcohol is used as an extraction solvent, the alcohol is preferably low alcohol having 1 to 4 carbon atoms, and more preferably, the low alcohol is selected from methanol or ethanol. Additionally, when water-containing alcohol is used as an extraction solvent, the alcohol content is preferably 50% to 90%, and more preferably 60% to 85%. Meanwhile, it is obvious for one of ordinary skill in the art that the *Anemarrhena asphodeloides* Bunge extract or the Rhizoma Coptidis extract exhibiting substantially the same effect may be obtained even when extraction solvents other than the above-described extraction solvents are used. Additionally, the *Anemarrhena asphodeloides* Bunge extract and the Rhizoma Coptidis extract, which constitute the combined extract, may include extracts obtained through other conventional extraction methods or the extracts obtained through a purification and fermentation process, as well as the extracts obtained by the above-described extraction solvents. For example, the extract according to the present invention may include the active fractions obtained through various purification and extraction methods that are additionally performed, for example, a supercritical fluid extraction using carbon dioxide, an ultrasonic extraction, an isolation method using an ultra-filtration membrane having a certain molecular weight cutoff value, various chromatography (which are manufactured for the isolation according to size, charge, hydrophobicity, or affinity), an extraction using fermented products by various microorganisms, and the like. Generally, the supercritical fluid has the properties of a liquid and a gas, which are obtained when a gas reaches the critical point under the conditions of high temperature and high pressure, and has chemically similar polarity to a non-polar solvent. Due to the property, the supercritical fluid is used for the extraction of fat-soluble substances (J. Chromatogr. A. 1998; 479: 200 to 205). Carbon dioxide, while going through with the process of making a pressure and temperature to reach the critical point by operating a supercritical fluid instrument, becomes a supercritical fluid concurrently having both liquid and gas properties, which is realized by being subjected to the process of making a pressure and temperature to be the critical point by the operation of supercritical fluid instrument, and as a result, possesses increased solubility in a fat-soluble solute. When the supercritical carbon dioxide passes through an extraction container including a sample in a predetermined amount, the fat-soluble substance included in the sample is extracted in the supercritical carbon dioxide. After extracting the fat-soluble substance, the components that were not extracted with pure supercritical carbon dioxide alone may be extracted by flowing the supercritical carbon dioxide including a small amount of co-solvent onto the sample remaining in the extraction container. The supercritical fluid used in the supercritical extraction method of the present invention may effectively extract an active component using supercritical carbon dioxide or a mixed fluid prepared by further mixing a co-solvent with carbon dioxide. Such a co-solvent may be a mixture of one or two or more types selected from the group consisting of chloroform, ethanol, methanol, water, ethyl acetate, hexane, and diethyl ether. The extracted sample mostly includes carbon dioxide, which is volatilized into the air at room temperature, and the co-solvent may be removed with a rotary vacuum evaporator. Additionally, the ultrasonic extraction method is a method using energy generated by ultrasonic vibrations. The ultrasonic waves may destroy an insoluble solvent included in the sample in an aqueous solvent, and in this case, the high local temperature generated thereof increases the kinetic energy of reactant particles located around, thereby obtaining sufficient energy for the reaction. Furthermore, a high pressure is induced by the shock effect of ultrasonic energy, which increases the mixing effect of the solvent and the substance included in the sample, thereby increasing the extraction efficiency. The extraction solvent that can be used in the ultrasonic extraction method may be a mixture of one or two or more types selected from the group consisting of chloroform, ethanol, methanol, water, ethyl acetate, hexane, and diethyl ether. An extract may be obtained from the extracted sample by a general method for preparing an extract, which includes collecting a filtrate after vacuum-filtration of the extracted sample, removing the filtrate with a rotary vacuum evaporator, and then, subjecting the filtrate to a freeze-drying. Additionally, the *Anemarrhena asphodeloides* Bunge extract and the Rhizoma Coptidis extract, which constitute the combined extract, includes an extract that has gone through with a fermentation process, for example, the fermentation extract of the *Anemarrhena asphodeloides* Bunge may be prepared as follows. *Anemarrhena asphodeloides* Bunge is finely pulverized to about from 100 to about 500 mesh, a conventional culture medium for a microorganism is added thereto until the *Anemarrhena asphodeloides* Bunge concentration becomes 1 g/L to 50 g/L, and a microorganism such as, a yeast strain or Lactobacillus is added thereto in the amount of 10,000 cfu/L to 100,000 cfu/L. Then, the resultant is then cultured in a typical microorganism culture conditions, i.e., at 30° C. to 37° C. and pH 5 to pH 7 under an aerobic or anaerobic condition for about from 5 days to 10 days. Finally, the fermentation extract of the *Anemarrhena asphodeloides* Bunge can be obtained through an aging and filtration. The fermentation extract of the Rhizoma Coptidis may be prepared by the same process.

Additionally, the alcohol-soluble fractions of the *Anemarrhena asphodeloides* Bunge extract and the Rhizoma Coptidis extract, which constitute the combined extract, can be obtained from the *Anemarrhena asphodeloides* Bunge extract and the Rhizoma Coptidis extract, respectively. In this case, the alcohol used for obtaining the soluble fractions has 3 to 8 carbon atoms, and considering the solubility of the active substances of the *Anemarrhena asphodeloides* Bunge extract and the Rhizoma Coptidis extract and the concentration process under reduced pressure after the solubilization of the active substances thereof, the alcohol may have preferably 3 to 6 carbon atoms, more preferably 3 to 5 carbon atoms, and most preferably 4 carbon atoms. Examples of the alcohol having 4 carbon atoms to be used in the present invention for the solubilization of the *Anemarrhena asphodeloides* Bunge extract or the solubilization of the Rhizoma Coptidis extract may include n-butanol, sec-butanol, isobutanol, tert-butanol, and the like. The alcohol-soluble fraction of the *Anemarrhena asphodeloides* Bunge extract or the alcohol-soluble fraction of the Rhizoma Coptidis extract, which constitute the combined extract consist of ingredients that can be soluble in an alcohol having 3 to 8 carbon atoms among the ingredients included in the *Anemarrhena asphodeloides* Bunge extract or the Rhizoma Coptidis extract, and in this case, it is preferable that the *Anemarrhena asphodeloides* Bunge extract or the Rhizoma Coptidis extract is extracted with water, an alcohol having 1 to 2 carbon atoms, or a mixed solvent thereof. The alcohol-soluble fraction of the *Anemarrhena asphodeloides* Bunge extract or the alcohol-soluble fraction of the Rhizoma Coptidis extract may be obtained, for example, by a method including obtaining the *Anemarrhena asphodeloides* Bunge extract or the Rhizoma Coptidis extract using the alcohol having 1 to 2 carbon atoms or water-containing alcohol, which is a mixture thereof, as an extraction solvent, suspending the extract by adding water thereto, and adding an alcohol having 3 to 8 carbon atoms (for example, butanol) followed by fractionation.

Additionally, the *Anemarrhena asphodeloides* Bunge extract or an alcohol-soluble fraction thereof preferably includes mangiferin or neomangiferin as an active ingredient. In the present invention, mangiferin or neomangiferin may be an ingredient constituting the combined extract instead of the *Anemarrhena asphodeloides* Bunge extract or the alcohol-soluble fraction of the *Anemarrhena asphodeloides* Bunge extract. Additionally, the Rhizoma Coptidis extract or an alcohol-soluble fraction thereof preferably includes berberine as an active ingredient. Furthermore, the Rhizoma Coptidis extract or an alcohol-soluble fraction thereof may additionally include Palmatine, Coptisine, Columbamine, Jatrorrhizine, and the like, as an active substance. However, for the active substances included in the *Anemarrhena asphodeloides* Bunge extract or the alcohol-soluble fraction thereof and the *Coptis* extract or the alcohol-soluble fraction thereof, the types or contents of the specific ingredients may vary slightly according to the extraction method or fractionation method.

Additionally, mangiferin or neomangiferin, which constitute the combined extract, may be isolated from a plant such as *Anemarrhena asphodeloides* Bunge. FIG. 1 illustrates a chemical structure of mangiferin and neomangiferin. As illustrated in FIG. 1, mangiferin has the same aglycon as neomangiferin, and aglycon has been known to control the physiological activity in glycoside compounds. Accordingly, it should be obvious for one of ordinary skill in the art to predict the anti-colitis activity of neomangiferin based on the anti-colitis activity of mangiferin.

For a pharmaceutically- or sitologically acceptable salt to be used in the present invention, acid added salts formed by a free acid may be useful. Acid added salts may be prepared by a conventional method, for example, by dissolving a compound in excess aqueous acid solution followed by precipitating the salt using a water-miscible organic solvent such as methanol, ethanol, acetone, or acetonitrile. An equimolar amount of an acid or alcohol (for example, glycol monomethyl ether) of a compound and water may be heated and then dried by evaporation, or the precipitated salt may be subjected to suction filtration. In this case, the free acid may be an organic or inorganic acid, and examples of the inorganic acid may include hydrochloric acid, phosphoric acid, sulfuric acid, nitric acid, tartaric acid, and the like, and examples of the organic acid may include methanesulfonic acid, p-toluenesulfonic acid, acetic acid, trifluoroacetic acid, citric acid, maleic acid, succinic acid, oxalic acid, benzoic acid, tartaric acid, fumaric acid, mandelic acid, propionic acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid, and the like. Additionally, a pharmaceutically or sitologically acceptable metal salt may be prepared using a base. An alkali metal- or alkali earth metal salt may be prepared, for example, by dissolving a compound in an excess of an alkali metal hydroxide or alkali earth metal hydroxide solution, filtrating non-dissolved compound salt, and then evaporating the filtrate followed by drying. In this case, for the metal salt, sodium-, potassium-, or calcium salt are suitable, and also, the corresponding silver salt may be prepared by reacting with an alkali metal- or alkali earth metal salt with an appropriate silver salt (for example, silver nitrate).

The composition for preventing, improving, or treating colitis including the combined extract according to the present invention may be specified into a pharmaceutical composition, a food additive, a food composition (especially, a nutraceutical composition), or a feed additive according to purposes and features of use. The content of the combined extract within the composition may be adjusted in various ranges according to the specific shape, purpose of use, or feature of use of the composition.

In the pharmaceutical composition for preventing or treating colitis, the content of the combined extract as active ingredient within the composition is not particularly limited, and may be in the range of 0.1 wt % to 99 wt %, preferably 0.5 wt % to 50 wt %, and more preferably 1 to 30 wt % relative to the total weight of the composition. Additionally, the pharmaceutical composition of the present invention may further include additives, such as a pharmaceutically acceptable carrier, excipient, or diluent in addition to the extract-based active ingredient. The carrier, excipient, and diluents that may be included in the pharmaceutical composition of the present invention may be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oils. Additionally, the composition for preventing or treating colitis according to the present invention may further include one or more types of known active ingredients having the effects of preventing or treating colitis, in addition to the combined extract. The pharmaceutical composition of the present invention may be prepared into formulations for oral administration or parenteral administration according to a conventional method. In preparing the formulations, additives such as a diluent such as a filler, an extender, a binder, a humectant, a disintegrant, a surfactant, and the like, and an excipient may be used. A solid formulation for an oral administration may include tablets, pills, powders, granules, capsules, and the like, and such the solid formulation may be prepared by mixing the combined extract as active ingredient with at least one or more excipient, for example, starch, calcium carbonate, sucrose, lactose, or gelatin. Additionally, a lubricant, such as magnesium stearate and talc may be used, in addition to the simple excipient. A liquid formulation for oral administration may be a suspension, a liquid formulation for internal use, an emulsion, syrups, and the like, and various excipients, for example, a humectant, a sweetening agent, a flavoring agent, a preserving agent may be used in addition to the commonly-used simple diluents such as water and liquid paraffin. A formulation for parenteral administration may include a sterile aqueous solution, a non-aqueous solvent, a suspension, an emulsion, a freeze-dried formulation, and a suppository. As a non-aqueous solvent and a suspension solvent, propylene glycol, polyethylene glycol, a vegetable oil such as olive oil, an injectable ester such as ethyl oleate, and the like, may be used. As a base compound of a suppository, Witepsol, Macrogol, Tween 61, Cacao butter, Laurin butter, glycerol gelatin, and the like, may be used. Furthermore, the formulation may be preferably prepared according to each disease or ingredient using a proper method in the art or the method disclosed in Remington's Pharmaceutical Science (Latest issue), Mack Publishing Company, Easton PA. The pharmaceutical composition of the present invention may be orally or parenterally administered to a mammal including humans according to the desired method. Examples of parenteral administration may include an external use of skin, intraperitoneal injection, intrarectal injection, subcutaneous injection, intravenous injection, intramuscular injection, or intrathoracic injection. The dosage of the pharmaceutical composition of the present invention is not particularly limited but may vary according to the weight, age, sex, health condition, and diet of a patient, administration time, administration method, excretion rate, and severity of disease(s). A conventional daily dosage of the pharmaceutical composition of the present invention is not particularly limited, but may be preferably administered, for example, 0.1 mg/kg to 1000 mg/kg, and more preferably 1 mg/kg to 500 mg/kg based on the combined extract as active ingredient, and may be administered once daily or a few divided doses a day.

Additionally, the content of the combined extract of the food composition of the present invention for preventing or improving colitis is not particularly limited but may be in the range of from 0.01 wt % to 50 wt %, preferably from 0.1 wt % to 25 wt %, and more preferably from 0.5 wt % to 10 wt %. The food composition of the present invention may be prepared in the form of pills, powders, granules, infusions, tablets, capsules, liquid, and the like, and specific examples of the food may include meats, sausages, breads, chocolates, candies, snacks, confectionaries, pizzas, ramens, other noodles, gums, dairy products including ice creams, various kinds of soups, beverages, teas, functional water, drinks, alcoholic beverages, vitamin complexes, and the like, and may include all the health foods from the conventional point of view. The food composition of the present invention may further include various flavoring agents or natural carbohydrates as an additional ingredient, in addition to the combined extract as active ingredient. Additionally, the food composition of the present invention may include various nutritional supplements, vitamins, electrolytes, flavoring agents, coloring agents, pectic acid and a salt thereof, alginic acid and a salt thereof, an organic acid, a protective colloidal thickener, a pH controlling agent, a stabilizer, a preservative, glycerin, alcohol, a carbonating agent used for carbonated drinks, and the like. Additionally, the food composition of the present invention may include the flesh for preparing natural fruit juices, fruit juice drinks, and vegetable drinks. These ingredients may be used independently or in combination of the same. The above-described natural carbohydrates may include monosaccharides such as glucose and fructose, disaccharides such as maltose and sucrose, and polysaccharides such as dextrin and cyclodextrin, and sugar alcohols such as xylitol, sorbitol, and erythritol. As a flavoring agent, natural flavoring agents such as thaumatin and a stevia extract, or synthesized flavoring agents such as saccharin and aspartame may be used.

Hereinafter, the present invention will be described in more detail with reference to Examples. However, the following Examples are only for illustrating the technical properties of the present invention, but are not limited to the claimed range of the present invention.

EXAMPLES

I. Primary Experiment for Confirmation of the Effects of an *Anemarrhena asphodeloides* Bunge Extract, and the Like, and a Rhizoma Coptidis Extract, and the Like, and a Combined Use Thereof for Preventing or Treating Colitis 1. Preparation of an *Anemarrhena asphodeloides* Bunge Extract, a Fraction Thereof, and Compounds Isolated Therefrom.

Preparation Example 1: Preparation of an *Anemarrhena asphodeloides* Bunge Extract.

After adding 2 L of an 80% aqueous methanol solution to 500 g of *Anemarrhena asphodeloides* Bunge, the mixture was subjected to an extraction process in a water bath for about 2 hours, and then filtered. Additionally, the remaining residue was subjected to a re-extraction under the same condition after adding 1 L of the same solvent thereto and filtered. The filtered liquid extract was concentrated under reduced pressure and freeze-dried to obtain 189 g of an *Anemarrhena asphodeloides* Bunge extract.

Preparation Example 2: Preparation of a Butanol-Soluble Fraction from an *Anemarrhena asphodeloides* Bunge Extract.

After suspending 189 g of the *Anemarrhena asphodeloides* Bunge extract obtained in Preparation Example 1 in 1.5 L of water, 1.5 L of n-butanol was added thereto, and the resultant was placed in a shaking bath to separate an n-butanol-soluble fraction layer and a water-soluble fraction layer therefrom. The n-butanol-soluble fraction layer was collected, concentrated under reduced pressure, and freeze-dried to obtain 41 g of the n-butanol-soluble fraction. The yield of the n-butanol-soluble fraction was 8.2% or higher based on the *Anemarrhena asphodeloides* Bunge, and the content of mangiferin included in the n-butanol-soluble fraction was 10% or higher.

Preparation Example 3: Isolation of Compounds from a Butanol-Soluble Fraction of an *Anemarrhena asphodeloides* Bunge Extract.

Figure 2:
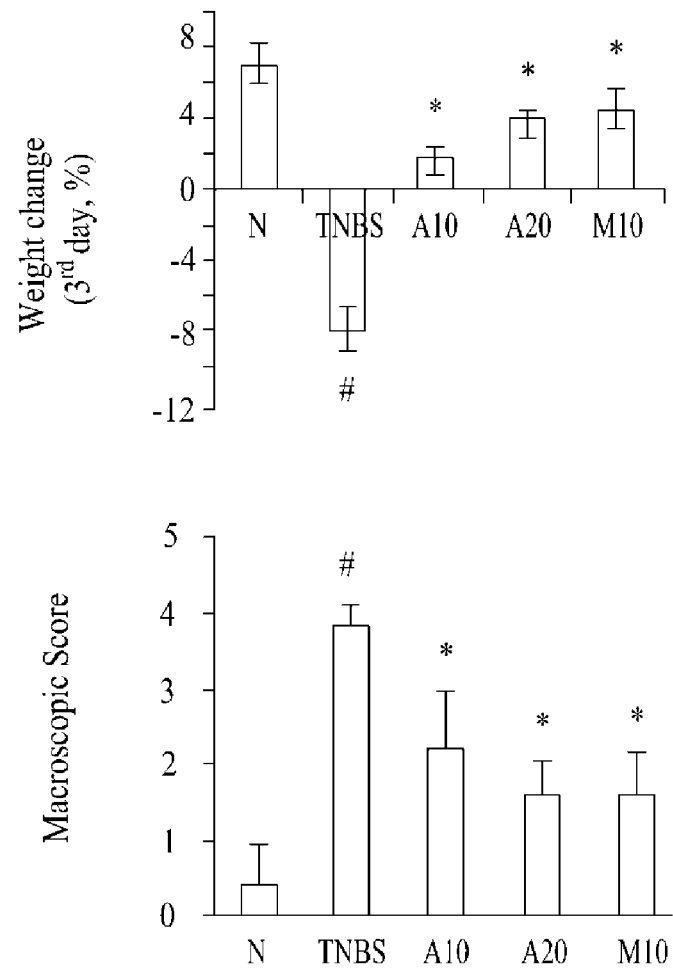
FIG. 2 illustrates graphs respectively illustrating the weight change and the score on external appearance of colon in model animals induced with acute colitis by TNBS when the n-butanol-soluble fraction of the *Anemarrhena asphodeloides* Bunge extract obtained in Preparation Example 2 was used as a drug sample.

10 g of the n-butanol-soluble fraction obtained in Preparation Example 2 was subjected to a silica gel column chromatography (Merck, 10 cm×30 cm, 70 to 230 mesh) using an elution solvent (chloroform:methanol:water=65:35:10) to obtain nine sub-fractions. Among the nine sub-fractions, Fr. VII, which was a sub-fraction having the best effect in the animal model experiment on colitis was subjected to a medium pressure liquid chromatography (MPLC, $C_{18}$ reverse Merck, 3 cm×20 cm) using 25% methanol as an elution solvent to obtain two fractions. The two fractions were concentrated, respectively, and re-crystallized with methanol, respectively, to obtain two compounds in the form of white powder. As a result of examining the structures of the two compounds by mass analysis and $^{13}$C-NMR (Bruker, AVANCE digital 400), it was confirmed that the two compounds were mangiferin and neomangiferin, respectively. FIG. 2 illustrates chemical structures for mangiferin and neomangiferin. The yields of mangiferin and neomangiferin were 0.5% or higher and 0.1% or higher, respectively, based on the *Anemarrhena asphodeloides* Bunge.

<Mangiferin>

ESI(-)-MS/MS 421, 301 [M-Na]$^-$ $^{13}$C NMR (100 MHz) peaks: 162.254 (C-1), 108.04 (C-2), 164.295 (C-3), 93.813 (C-4), 103.088 (C-5), 154.606 (C-6), 144.228 (C-7), 108.489 (C-8), 179.551 (C-9), 156.697 (C-4a), 151.286 (C-4b), 112.128 (C-8a), 101.772 (C-8b), 82.025 (2-glc C-1'), 73.564 (C-2'), 71.103 (C-3'), 70.724 (C-4'), 79.449 (C-5'), 61.961 (C-6').

<Neomangiferin>

ESI(-)-MS/MS 421, 301 [M-Na]$^-$ $^{13}$C NMR (100 MHz) peaks: 162.5 (C-1), 108.3 (C-2), 164. 5 (C-3), 94.0 (C-4), 103.3 (C-5), 156.9 (C-6), 144.4 (C-7), 112.4 (C-8), 179.8 (C-9), 154.7(C-4a), 151.5 (C-4b), 108.8 (C-8a), 102.0 (C-8b), 73.8 (2-glc C-1'), 71.3 (C-2'), 79.7 (C-3'), 71.0 (C-4'), 82.2, (C-5'), 61.4 (C-6'), 103.4 (7-glc C-1") 73.5 (C-2"), 76.1 (C-3"), 69.6 (C-4"), 77.3 (C-5"), 60.7 (C-6").

2. Preparation of a *Galla Rhois* Extract, a Fraction Thereof, and Compounds Isolated Therefrom.

Preparation Example 4: Preparation of a *Galla Rhois* Extract.

After adding 2 L of an 80% aqueous methanol solution to 500 g of a *Galla Rhois* extract, the mixture was subjected to an extraction process in a water bath for about 2 hours, and then filtered. Additionally, the remaining residue was subjected to a re-extraction under the same condition after adding 1 L of the same solvent thereto and filtered. The filtered liquid extract was concentrated under reduced pressure and freeze-dried to obtain 190 g of a *Galla Rhois* extract.

Preparation Example 5: Preparation of a Butanol-Soluble Fraction from a *Galla Rhois* Extract.

After suspending 190 g of the *Galla Rhois* extract obtained in Preparation Example 4 in 1.5 L of water, 1.5 L of n-butanol was added thereto, and the resultant was placed in a shaking bath to separate an n-butanol-soluble fraction layer and a water-soluble fraction layer therefrom. The n-butanol-soluble fraction layer was collected, concentrated under reduced pressure, and freeze-dried to obtain 102 g of the n-butanol-soluble fraction. The yield of the n-butanol-soluble fraction was 21% or higher based on the *Galla Rhois*, and the content of glucose1,2,3,4,6-penta-O-galloyl-β-D-glucose included in the n-butanol-soluble fraction was 30% or higher.

3. Preparation of a *Codonopsis lanceolate* Extract, a Fraction Thereof, and Compounds Isolated Therefrom.

Preparation Example 6: Preparation of *Codonopsis lanceolate* Extract.

After adding 4 L of an 80% aqueous methanol solution to 2 kg of dried *Codonopsis lanceolate* Trautv root (Kyoung Dong Market, Seoul, Korea), the mixture was subjected to an extraction process in a water bath for about 2 hours, and then filtered. Additionally, the remaining residue was subjected to a re-extraction under the same condition after adding 2 L of the same solvent there to and filtered. The filtered liquid extract was concentrated under reduced pressure and freeze-dried to obtain 185 g of a *Codonopsis lanceolate* extract.

Preparation Example 7: Preparation of a Butanol-Soluble Fraction from a *Codonopsis lanceolate* Extract.

After suspending 185 g of the *Codonopsis lanceolate* extract obtained in Preparation Example 6 in 1.5 L of water, 1.5 L of n-butanol was added thereto, and the resultant was placed in a shaking bath to separate an n-butanol-soluble fraction layer and a water-soluble fraction layer therefrom. The n-butanol-soluble fraction layer was collected, concentrated under reduced pressure, and freeze-dried to obtain 112 g of the n-butanol-soluble fraction. The yield of the n-butanol-soluble fraction was 5.5% or higher based on the *Codonopsis lanceolate*, and the content of Lancemaside A included in the n-butanol-soluble fraction was 4% or higher.

4. Preparation of a *Coptis chinensis* extract and a Fraction Thereof.

Preparation Example 8: Preparation of a *Coptis chinensis* Extract.

After adding 2 L of an 80% aqueous methanol solution to 500 g of dried root of *Coptis chinensis* (Kyoung Dong Market, Seoul, Korea), the mixture was subjected to an extraction process in a water bath for about 2 hours, and then filtered. Additionally, the remaining residue was subjected to a re-extraction under the same condition after adding 1 L of the same solvent there to and filtered. The filtered liquid extract was concentrated under reduced pressure and freeze-dried to obtain 123 g of a *Coptis chinensis* extract.

Preparation Example 9: Preparation of a Butanol-Soluble Fraction from a *Coptis chinensis* extract.

After suspending 123 g of the *Coptis chinensis* extract obtained in Preparation Example 8 in 1.5 L of water, 1.5 L of n-butanol was added thereto, and the thus-obtained solution was placed in a shaking bath to separate an n-butanol-soluble fraction layer and a water-soluble fraction layer therefrom. The n-butanol-soluble fraction layer was collected, concentrated under reduced pressure, and freeze-dried to obtain 63 g of the n-butanol-soluble fraction. The yield of the n-butanol-soluble fraction was 12.5% or higher based on the *Coptis chinensis*. The ingredients included in the n-butanol-soluble fraction were analyzed using a high-performance liquid chromatography (HPLC; Waters Alliance 2695 model). As a column, YMC hydrosphere C18 (S-5 μm, 120 nm, 4.6 mm×250 mm ID) was used, and the sample was maintained at 25° C.±1° C. and the column was maintained at 30° C.±1° C. The sample was prepared at a concentration of 1 mg/mL and 10 μL of the sample was injected, and analyzed at a flow rate of 1.0 mL/min. Additionally, as a standard substance, commercial products of berberine, palmatine, coptisine, and the like, were purchased from Sigma for use. Columbamine and jatrorrhizine were isolated and purified from *Coptis* for use. The analysis was performed using a 0.2% phosphate solution (solvent A) and methanol (solvent B) as a mobile phase under a gradient condition, for 0 minute to 60 minutes (A:B=9:1 to 6:4), 60 minutes to 70 minutes (A:B=6:4 to 5:5), and 70 minutes to 90 minutes (A:B=5:5 to 0:10). For the calculation of the content of active ingredients, the ratio of an area ratio to each of standard substances was represented as a weight percentage. As a result of the analysis, the n-butanol-soluble fraction of *Coptis chinensis* extract includes about 27 wt % to 30 wt % of berberine, about 7 wt % to 8 wt % of palmatine, about 5 wt % to 6 wt % of coptisine, about 0.8 wt % to 1.2 wt % of columbamine, and about 0.8 wt % to 1.2 wt % of jatrorrhizine.

5. Preparation of a Combined Extract.

Preparation Example 10.

50 parts by weight of the butanol-soluble fraction of the *Anemarrhena asphodeloides* Bunge extract obtained in Preparation Example 2 and 50 parts by weight of the butanol-soluble fraction of the *Galla Rhois* extract obtained in Preparation Example 5 were mixed to prepare a combined extract.

Preparation Example 11.

50 parts by weight of the butanol-soluble fraction of the *Anemarrhena asphodeloides* Bunge extract obtained in Preparation Example 2 and 50 parts by weight of the butanol-soluble fraction of the *Codonopsis lanceolata* extract obtained in Preparation Example 7 were mixed to prepare a combined extract.

Preparation Example 12.

50 parts by weight of the butanol-soluble fraction of the *Anemarrhena asphodeloides* Bunge extract obtained in Preparation Example 2, 50 parts by weight of the butanol-soluble fraction of the *Galla Rhois* extract obtained in Preparation Example 5, and 50 parts by weight of the butanol-soluble fraction of the *Codonopsis lanceolata* extract obtained in Preparation Example 7 were mixed to prepare a combined extract.

Preparation Example 13.

50 parts by weight of the butanol-soluble fraction of the *Anemarrhena asphodeloides* Bunge extract obtained in Preparation Example 2 and 50 parts by weight of the butanol-soluble fraction of the *Coptis chinensis* extract obtained in Preparation Example 9 were mixed to prepare a combined extract.

6. Measurement of Effects of Treating Colitis in Experiments of Model Animals with Acute Colitis Induced by TNBS.

(1) Preparation of Experimental Animals.

6-week old male mice (C57BL/6, 18 g to 22 g) were purchased from OrientBio Inc. All the mice were bred under the controlled environmental conditions of 50±10% of humidity at a temperature of 20° C. to 22° C., and the lighting was provided by repeatedly turning on for 12 hours followed by turning off for 12 hours. A feed for a standard experiment (Samyang, Korea) was used as a feed, and ad libitum access to water was allowed. In all experiments, each group consisted of 6 mice.

(2) Induction of Acute Colitis by TNBS and Sample Administration.

Among the experimental groups, one group was set as a normal group, and the experimental animals in other groups were induced with acute colitis by 2,4,6-trinitrobenzenesulfonic acid (TNBS). In detail, after lightly anesthetizing the experimental animals with ether, 0.1 mL of the solution prepared by mixing 2.5 g of 2,4,6-Trinitrobenzene sulfonic acid (NBS) solution with 50% ethanol was injected into the colon through the anus using a syringe having 1 mL volume and an oval point, respectively; the syringe was vertically picked up, and then, maintained for 30 seconds to induce inflammation. Meanwhile, for the normal group, 0.1 mL of normal saline solution was orally administered. Subsequently, from the following day, the sample dissolved in normal saline solution was orally administered at a predetermined volume once daily for 3 days. On the following day after completing the sample administration, the experimental animals were suffocated to death with carbon dioxide, and the colon from the appendix to the region immediately before the anus was removed from the colon region. In this case, as a drug sample, the experiments using the butanol-soluble fraction of the *Anemarrhena asphodeloides* Bunge extract, mangiferin, and a combined extract were separately performed with time intervals, respectively, and the effects of the drug samples on preventing or treating colitis were reasonably analyzed based on the group supplied with normal saline solution instead of a specific drug in the model animals not treated with TNBS, for each of the experiments.

(3) Measurements of Weight Change of Model Animals, Colon Appearances, and Myeloperoxidase (MPO) Activity.

1) Analysis of the Amount of Weight Change.

The sample administration to the model animals with colitis induced by TNBS was stopped, and on the following day, the weight of the experimental animals was measured, and the measured weight was compared with the initial weight to calculate the amount of change in weight.

2) Analysis of Appearances.

The scores about the removed colons were estimated by observing the appearances and the length of the colons according to the following criteria (Hollenbach, et al., the criteria about the colitis level in 2005) as listed in Table 1. In this case, as a positive control group, the group administered with Mesalazine® (Sigma) was used. Additionally, a portion of the content in the colon was collected in order to analyze the intestinal microorganisms and stored in a freezer maintained at −80° C. Regarding the colon tissues, the content of the colon was completely removed and then the colon tissues were washed with normal saline solution. Then, some of the tissues were fixed with 4% formaldehyde fixing solution for use as a sample for histopathological examination, and the rest was stored in a freezer at −80° C. for the molecular biological analysis.

TABLE 1

| Macroscopic score | Criteria |
| --- | --- |
| 0 | Presence of no ulcer and no inflammation |
| 1 | Presence of hyperemia without blood |
| 2 | Presence of ulcer with hyperemia |
| 3 | Presence of ulcer and inflammation only in one region |
| 4 | Presence of ulcer and inflammation in two or more regions |
| 5 | Presence of enlarged ulcer by 2 cm or more |

3) Myeloperoxidase (MPO) Activity Measurement.

100 mg of colon tissues were homogenized after adding 200 μL of lysis buffer thereto. The homogenized colon tissues were centrifuged at 4° C. at a rate of 13000 rpm for 15 minutes, the supernatant therefrom was recovered, and the MPO activity was measured using a mouse MPO assay ELISA kit (Hbt HK210, USA). 100 μL of the supernatant was added into a 96-well plate and reacted at room temperature for 1 hour. Upon completion of the reaction, the plate was emptied by overturning, repeatedly washed three times with 200 μL of washing buffer, added with 100 μL of diluted tracer, and then the reaction was allowed to perform at room temperature for 1 hour. Upon completion of the reaction, the plate was emptied by overturning, and each well of the plate was washed using 200 μL of washing buffer. After repeatedly performing the washing process three times using 200 μL of washing buffer, 100 μL of diluted streptavidin-peroxidase conjugate was added thereto, and the reaction was allowed to perform at room temperature for 1 hour. Upon completion of the reaction, the plate was emptied by overturning, and each well of the plate was washed with 200 μL of washing buffer. After repeatedly washing three times using 200 μL of washing buffer, 100 μL of TMB substrate solution was added thereto, the plate was wrapped with an aluminum foil to block out the light, and the reaction was performed at room temperature for 30 minutes. Subsequently, 100 μL of a stop solution was added to terminate the reaction, and the absorbance was measured at 450 nm using an ELISA reader.

4) Results of the Measurements of the Amount of Weight Change, Appearances of Colon, Length of Colon, and MPO Activity.

Figure 3:
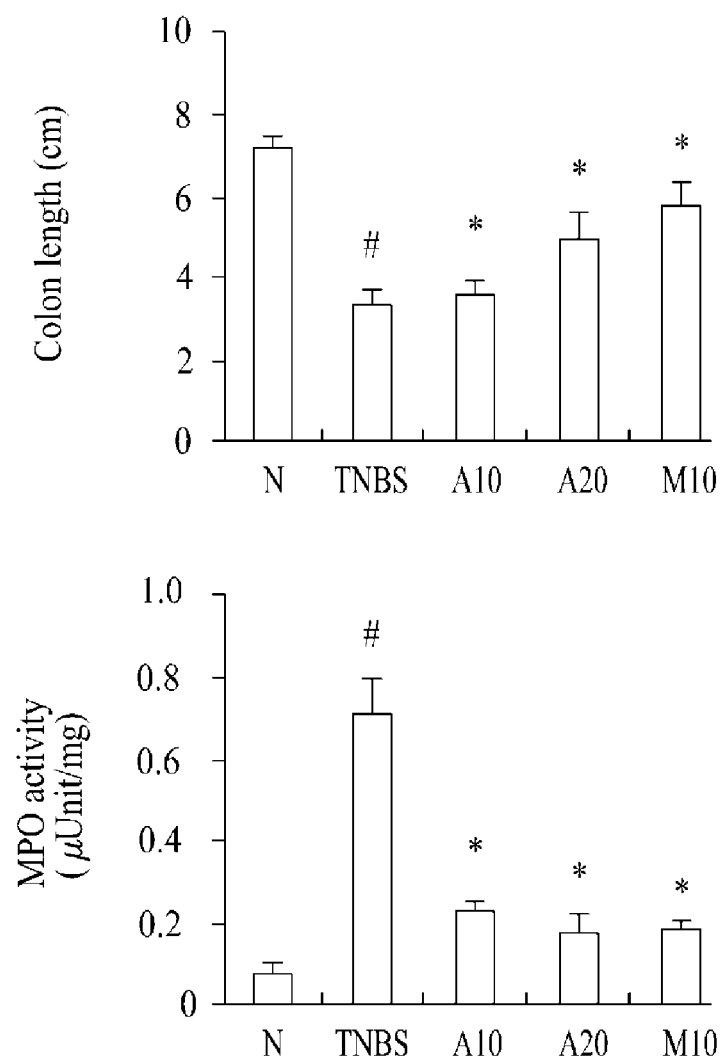
FIG. 3 shows graphs respectively illustrating the colon length and the MPO activity measured in model animals induced with acute colitis by TNBS when the n-butanol-soluble fraction of the *Anemarrhena asphodeloides* Bunge extract obtained in Preparation Example 2 was used as a drug sample.

FIG. 2 illustrates graphs respectively illustrating the weight change and the score on external appearance of colon in model animals induced with acute colitis by TNBS when the n-butanol-soluble fraction of the *Anemarrhena asphodeloides* Bunge extract obtained in Preparation Example 2 was used as a drug sample, and FIG. 3 illustrates the results of the colon length and the MPO activity measured in model animals induced with acute colitis by TNBS when the n-butanol-soluble fraction of the *Anemarrhena asphodeloides* Bunge extract obtained in Preparation Example 2 was used as a drug sample. In FIGS. 2 and 3, "N" or "NOR" represents the normal group, "TNBS" indicates the group, in which normal saline solution instead of a specific drug sample was supplied to the model animal with acute colitis induced by TNBS, and "A" or "AJ" was the n-butanol-soluble fraction of the *Anemarrhena asphodeloides* Bunge extract. Additionally, "A10" and "A20" represent 10 mg/mouse kg and 20 mg/mouse kg as a unit dose of "A", i.e., a drug sample, respectively. Additionally, in FIGS. 2 and 3, "M" represents Mesalazine® used as a positive control drug As illustrated in FIGS. 2 and 3, the n-butanol-soluble fraction of the *Anemarrhena asphodeloides* Bunge extract exhibited the effect of alleviating or improving acute colitis induced by TNBS in a dose-dependent manner.

Figure 4:
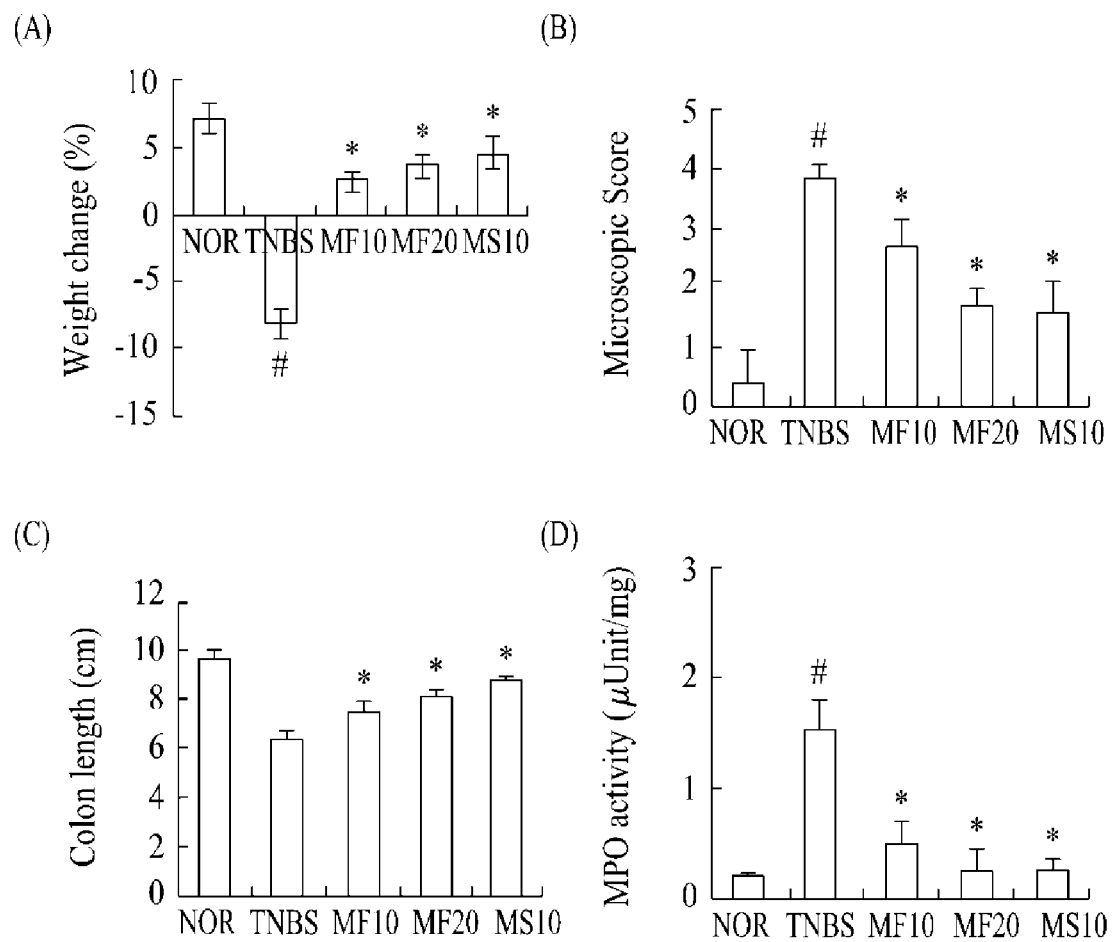
FIG. 4 shows graphs respectively illustrating the weight change, the score on external appearance of colon, the colon length, and the MPO activity measured in model animals induced with acute colitis by TNBS when the mangiferin obtained in Preparation Example 3 was used as a drug sample.

FIG. 4 illustrates the results of the weight change, the score on external appearance of colon, the colon length, and the MPO activity measured in model animals induced with acute colitis by TNBS when the mangiferin obtained in Preparation Example 3 was used as a drug sample. In FIG. 4, "NOR" represents a normal group, and "MF" represents mangiferin. Additionally, "MF10" and "MF20" respectively represent 10 mg/mouse kg and 20 mg/mouse kg as a unit dose of "MF", a drug sample. Additionally, in FIG. 4, "MS" represents Mesalazine® used as a positive control drug. As illustrated in FIG. 4, mangiferin exhibited the effect of alleviating or improving acute colitis induced by TNBS in a dose-dependent manner.

Figure 5:
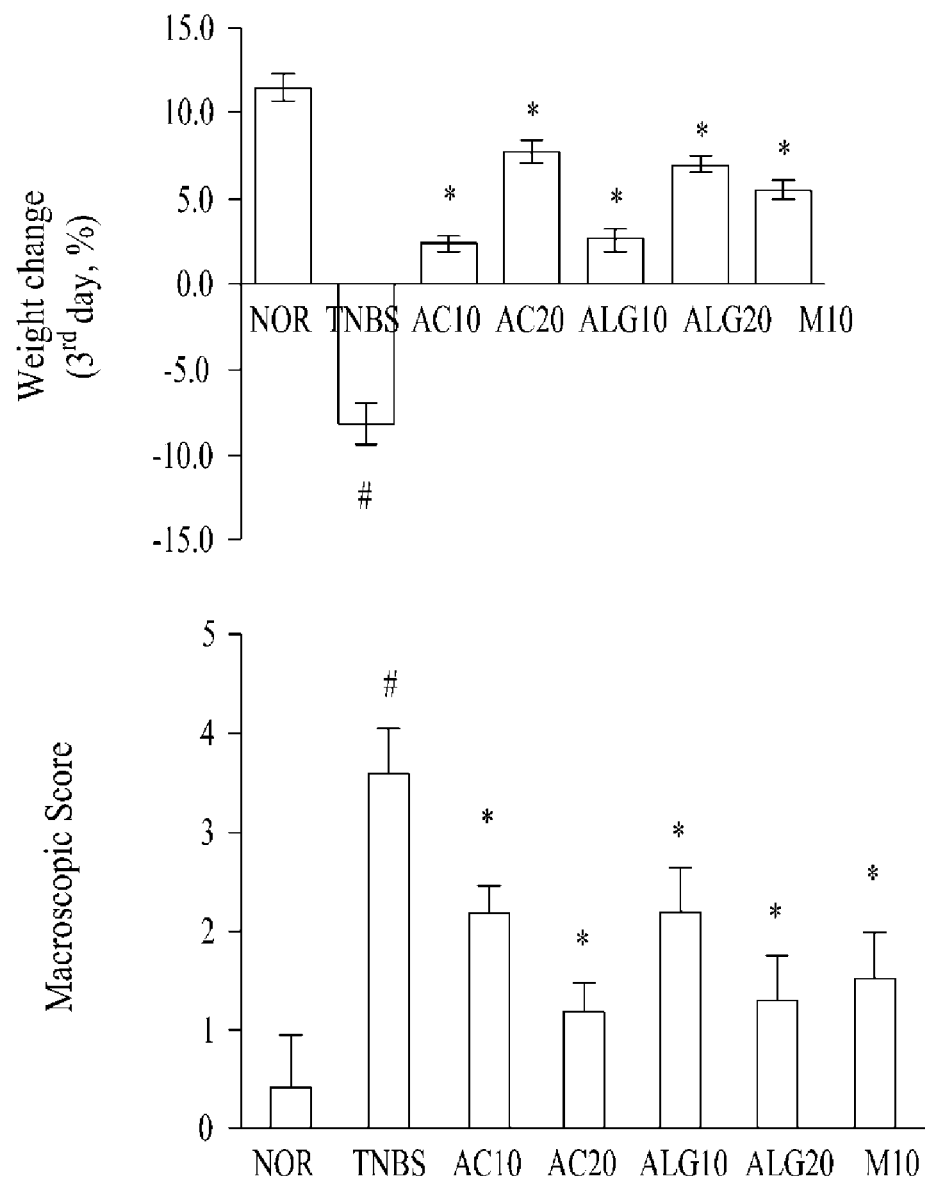
FIG. 5 illustrates graphs respectively illustrating the weight change and the score on external appearance of colon in model animals induced with acute colitis by TNBS when the combined extract were used as a drug sample.
Figure 6:
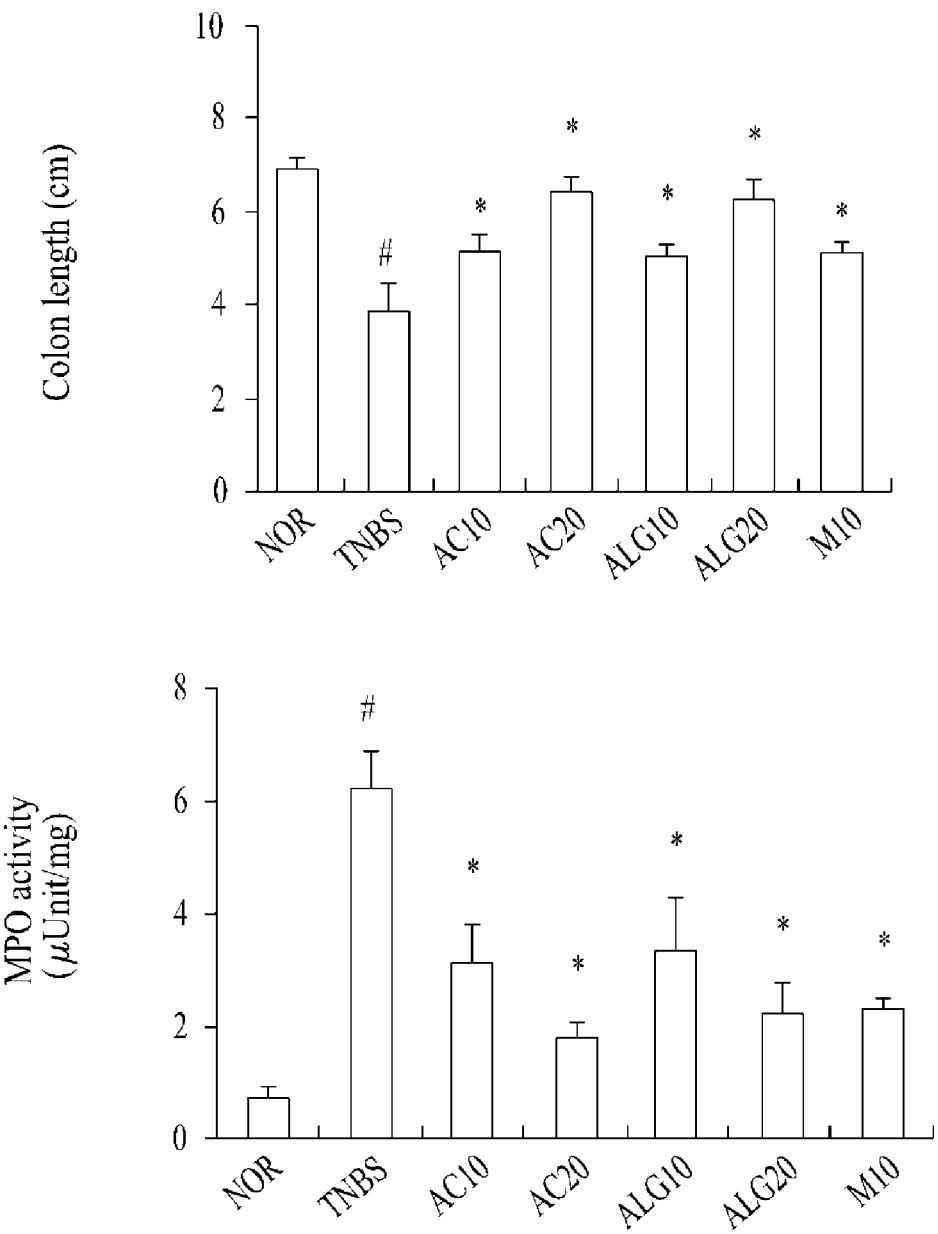
FIG. 6 shows graphs respectively illustrating the colon length and the MPO activity measured in model animals induced with acute colitis by TNBS when the combined extract were used as a drug sample.

FIG. 5 illustrates graphs respectively illustrating the weight change and the score on external appearance of colon in model animals induced with acute colitis by TNBS when the combined extract were used as a drug sample, and FIG. 6 illustrates the results of the colon length and the MPO activity measured in model animals induced with acute colitis by TNBS when the combined extract were used as a drug sample. In FIGS. 5 and 6, "NOR" represents a normal group, "AC" represents the combined extract prepared in Preparation Example 13, and "ALG" represents the combined extract prepared in Preparation Example 12. Additionally, "AC10" and "AC20" respectively represent 10 mg/mouse kg and 20 mg/mouse kg as a unit dose of "AC", a drug sample. Additionally, in FIGS. 5 and 6, "M" represents Mesalazine® used as a positive control drug. As illustrated in FIGS. 5 and 6, the combined extract composed of the fraction of the *Anemarrhena asphodeloides* Bunge extract and the fraction of the *Coptis chinensis* extract, and the combined extract composed of the fraction of the *Anemarrhena asphodeloides* Bunge extract, the fraction of the *Galla Rhois* extract, and the fraction of the *Codonopsis lanceolata* extract exhibited the effect of suppressing acute colitis at a level similar to that of Mesalazine®, and especially, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolata* extract.

(4) Analysis of Effects on Expression of Inflammatory Marker Substances.

1) Effect on Expressions of Proinflammatory Cytokines and Anti-Inflammatory Cytokines.

100 mg of colon tissues of the experimental animals were homogenized after adding 250 μL of RIPA buffer including a protease inhibitor cocktail thereto. Then, the homogenized colon tissues were centrifuged at 4° C. at a rate of 13000 rpm for 15 minutes to obtain a supernatant. While storing the supernatant at −80° C., the expression amount of IL-1β, IL-6, and TNF-α, which correspond to proinflammatory cytokines, and the expression amount of IL-10, which corresponds to an anti-inflammatory cytokine, were measured using a 96-well ELISA plate kit (Pierce Biotechnology, Inc., Rockford, Ill., USA).

Figure 7:
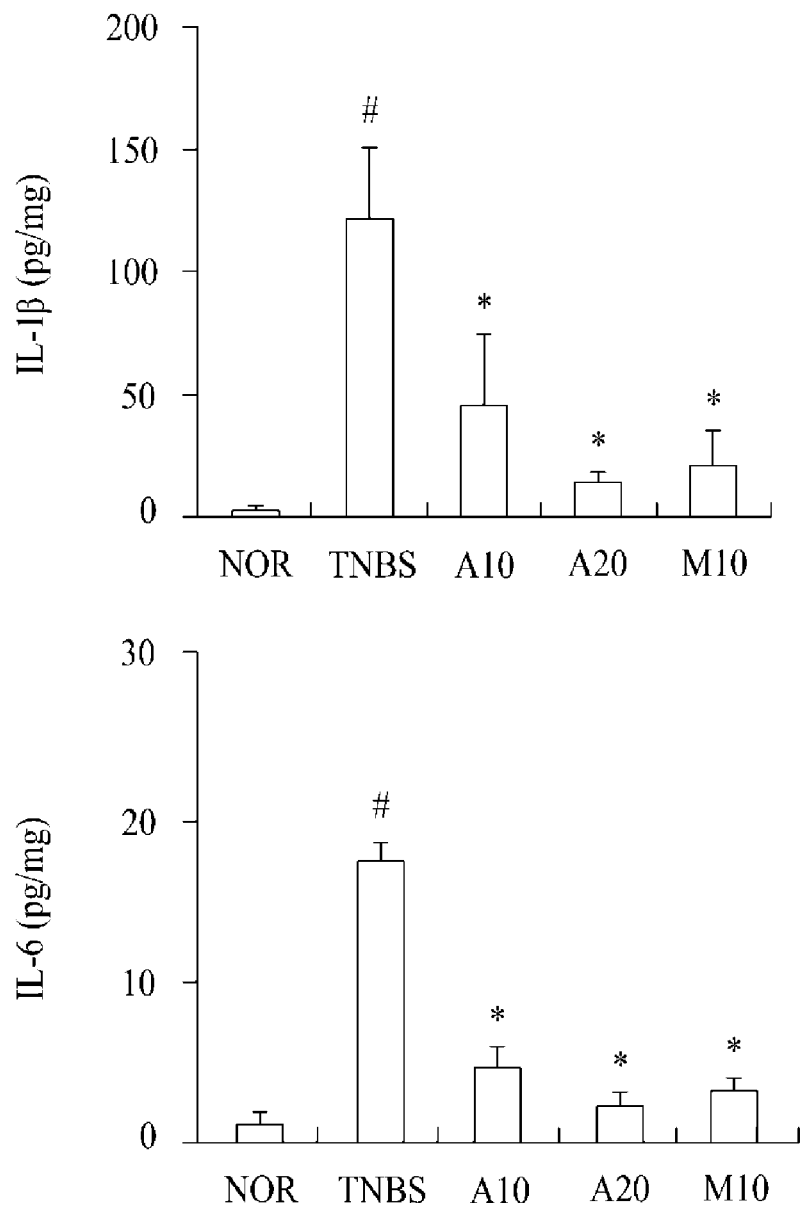
FIG. 7 illustrates graphs respectively illustrating the expression amount of IL-1β and IL-6 in colon tissues of model animals induced with acute colitis by TNBS when the n-butanol-soluble fraction of the *Anemarrhena asphodeloides* Bunge extract obtained in Preparation Example 2 was used as a drug sample.
Figure 8:
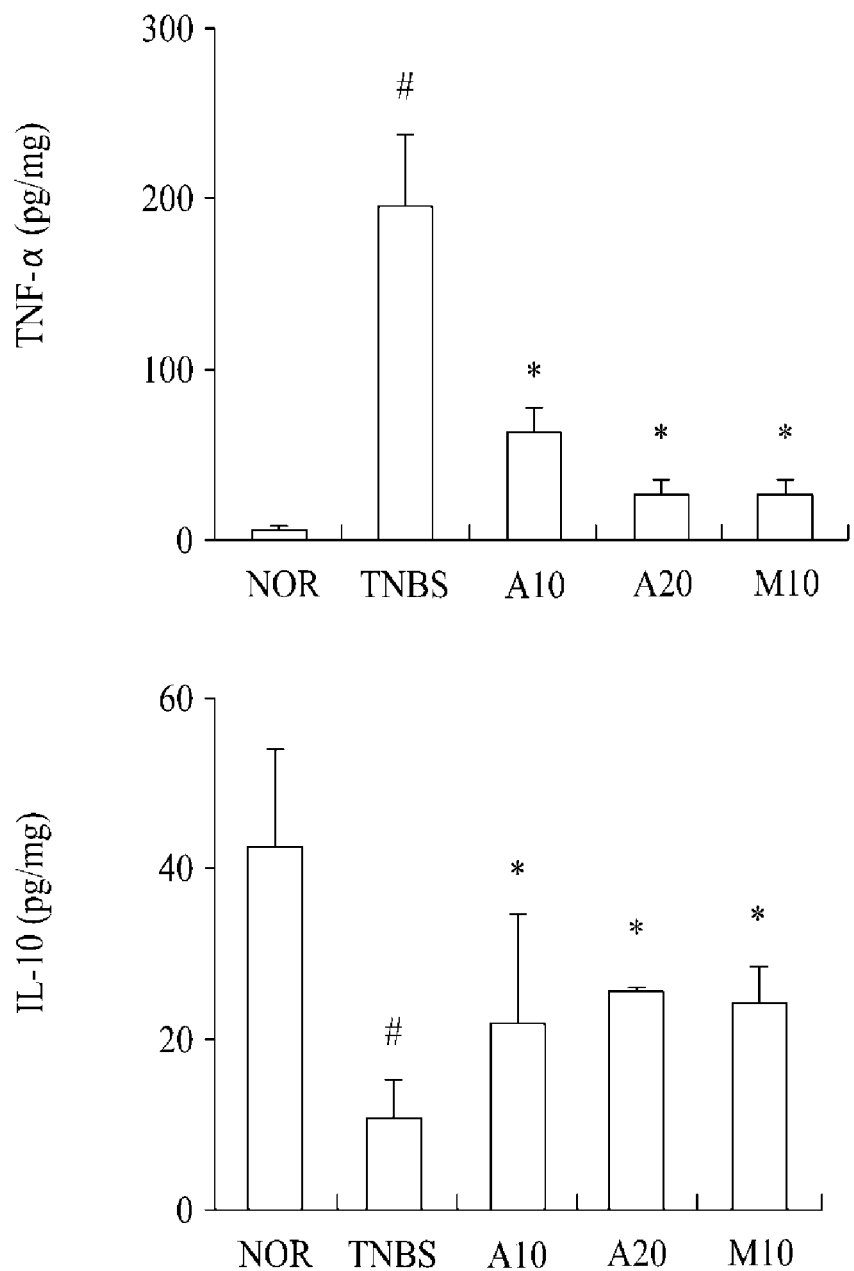
FIG. 8 illustrates graphs respectively illustrating the expression amount of TNF-α and IL-10 in colon tissues of model animals induced with acute colitis by TNBS when the n-butanol-soluble fraction of the *Anemarrhena asphodeloides* Bunge extract obtained in Preparation Example 2 was used as a drug sample.

FIG. 7 illustrates graphs respectively illustrating the expression amount of IL-1β and IL-6 in colon tissues of model animals induced with acute colitis by TNBS when the n-butanol-soluble fraction of the *Anemarrhena asphodeloides* Bunge extract obtained in Preparation Example 2 was used as a drug sample, and FIG. 8 illustrates graphs respectively illustrating the expression amount of TNF-α and IL-10 in colon tissues of model animals induced with acute colitis by TNBS when the n-butanol-soluble fraction of the *Anemarrhena asphodeloides* Bunge extract obtained in Preparation Example 2 was used as a drug sample. In FIGS. 7 and 8, "NOR" represents a normal group, and "A" represents the n-butanol-soluble fraction of the *Anemarrhena asphodeloides* Bunge extract. Additionally, "A10" and "A20" respectively represent 10 mg/mouse kg and 20 mg/mouse kg as a unit dose of "A", a drug sample. Additionally, in FIGS. 7 and 8, "M" represents Mesalazine® used as a positive control drug. As illustrated in FIGS. 7 and 8, when the n-butanol-soluble fraction of the *Anemarrhena asphodeloides* Bunge extract was administered, the expression amount of IL-1β, IL-6, and TNF-α, which correspond to proinflammatory cytokines, was decreased and the expression amount of IL-10, which corresponds to an anti-inflammatory cytokine, increased in the colon tissues of model animals with acute colitis induced by TNBS in a dose-dependent manner.

Figure 9:
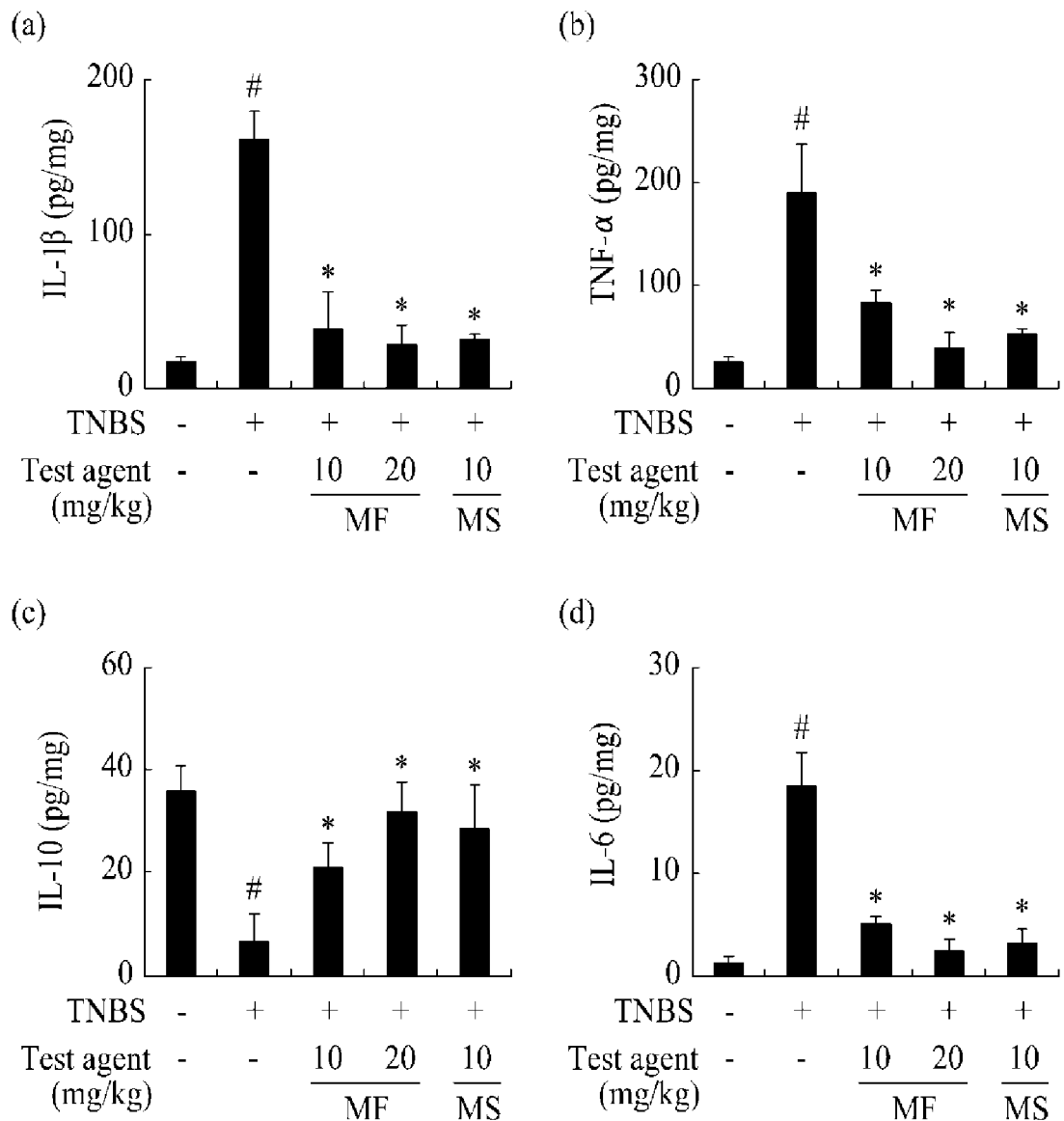
FIG. 9 illustrates graphs respectively illustrating the expression amount of proinflammatory cytokine and anti-inflammatory cytokine in colon tissues of model animals induced with acute colitis by TNBS when the mangiferin obtained in Preparation Example 3 was used as a drug sample.

FIG. 9 illustrates graphs respectively illustrating the expression amount of proinflammatory cytokine and anti-inflammatory cytokine in colon tissues of model animals induced with acute colitis by TNBS when the mangiferin obtained in Preparation Example 3 was used as a drug sample. In FIG. 9, "MF" represents mangiferin and "MS" represents Mesalazine® used as a positive control drug. As illustrated in FIG. 9, when mangiferin was administered, the expression amount of IL-1β, IL-6, and TNF-α, which correspond to proinflammatory cytokines, was decreased and the expression amount of IL-10, which corresponds to an anti-inflammatory cytokine, was increased in the colon tissues of model animals with acute colitis induced by TNBS in a dose-dependent manner.

Figure 10:
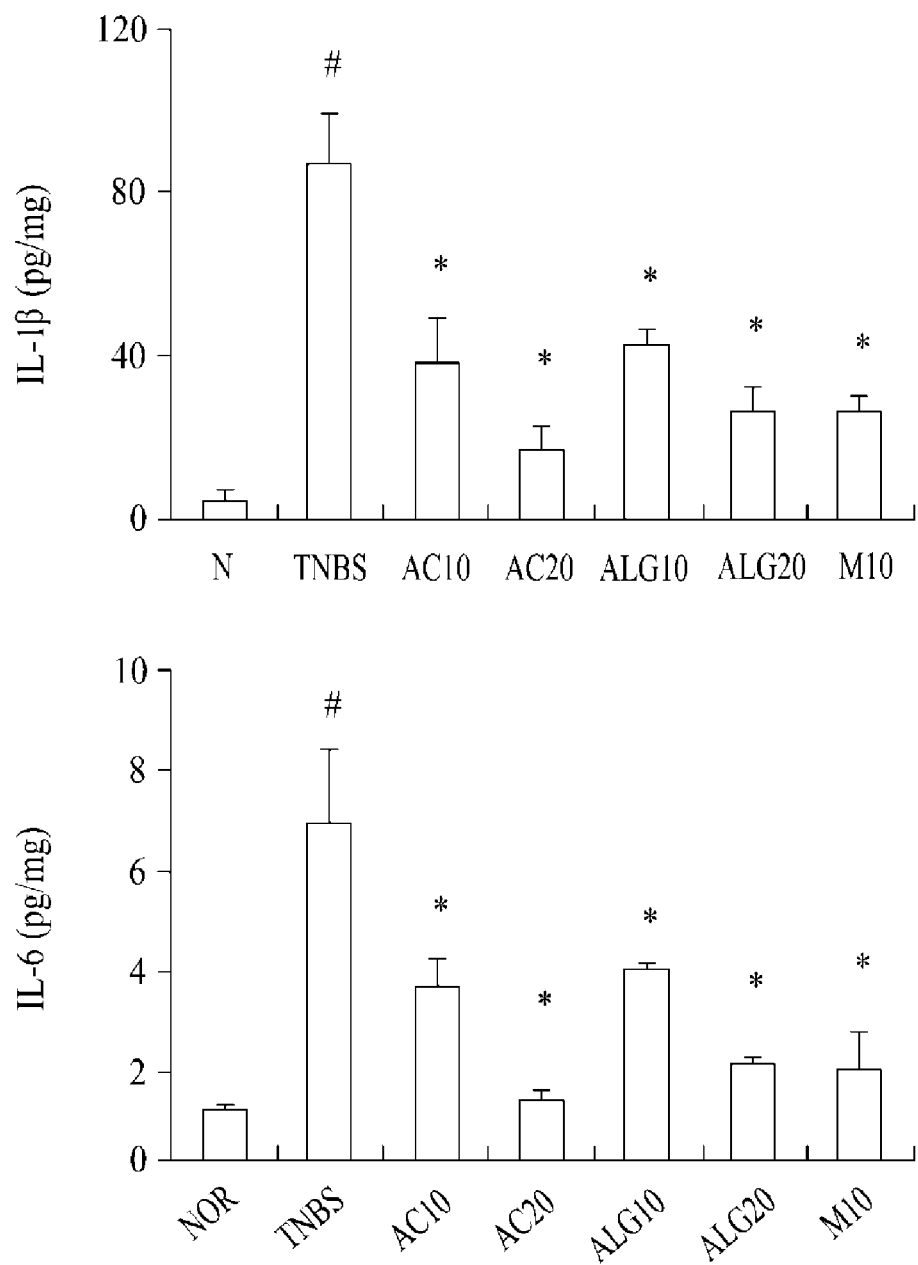
FIG. 10 illustrates graphs respectively illustrating the expression amount of IL-1β and IL-6 in colon tissues of model animals induced with acute colitis by TNBS when the combined extract were used as a drug sample.
Figure 11:
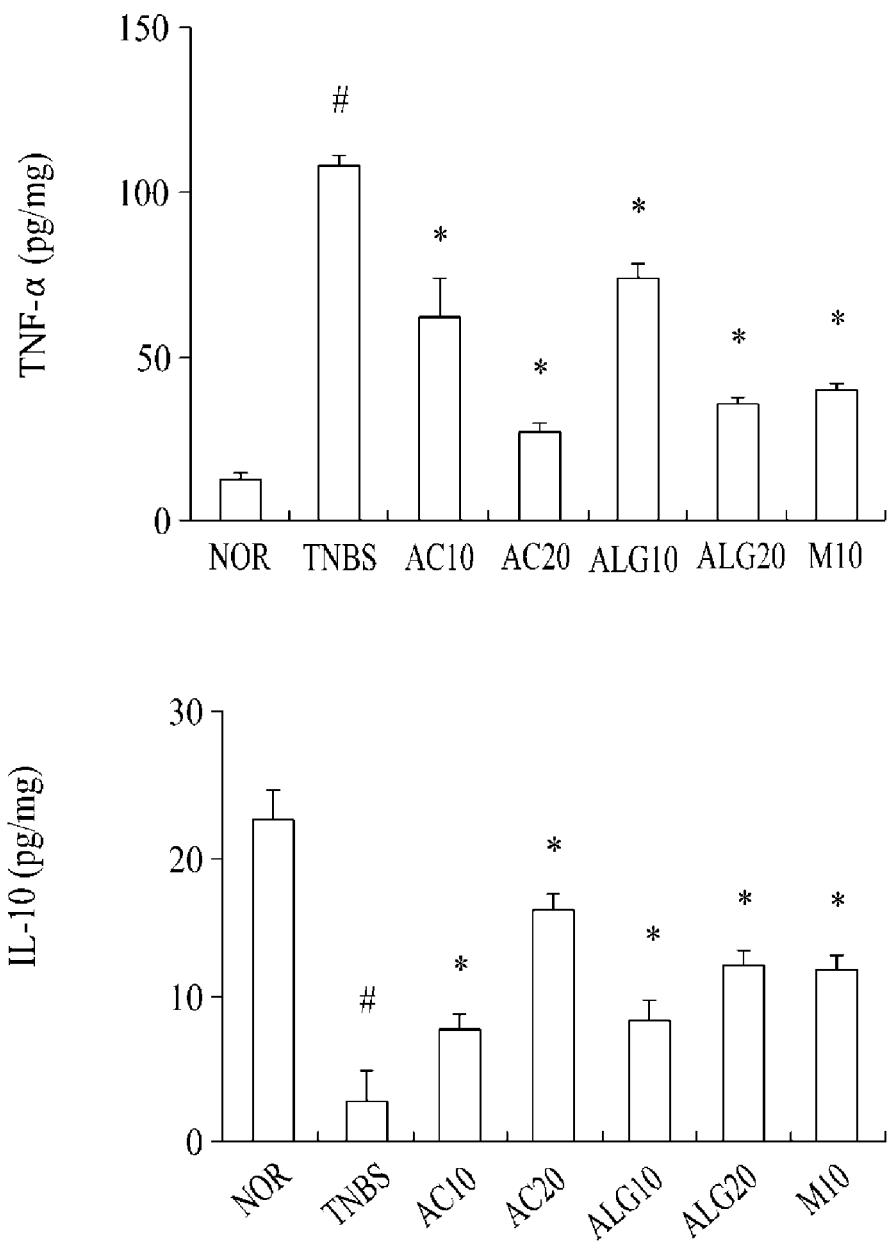
FIG. 11 illustrates graphs respectively illustrating the expression amount of TNF-α and IL-10 in colon tissues of model animals induced with acute colitis by TNBS when the combined extract were used as a drug sample.

FIG. 10 illustrates graphs respectively illustrating the expression amount of IL-1β and IL-6 in colon tissues of model animals induced with acute colitis by TNBS when the combined extract were used as a drug sample, and FIG. 11 illustrates graphs respectively illustrating the expression amount of TNF-α and IL-10 in colon tissues of model animals induced with acute colitis by TNBS when the combined extract were used as a drug sample. In FIGS. 10 and 11, "N" or "NOR" represents a normal group, "AC" represents the combined extract prepared in Preparation Example 13, and "ALG" represents the combined extract prepared in Preparation Example 12. Additionally, "AC10" and "AC20" respectively represent 10 mg/mouse kg and 20 mg/mouse kg as a unit dose of "AC", a drug sample. Additionally, in FIGS. 10 and 11, "M" represents Mesalazine® used as a positive control drug. As illustrated in FIGS. 10 and 11, the combined extract composed of the fraction of the *Anemarrhena asphodeloides* Bunge extract and the fraction of the *Coptis chinensis* extract, and the combined extract composed of the fraction of the *Anemarrhena asphodeloides* Bunge extract, the fraction of the *Galla Rhois* extract, and the fraction of the *Codonopsis lanceolate* extract decreased the expressions of proinflammatory cytokines while increasing the expression of anti-inflammatory cytokine to a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolate* extract.

2) Presence of Suppression on the Expressions of Inflammatory Marker Substances.

0.3 g of the colon tissues of the experimental animals were homogenized after adding 1 mL of RIPA buffer (Gibco) including a protease inhibitor cocktail thereto. Then, the homogenized colon tissues were centrifuged at 4° C. at a rate of 13000 rpm for 15 minutes to obtain a supernatant. While storing the supernatant at −80° C., the expression amount of COX-2, iNOS, p65 (NF-Kappa B), p-p65 (phosphor-NF-Kappa B), and β-actin was measured by a Western blot analysis. First, 50 µg of the supernatant was subjected to an electrophoresis on an SDS 10% (w/v) polyacrylamide gel for 1 hour and 30 minutes, and the electrophoresed samples were transferred onto a nitrocellulose paper under the condition of 100 V and 400 mA for 1 hour and 10 minutes. The nitrocellulose paper transferred with the samples was blocked with 5% skim milk for 30 minutes, washed with PBS-Tween for 5 minutes three times, and a reaction was performed overnight with primary antibodies (Santa Cruz Biotechnology, USA) at a ratio of 1:100. Then, the paper was washed for 10 minutes three times and the reaction was performed with secondary antibodies (Santa Cruz Biotechnology, USA) at a ratio of 1:1000 for 1 hour and 20 minutes. Subsequently, the paper was washed for 15 minutes three times, colored with fluorescence, and then developed.

Figure 12:
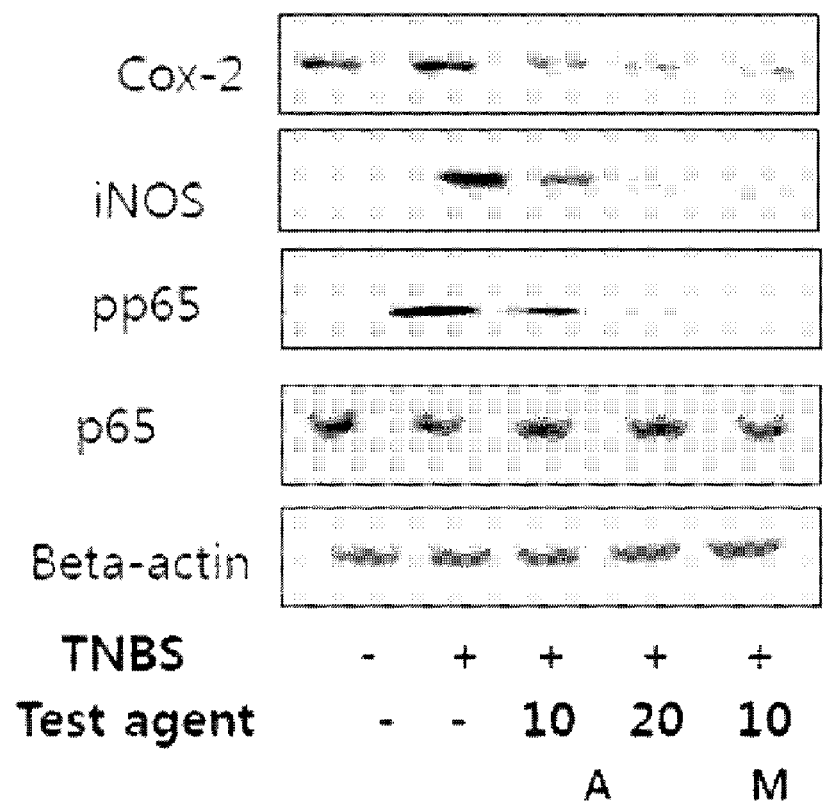
FIG. 12 illustrates the results of inhibition of inflammatory marker substance expression in colon tissues of model animals induced with acute colitis by TNBS when the model animals were administered with the n-butanol-soluble fraction of the *Anemarrhena asphodeloides* Bunge extract obtained in Preparation Example 2.

FIG. 12 illustrates the results of inhibition of inflammatory marker substance expression in colon tissues of model animals induced with acute colitis by TNBS when the model animals were administered with the n-butanol-soluble fraction of the *Anemarrhena asphodeloides* Bunge extract obtained in Preparation Example 2. In FIG. 12, "A" represents an n-butanol-soluble fraction of the *Anemarrhena asphodeloides* Bunge extract, and "M" represents Mesalazine® used as a positive control drug, and the unit dose of the drug sample is mg/mouse kg.

Figure 13:
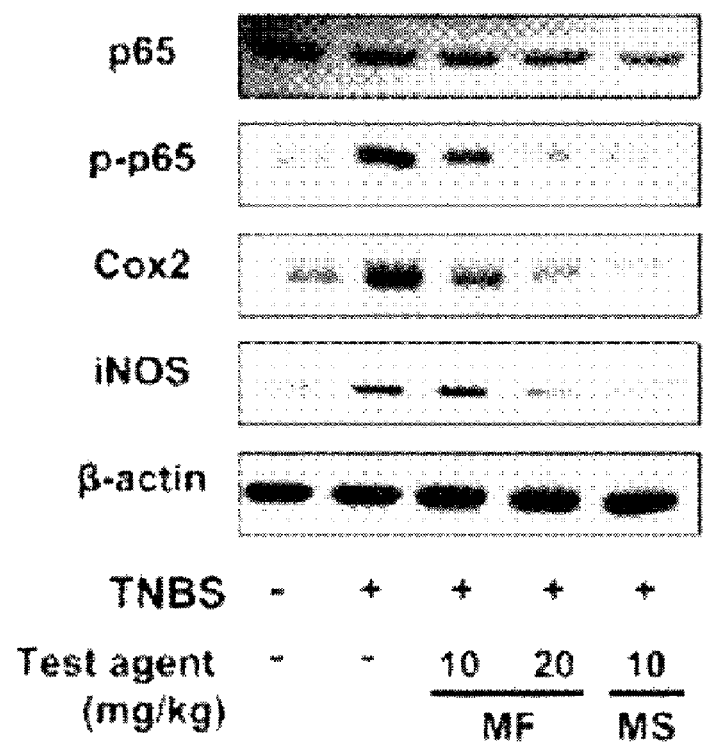
FIG. 13 illustrates the results of inhibition of inflammatory marker substance expression in colon tissues of model animals induced with acute colitis by TNBS when the model animals were administered with the mangiferin obtained in Preparation Example 3.

FIG. 13 illustrates the results of inhibition of inflammatory marker substance expression in colon tissues of model animals induced with acute colitis by TNBS when the model animals were administered with the mangiferin obtained in Preparation Example 3. In FIG. 13, "MF" represents mangiferin and "MS" represents Mesalazine® used as a positive control drug.

Figure 14:
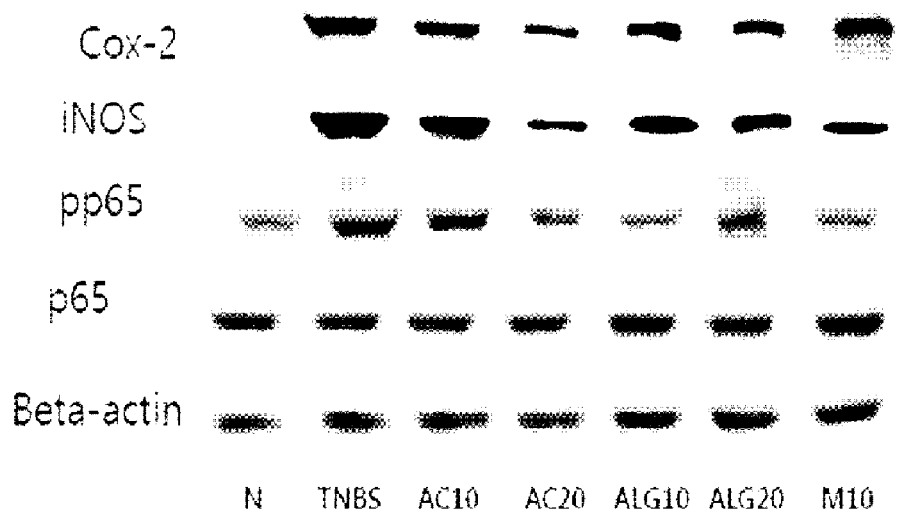
FIG. 14 illustrates the results of inhibition of inflammatory marker substance expression in colon tissues of model animals induced with acute colitis by TNBS when the model animals were administered with a combined extract.

FIG. 14 illustrates the results of inhibition of inflammatory marker substance expression in colon tissues of model animals induced with acute colitis by TNBS when the model animals were administered with a combined extract. In FIG. 14, "N" represents the normal group, "AC" represents the combined extract prepared in Preparation Example 13, and "ALG" represents the combined extract prepared in Preparation Example 12. Additionally, "AC10" and "AC20" respectively represent that the unit dose of "AC", a sample drug, is 10 mg/mouse kg and 20 mg/mouse kg. Additionally, in FIG. 14, "M" represents Mesalazine® used as a positive control drug. As illustrated in FIG. 14, the combined extract composed of the fraction of the *Anemarrhena asphodeloides* Bunge extract and the fraction of the *Coptis chinensis* extract, and the combined extract composed of the fraction of the *Anemarrhena asphodeloides* Bunge extract, the fraction of the *Galla Rhois* extract, and the fraction of the *Codonopsis lanceolate* extract inhibited the expression of COX-2, iNOS, and p-p65 (phosphor-NF-kappa B), which are inflammatory marker substances, to a level similar to that of Mesalazine®, which was used as a positive control drug. Specifically, the combined extract of the fraction of the

*Anemarrhena asphodeloides* Bunge extract and the fraction of the *Coptis chinensis* extract exhibited more excellent effect, compared with the combined extract composed of the fraction of the *Anemarrhena asphodeloides* Bunge extract, Bunge, is used instead of the fraction of the *Anemarrhena asphodeloides* Bunge extract, or when the *Coptis chinensis* extract is used instead of the fraction of the *Coptis chinensis* extract.

TABLE 2

| Experimental Groups | | | Values of analyzed items (Percentage to normal group supplied with saline solution without TNBS treatment, %) | | | | | | | |
|---|---|---|---|---|---|---|---|---|---|---|
| Presence of TNBS treatment | Drug sample for administration | Unit dose of drug sample (mg/kg) | Body weight | Macroscopic score | Colon length | MPO activity | TNF-α | IL-1β | IL-6 | IL-10 |
| − | vehicle | — | 100 | 100 | 100 | 100 | 100 | 100 | 100 | 100 |
| + | vehicle | — | 82.1 | 900.9 | 58.0 | 2325.6 | 826.4 | 2040.8 | 714.3 | 12.5 |
| + | Prep. Ex. 2 | 20 | 92.0 | 600.9 | 66.7 | 1214.0 | 246.3 | 608.2 | 425.7 | 56.3 |
| + | Prep. Ex. 5 | 20 | 93.4 | 650.5 | 66.7 | 1011.6 | 267.8 | 695.9 | 449.3 | 49.6 |
| + | Prep. Ex. 7 | 20 | 91.1 | 700.9 | 62.3 | 1516.3 | 305.8 | 734.7 | 533.6 | 31.7 |
| + | Prep. Ex. 9 | 20 | 90.2 | 650.5 | 66.7 | 1618.6 | 240.5 | 679.6 | 415.0 | 45.5 |
| + | Prep. Ex. 11 | 20 | 92.9 | 600.9 | 66.7 | 1111.6 | 244.6 | 589.8 | 392.1 | 57.1 |
| + | Prep. Ex. 13 | 20 | 95.8 | 350.5 | 92.8 | 707.0 | 206.6 | 385.7 | 167.9 | 71.9 |
| + | Prep. Ex. 10 | 20 | 91.6 | 550.5 | 69.6 | 1111.6 | 236.4 | 657.1 | 323.6 | 65.6 |
| + | Prep. Ex. 12 | 20 | 93.4 | 450.5 | 72.5 | 909.3 | 268.6 | 610.2 | 201.4 | 54.5 |
| + | Mesalazine ® | 10 | 93.2 | 550.5 | 89.9 | 1111.6 | 304.1 | 618.4 | 190.0 | 53.1 | the fraction of the *Galla Rhois* extract, and the fraction of the *Codonopsis lanceolate* extract.

(5) Summary of Experimental Results of Model Animals with Acute Colitis Induced by TNBS.

The summary of the effects of the drug samples administered to the model animals with acute colitis induced by TNBS on alleviating or improving colitis are listed in the following Table 2. In the following Table 2, the values of analyzed item are represented as a percentage to the value of the normal group supplied with saline solution instead of the specific drug sample in the model animals not treated with TNBS.

As listed in the following Table 2, when the combined extract composed of the fraction of the *Anemarrhena asphodeloides* Bunge extract and the fraction of the *Coptis chinensis* extract or the combined extract composed of the fraction of the *Anemarrhena asphodeloides* Bunge extract, the fraction of the *Galla Rhois* extract, and the fraction of the *Codonopsis lanceolate* extract were administered to the model animals with acute colitis induced by TNBS, the combined extract exhibited a markedly improved effect in alleviating or improving colitis, compared with each of the cases administered with the fraction of the *Anemarrhena asphodeloides* Bunge extract, the fraction of the *Galla Rhois* extract, the fraction of the *Codonopsis lanceolate* extract, or the fraction of the *Coptis chinensis* extract, respectively. Specifically, the combined extract composed of the fraction of the *Anemarrhena asphodeloides* Bunge extract and the fraction of the *Coptis chinensis* extract exhibited more excellent effect compared with the combined extract composed of the fraction of the *Anemarrhena asphodeloides* Bunge extract, the fraction of the *Galla Rhois* extract, and the fraction of the *Codonopsis lanceolate* extract. It is speculated that this is because the fraction of the *Anemarrhena asphodeloides* Bunge extract and the fraction of the *Coptis chinensis* extract acted on different targets to each other, in which the targets were related to the alleviation or treatment of colitis, thereby exhibiting a synergistic effect. Additionally, the same effect of alleviating or improving colitis is expected to be obtained when the *Anemarrhena asphodeloides* Bunge extract or mangiferin, which is a compound isolated from an *Anemarrhena asphodeloides*

However, when the combined extract composed of the fraction of the *Anemarrhena asphodeloides* Bunge extract and the fraction of *the Codonopsis lanceolata* extract, or the combined extract composed of the fraction of the *Anemarrhena asphodeloides* Bunge extract and the fraction of the *Galla Rhois* extract was administered to the model animals with acute colitis induced by TNBS, there was no significant difference in the effect of alleviating or improving colitis, compared with when the fraction of the *Anemarrhena asphodeloides* Bunge extract, the fraction of the *Galla Rhois* extract, the fraction of the *Codonopsis lanceolate* extract, or the fraction of the *Coptis* extract was administered alone.

7. Measurement of Effect of Treating Colitis in Experimental Model Animals with Acute Colitis Induced by DSS.

(1) Preparation of Experimental Animals.

6-week old male mice (C57BL/6, 18 g to 22 g) were purchased from OrientBio Inc. All the mice were bred under the controlled environmental conditions of 50±10% of humidity at a temperature of 20° C. to 22° C., and the lighting was provided by repeatedly turning on for 12 hours followed by turning off for 12 hours. A feed for a standard experiment (Samyang, Korea) was used as a feed, and ad libitum access to water was allowed. In all experiments, each group consisted of 6 mice.

(2) Induction of Acute Colitis by DSS and Sample Administration.

Among the experimental groups, one group was set as a normal group, and the experimental animals in other groups were induced with acute colitis by dextran sulfate sodium (molecular weight: 36 kDaltons to 50 kDaltons). In detail, the animal models with acute colitis were prepared by feeding them with a 2.5% (w/v) aqueous dextran sulfate sodium solution for 7 days instead of water as drinking water. Meanwhile, the normal group was fed with water as drinking water. From the following day, the sample dissolved in normal saline solution was orally administered at the predetermined volume once daily for 3 days. On the following day after completing the sample administration, the experimental animals were suffocated to death with carbon dioxide, and the colon from the appendix to the region immediately before the anus was removed from the colon region.

(3) Measurements of Weight Change of Model Animals, Colon Appearances, and Myeloperoxidase (MPO) Activity.

1) Analysis of the Amount of Weight Change.

The amount of change in body weight was analyzed in the same manner as in the experiment for the model animals with colitis induced by TNBS.

2) Appearance Analysis.

The appearance of colon was analyzed in the same manner as in the experiment for the model animals with colitis induced by TNBS.

3) Measurement of MPO Activity.

The myeloperoxidase (MPO) activity was measured in the same manner as in the experiment for the model animals with colitis induced by TNBS.

4) Results of Measuring Amount of Weight Change, Appearance of Colon, Colon Length, and MPO Activity.

Figure 15:
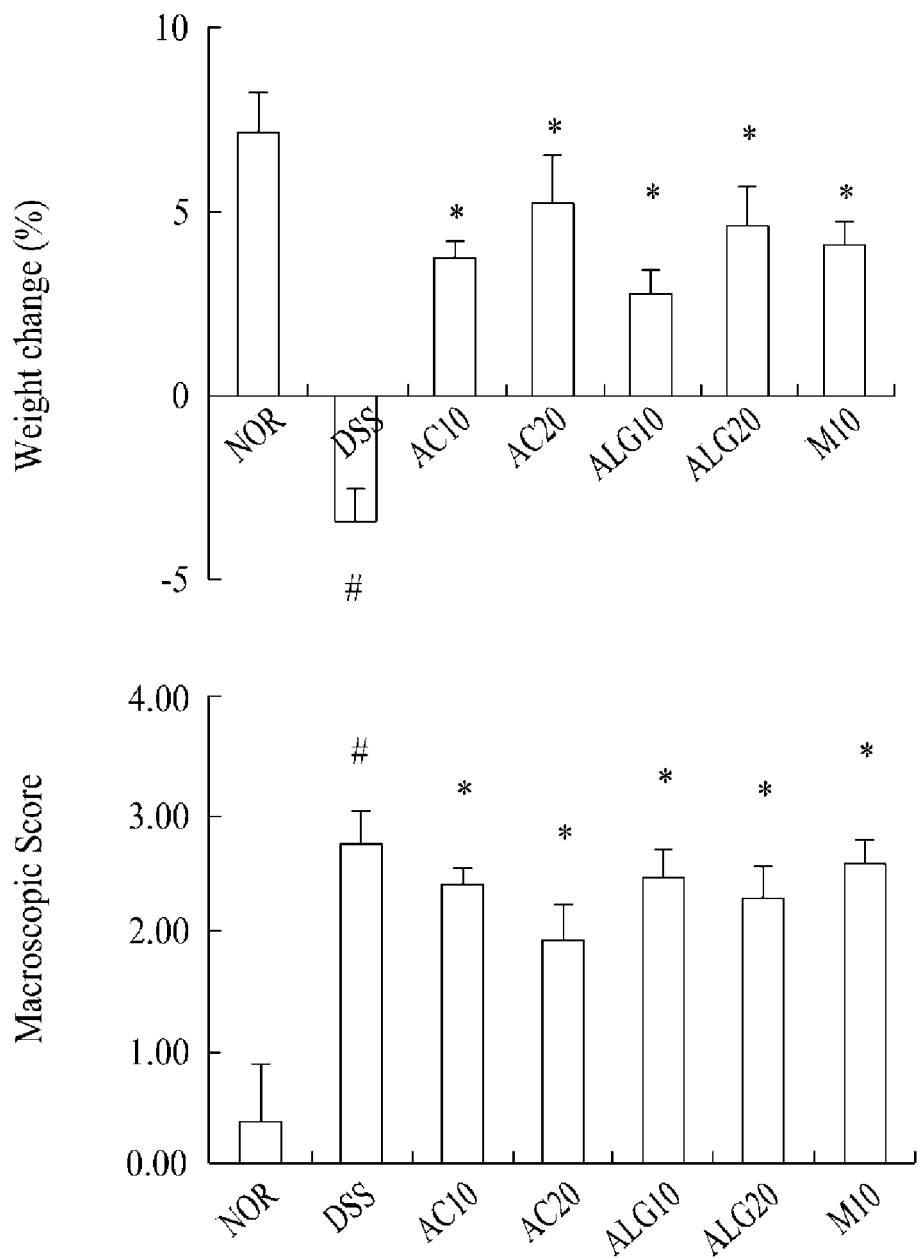
FIG. 15 illustrates graphs respectively illustrating the weight change and the score on external appearance of colon in model animals induced with acute colitis by DSS when the combined extract was used as a drug sample.
Figure 16:
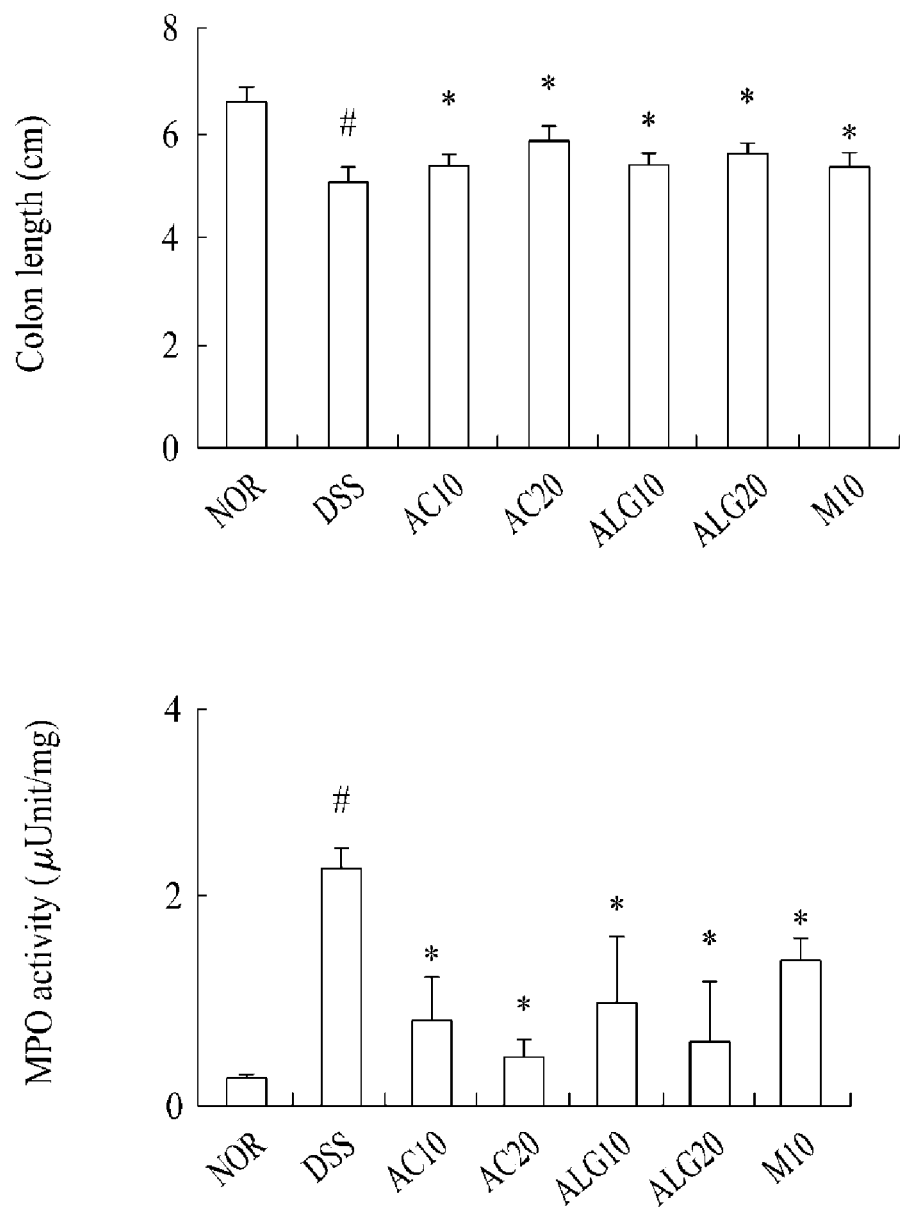
FIG. 16 illustrates the results of the colon length and the MPO activity measured in model animals induced with acute colitis by DSS when the combined extract was used as a drug sample.

FIG. 15 illustrates graphs respectively illustrating the weight change and the score on external appearance of colon in model animals induced with acute colitis by DSS when the combined extract was used as a drug sample, and FIG. 16 illustrates the results of the colon length and the MPO activity measured in model animals induced with acute colitis by DSS when the combined extract was used as a drug sample. In FIGS. 15 and 16, "NOR" represents a normal group, "AC" represents the combined extract prepared in Preparation Example 13, and "ALG" represents the combined extract prepared in Preparation Example 12. Additionally, "AC10" and "AC20" respectively represent 10 mg/mouse kg and 20 mg/mouse kg as a unit dose of "AC", which is a drug sample. Additionally, in FIGS. 15 and 16, "M" represents Mesalazine® used as a positive control drug. As illustrated in FIGS. 15 and 16, the combined extract composed of the fraction of the *Anemarrhena asphodeloides* Bunge extract and the fraction of the *Coptis chinensis* extract and the combined extract composed of the fraction of the *Anemarrhena asphodeloides* Bunge extract, the fraction of the *Galla Rhois* extract, and the fraction of the *Codonopsis lanceolata* extract suppressed acute colitis to a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolate* extract.

(4) Analysis of Effects on Expression of Inflammatory Marker Substances.

1) Effect on Expressions of Proinflammatory Cytokines and Anti-Inflammatory Cytokines.

The expression amount of proinflammatory cytokines and anti-inflammatory cytokines in colon tissues of model animals with acute colitis induced by DSS, when administered with a drug sample, was measured in the same manner as in the experiment for the model animals with colitis induced by TNBS.

Figure 17:
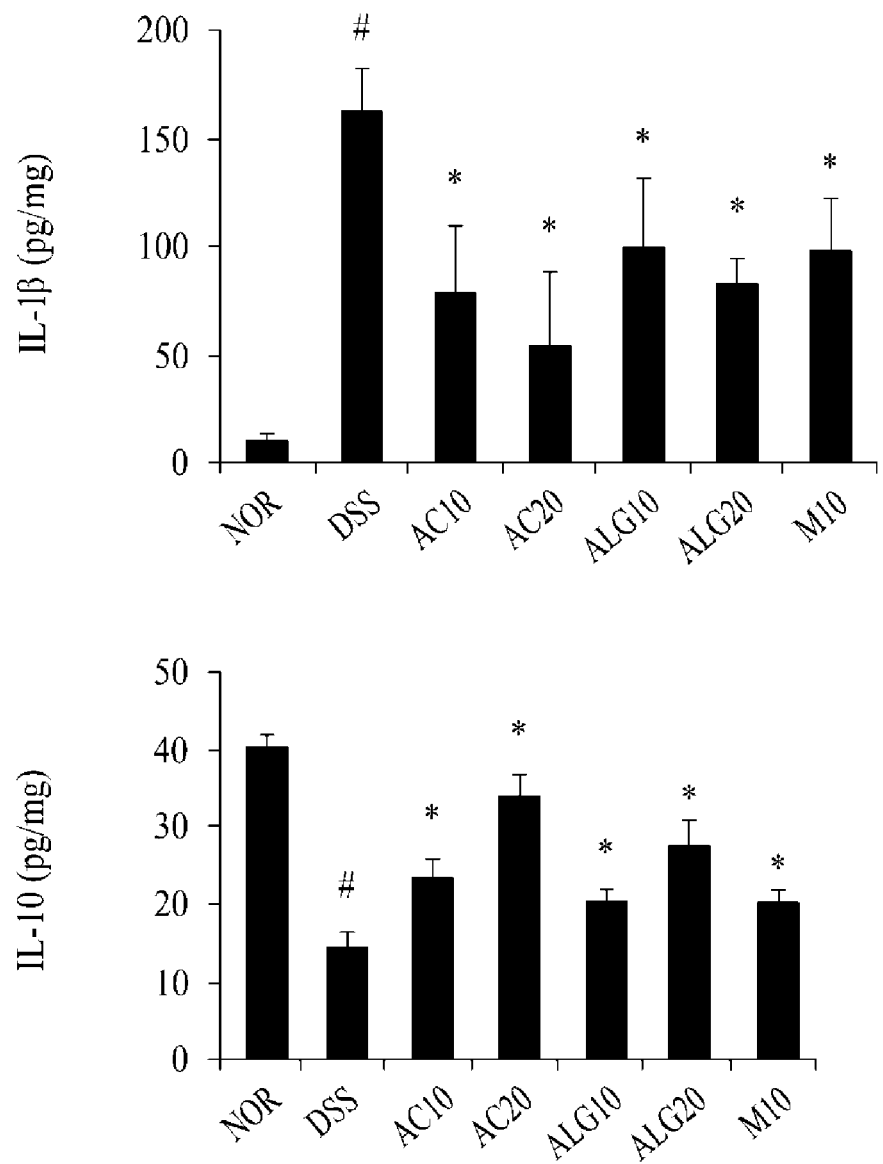
FIG. 17 illustrates graphs respectively illustrating the expression amount of IL-1β and IL-10 in colon tissues of model animals induced with acute colitis by DSS when the combined extract was used as a drug sample.
Figure 18:
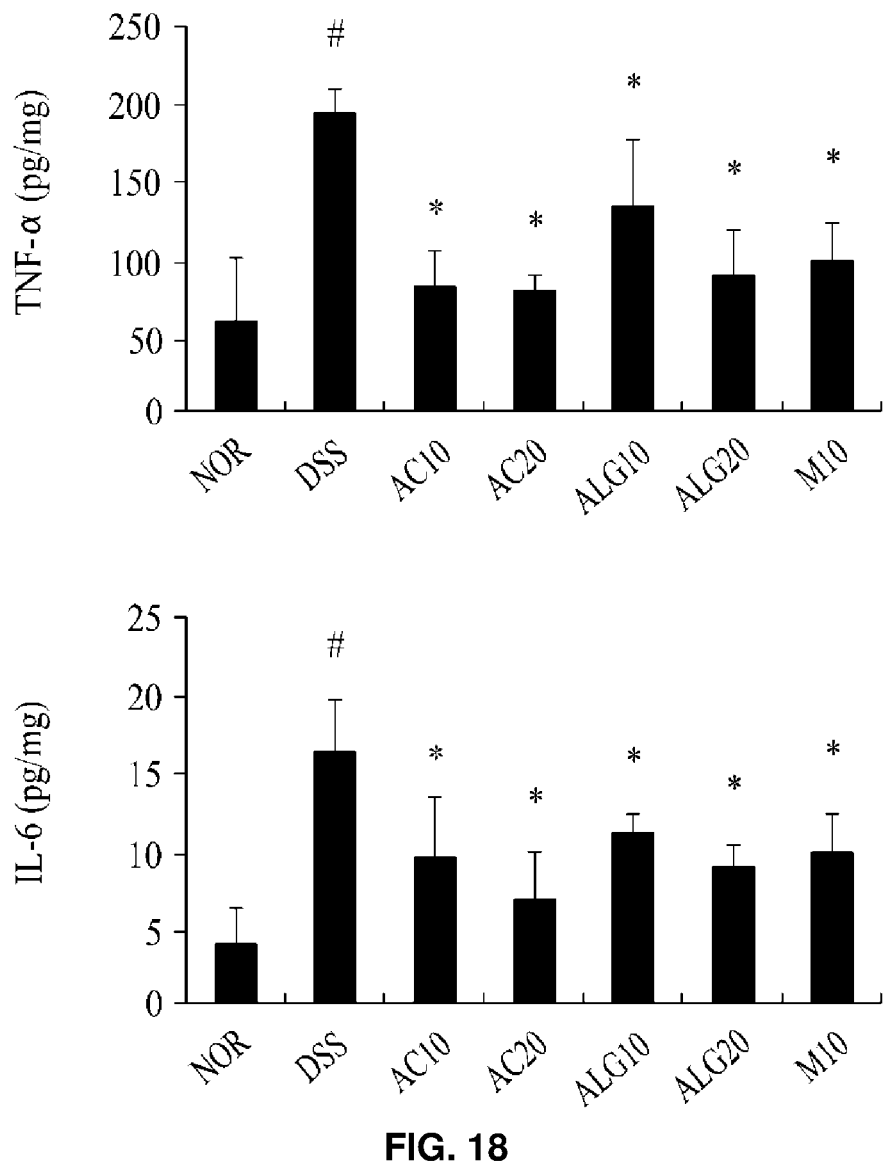
FIG. 18 illustrates graphs respectively illustrating the expression amount of TNF-α and IL-6 in colon tissues of model animals induced with acute colitis by DSS when the combined extract was used as a drug sample.

FIG. 17 illustrates graphs respectively illustrating the expression amount of IL-1β and IL-10 in colon tissues of model animals induced with acute colitis by DSS when the combined extract was used as a drug sample, and FIG. 18 illustrates graphs respectively illustrating the expression amount of TNF-α and IL-6 in colon tissues of model animals induced with acute colitis by DSS when the combined extract was used as a drug sample.

In FIGS. 17 and 18, "NOR" represents a normal group, "AC" represents the combined extract prepared in Preparation Example 13, and "ALG" represents the combined extract prepared in Preparation Example 12. Additionally, "AC10" and "AC20" respectively represent 10 mg/mouse kg and 20 mg/mouse kg as a unit dose of "AC", which is a drug sample. Additionally, in FIGS. 17 and 18, "M" represents Mesalazine® used as a positive control drug. As illustrated in FIGS. 17 and 18, the combined extract composed of the fraction of the *Anemarrhena asphodeloides* Bunge extract and the fraction of the *Coptis chinensis* extract and the combined extract composed of the fraction of the *Anemarrhena asphodeloides* Bunge extract, the fraction of the *Galla Rhois* extract, and the fraction of the *Codonopsis lanceolate* extract decreased the expressions of proinflammatory cytokines while increasing the expressions of anti-inflammatory cytokines to a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolate* extract.

2) Presence of Inhibition on Expression of Inflammatory Marker substaNces.

The expression amount of COX-2, iNOS, p65 (NF-Kappa B), p-p65 (phosphor-NF-Kappa B), and β-actin in the colon tissues of model animals with acute colitis induced by DSS, when administered with a drug sample, was measured in the same manner as in the experiment for model animals with colitis induced by TNBS.

Figure 19:
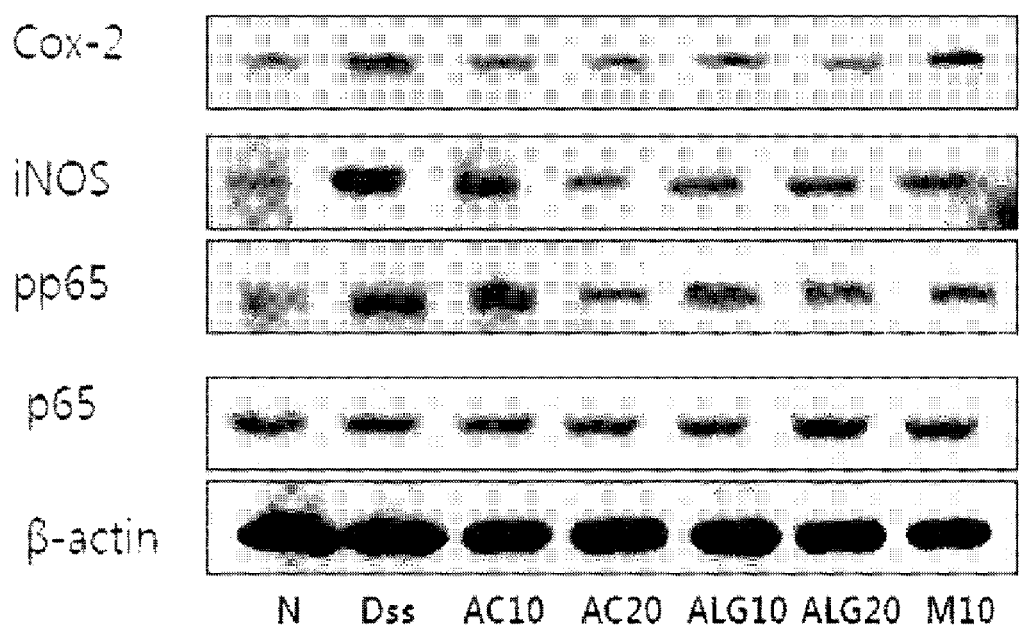
FIG. 19 illustrates the results of inhibition of inflammatory marker substance expression in colon tissues of model animals induced with acute colitis by DSS when the model animals were administered with a combined extract.

FIG. 19 illustrates the results of inhibition of inflammatory marker substance expression in colon tissues of model animals induced with acute colitis by DSS when the model animals were administered with a combined extract. In FIG. 19, "N" represents a normal group, "AC" represents the combined extract prepared in Preparation Example 13, and "ALG" represents the combined extract prepared in Preparation Example 12. Additionally, "AC10" and "AC20" respectively represent 10 mg/mouse kg and 20 mg/mouse kg as a unit dose of "AC" that is a drug sample. Additionally, in FIG. 19, "M" represents Mesalazine® used as a positive control drug. As illustrated in FIG. 19, the combined extract composed of the fraction of the *Anemarrhena asphodeloides* Bunge extract and the fraction of the *Coptis chinensis* extract and the combined extract composed of the fraction of the *Anemarrhena asphodeloides* Bunge extract, the fraction of the *Galla Rhois* extract, and the fraction of the *Codonopsis lanceolate* extract suppressed the expressions of COX-2, iNOS, p-p65 (phosphor-NF-Kappa B), and the like, in a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolate* extract.

8. Measurement of Effect of Treating Colitis in Experimental Model Animals with Chronic Colitis Induced by Oxazolone.

(1) Preparation of Experimental Animal.

6-week old male mice (C57BL/6, 18 g to 22 g) were purchased from OrientBio Inc. All the mice were bred under the controlled environmental conditions of 50±10% of humidity at a temperature of 20° C. to 22° C., and the lighting was provided by repeatedly turning on for 12 hours followed by turning off for 12 hours. A feed for a standard experiment (Samyang, Korea) was used as a feed, and ad libitum access to water was allowed. In all experiments, each group consisted of 6 mice.

(2) Induction of Chronic Colitis by Oxazolone and Sample Administration.

Among the experimental groups, one group was set as a normal group, and the experimental animals in other groups were induced with chronic colitis by oxazolone. In detail, the hairs on the mice were removed, and 0.2 mL of 3% (w/v) oxazolone solution was applied on the area of about 1.5 cm×1.5 cm for sensitization. After 8 days, the mice were anesthetized, and 0.1 mL of 1% oxazolone solution was administered into the colons through rectum. From the following day, the drug sample dissolved in normal saline solution was orally administered at the predetermined once daily for 15 days. On the following day after completing the sample administration, the experimental animals were suffocated to death with carbon dioxide, and the colon from the appendix to the region immediately before the anus was removed from the colon region.

(3) Measurements of Weight Change of Model Animal, Colon Appearance, and Myeloperoxidase (MPO) Activity.

1) Analysis of Weight Change Amount.

The amount of weight change was analyzed in the same manner as in the experiment for model animals with colitis induced by TNBS.

2) Appearance Analysis.

The appearance of colon was analyzed in the same manner as in the experiment for model animals with colitis induced by TNBS.

3) Measurement of MPO Activity.

The myeloperoxidase (MPO) activity was measured in the same manner as in the experiment for model animals with colitis induced by TNBS.

4) Results of the Measurements of the Amount of Weight Change, Appearance of Colon, Colon Length, and MPO Activity.

Figure 20:
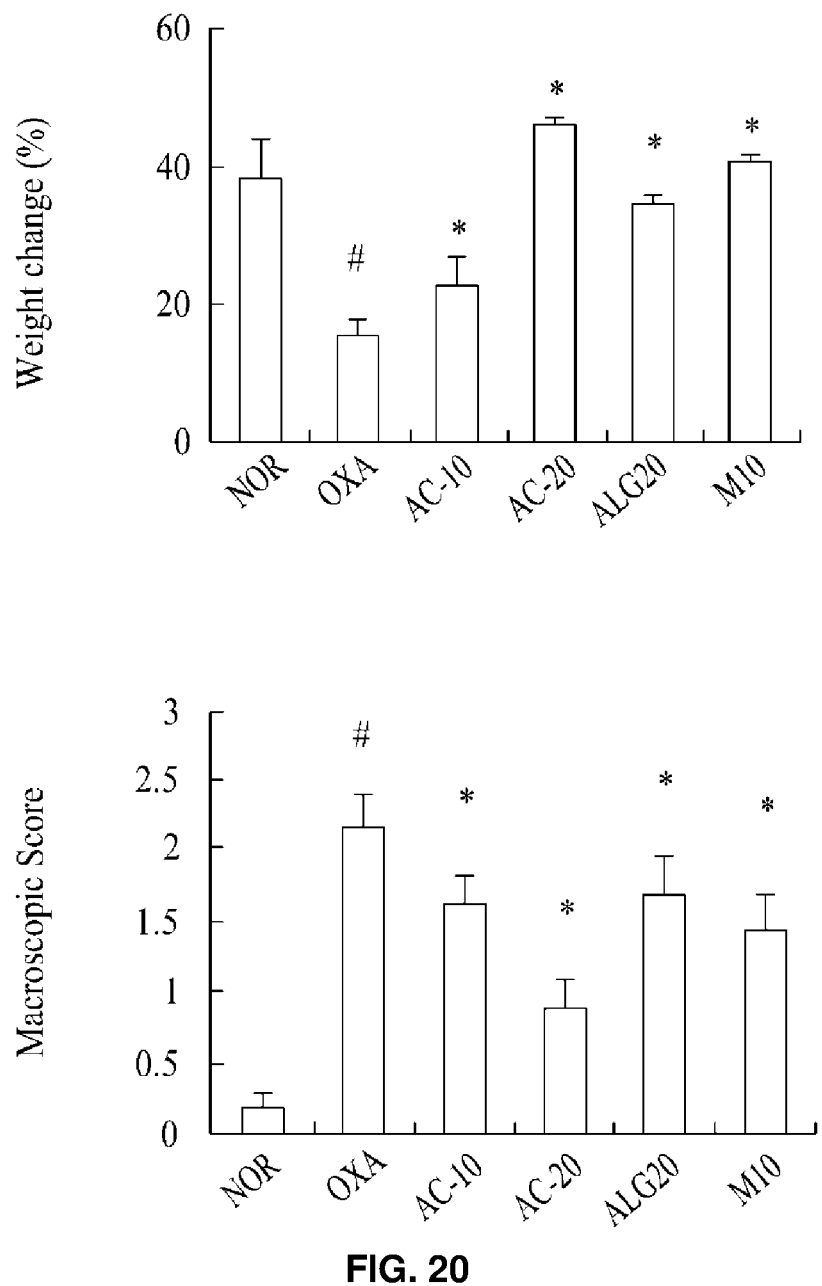
FIG. 20 illustrates graphs respectively illustrating the weight change and the score on external appearance of colon in model animals induced with chronic colitis by oxazolone when the combined extract was used as a drug sample.
Figure 21:
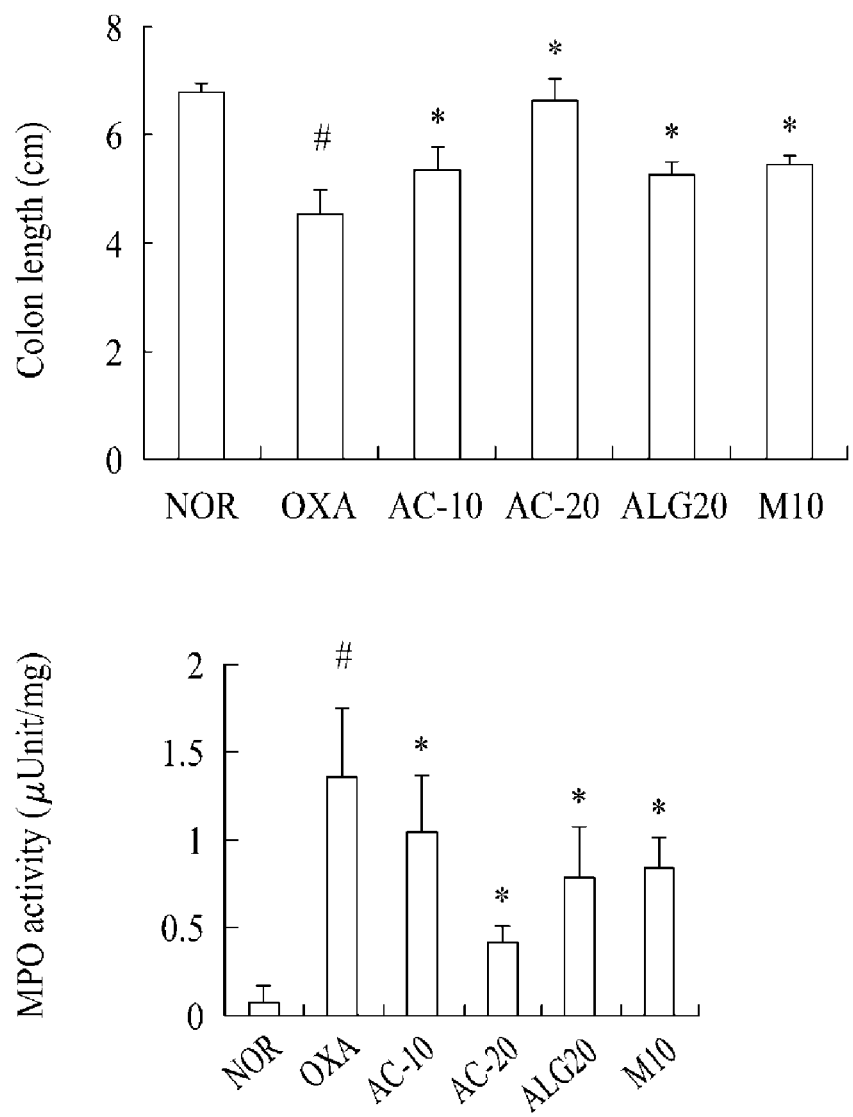
FIG. 21 illustrates the results of the colon length and the MPO activity measured in model animals induced with chronic colitis by oxazolone when the combined extract were used as a drug sample.

FIG. 20 illustrates graphs respectively illustrating the weight change and the score on external appearance of colon in model animals induced with chronic colitis by oxazolone when the combined extract was used as a drug sample, and FIG. 21 illustrates the results of the colon length and the MPO activity measured in model animals induced with chronic colitis by oxazolone when the combined extract were used as a drug sample. In FIGS. 20 and 21, "NOR" represents a normal group, "OXA" represents the experimental group that was orally administered only with normal saline solution after inducing chronic colitis with oxazolone, "AC" represents the combined extract prepared in Preparation Example 13, and "ALG" represents the combined extract prepared in Preparation Example 12. Additionally, "AC-10" and "AC-20" respectively represent 10 mg/mouse kg and 20 mg/mouse kg as a unit dose of "AC" that is a drug sample. Additionally, in FIGS. 20 and 21, "M" represents Mesalazine® used as a positive control drug. As illustrated in FIGS. 20 and 21, the combined extract composed of the fraction of the *Anemarrhena asphodeloides* Bunge extract and the fraction of the *Coptis chinensis* extract and the combined extract composed of the fraction of the *Anemarrhena asphodeloides* Bunge extract, the fraction of the *Galla Rhois* extract, and the fraction of the *Codonopsis lanceolata* extract exhibited the effect of suppressing chronic colitis in a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolata* extract.

(4) Analysis of Effect on Expression of Inflammatory Marker Substances.

1) Effect on Expression of Proinflammatory Cytokines and Anti-Inflammatory Cytokines.

The expression amount of proinflammatory cytokines and anti-inflammatory cytokines in the colon tissues of model animals with chronic colitis induced by oxazolone, when administered with a drug sample, was measured in the same manner as in the experiment for model animals with colitis induced by TNBS.

Figure 22:
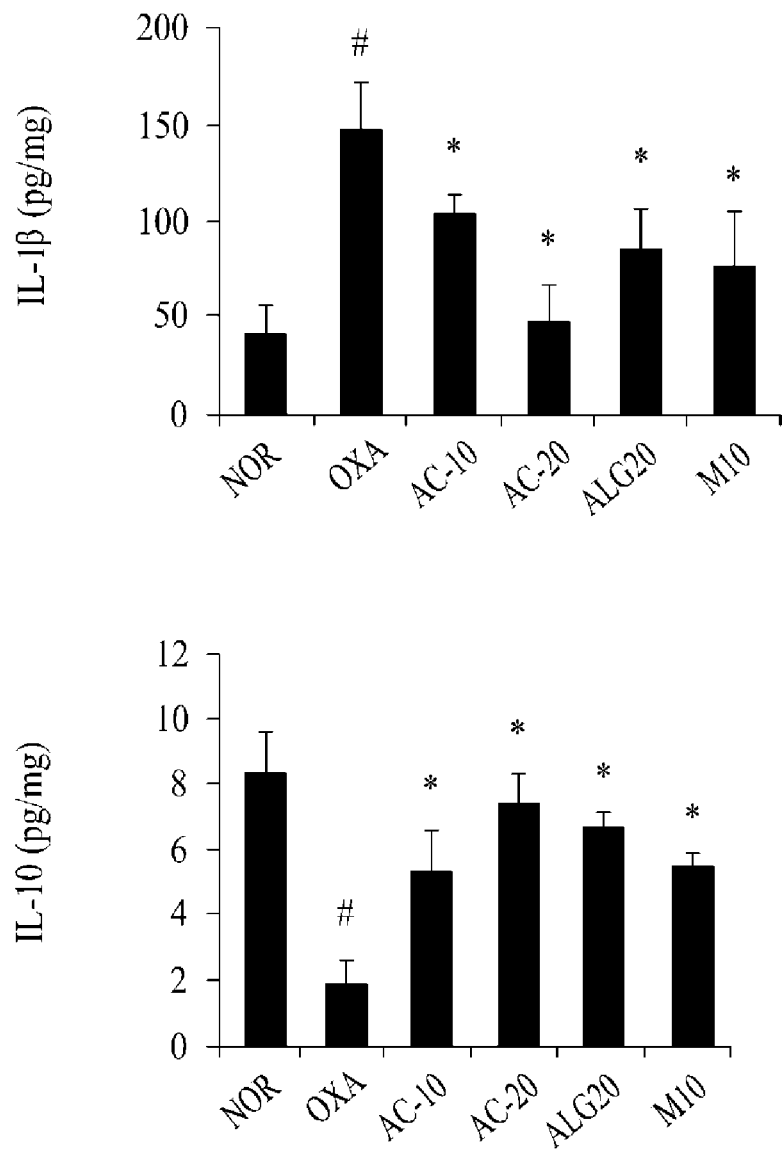
FIG. 22 illustrates graphs respectively illustrating the expression amount of IL-1β and IL-10 in colon tissues of model animals induced with chronic colitis by oxazolone when the combined extract was used as a drug sample.
Figure 23:
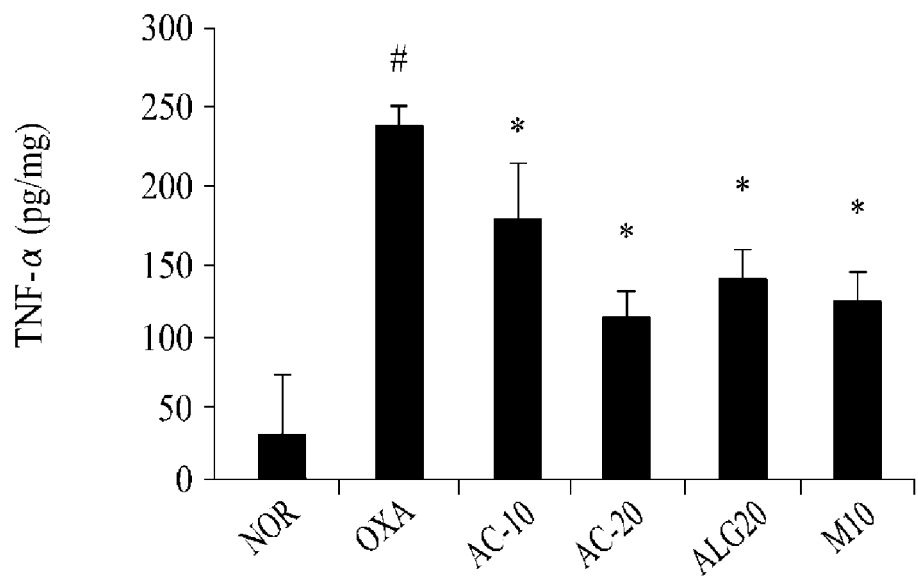
FIG. 23 illustrates graphs respectively illustrating the expression amount of TNF-α and IL-6 in colon tissues of model animals induced with chronic colitis by oxazolone when the combined extract was used as a drug sample.
Figure 23:
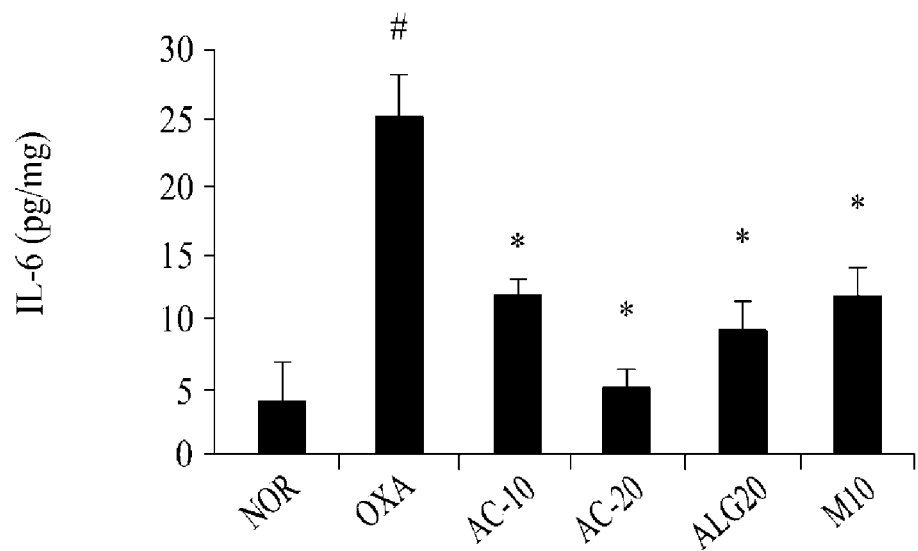

FIG. 22 illustrates graphs respectively illustrating the expression amount of IL-1β and IL-10 in colon tissues of model animals induced with chronic colitis by oxazolone when the combined extract was used as a drug sample, and FIG. 23 illustrates graphs respectively illustrating the expression amount of TNF-α and IL-6 in colon tissues of model animals induced with chronic colitis by oxazolone when the combined extract was used as a drug sample. In FIGS. 22 and 23, "NOR" represents a normal group, "OXA" represents the experimental group that was orally administered only with normal saline solution after inducing chronic colitis with oxazolone, "AC" represents the combined extract prepared in Preparation Example 13, and "ALG" represents the combined extract prepared in Preparation Example 12. Additionally, "AC-10" and "AC-20" respectively represent 10 mg/mouse kg and 20 mg/mouse kg as a unit dose of "AC", which is a drug sample. Additionally, in FIGS. 22 and 23, "M" represents Mesalazine® used as a positive control drug. As illustrated in FIGS. 22 and 23, the combined extract composed of the fraction of the *Anemarrhena asphodeloides* Bunge extract and the fraction of the *Coptis chinensis* extract and the combined extract composed of the fraction of the *Anemarrhena asphodeloides* Bunge extract, the fraction of the *Galla Rhois* extract, and the fraction of the *Codonopsis lanceolate* extract decreased the expressions of proinflammatory cytokines while increasing the expressions of anti-inflammatory cytokines to be increased to a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolate* extract.

2) Presence of Inhibition on Expression of Inflammatory Marker Substances.

The expression amount of COX-2, iNOS, p65 (NF-Kappa B), p-p65 (phosphor-NF-Kappa B), and β-actin in the colon tissues of model animals with chronic colitis induced by oxazolone, when administered with a drug sample, was measured in the same manner as in the experiment for model animals with colitis induced by TNBS.

Figure 24:
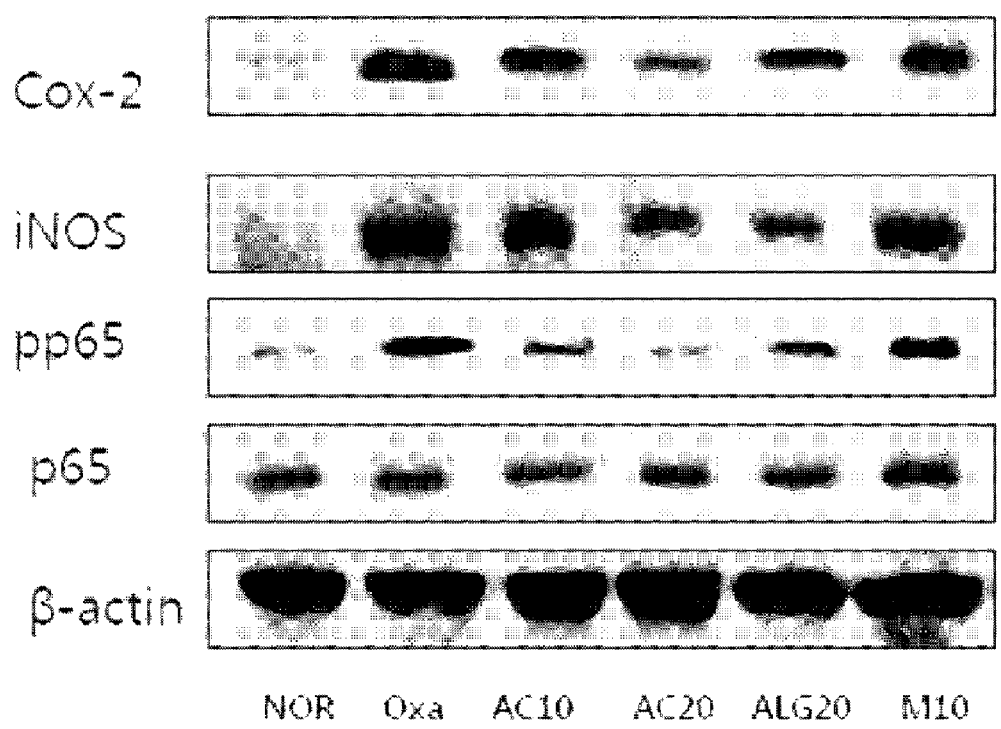
FIG. 24 illustrates the results of inhibition of inflammatory marker substance expression in colon tissues of model animals induced with chronic colitis by oxazolone when the model animals were administered with a combined extract.

FIG. 24 illustrates the results of inhibition of inflammatory marker substance expression in colon tissues of model animals induced with chronic colitis by oxazolone when the model animals were administered with a combined extract. In FIG. 24, "NOR" represents a normal group, "Oxa" represents the experimental group that was orally administered only with normal saline solution after inducing chronic colitis with oxazolone, "AC" represents the combined extract prepared in Preparation Example 13, and "ALG" represents the combined extract prepared in Preparation Example 12. Additionally, "AC10" and "AC20" respectively represent 10 mg/mouse kg and 20 mg/mouse kg as a unit dose of "AC", which is a drug sample. Additionally, in FIG. 24, "M" represents Mesalazine® used as a positive control drug. As illustrated in FIG. 24, the combined extract composed of the fraction of the *Anemarrhena asphodeloides* Bunge extract and the fraction of the *Coptis chinensis* extract and the combined extract composed of the fraction of the *Anemarrhena asphodeloides* Bunge extract, the fraction of the *Galla Rhois* extract, and the fraction of the *Codonopsis lanceolate* extract suppressed the expressions of COX-2, iNOS, p-p65 (phosphor-NF-Kappa B), and the like, to a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolate* extract.

9. Measurement of Effect of Treating Colitis in Experimental Model Animals with Chronic Colitis Induced by DSS.

(1) Preparation of Experimental Animal.

6-week old male mice (C57BL/6, 18 g to 22 g) were purchased from OrientBio Inc. All the mice were bred under the controlled environmental conditions of 50±10% of humidity at a temperature of 20° C. to 22° C., and the lighting was provided by repeatedly turning on for 12 hours followed by turning off for 12 hours. A feed for a standard experiment (Samyang, Korea) was used as a feed, and ad libitum access to water was allowed. In all experiments, each group consisted of 6 mice.

(2) Induction of Chronic Colitis by DSS and Sample Administration.

Among the experimental groups, one group was set as a normal group, and the experimental animals in other groups were induced with chronic colitis by dextran sulfate sodium (molecular weight: 36 kDaltons to 50 kDaltons). In detail, the animal models with chronic colitis were firstly prepared by feeding with a 3% (w/v) aqueous dextran sulfate sodium solution for 7 days instead of water as drinking water; again by feeding with water for 5 days; secondly by feeding with a 3% (w/v) aqueous dextran sulfate sodium solution for 3 days; and by feeding with water for 3 days as drinking water. Meanwhile, the normal group was fed with water as drinking water. Additionally, from the day that secondly started feeding with the aqueous dextran sulfate sodium solution, the sample dissolved in normal saline solution was orally administered at the predetermined volume once a day. On the following day after completing the sample administration, the experimental animals were suffocated to death with carbon dioxide, and the colon from the appendix to the region immediately before the anus was removed from the colon region.

(3) Measurements of Weight Change of Model Animals, Colon Appearance, and Myeloperoxidase (MPO) Activity.

1) Analysis of Amount of Weight Change.

The amount of weight change was analyzed in the same manner as in the experiment for model animals with colitis induced by TNBS.

2) Analysis of Appearances.

The appearance of colon was analyzed in the same manner as in the experiment for model animals with colitis induced by TNBS.

3) Measurement of MPO Activity.

The myeloperoxidase (MPO) activity was measured in the same manner as in the experiment for model animals with colitis induced by TNBS.

4) Results of Measuring Amount of Weight Change, Appearance of Colon, Colon Length, and MPO Activity.

Figure 25:
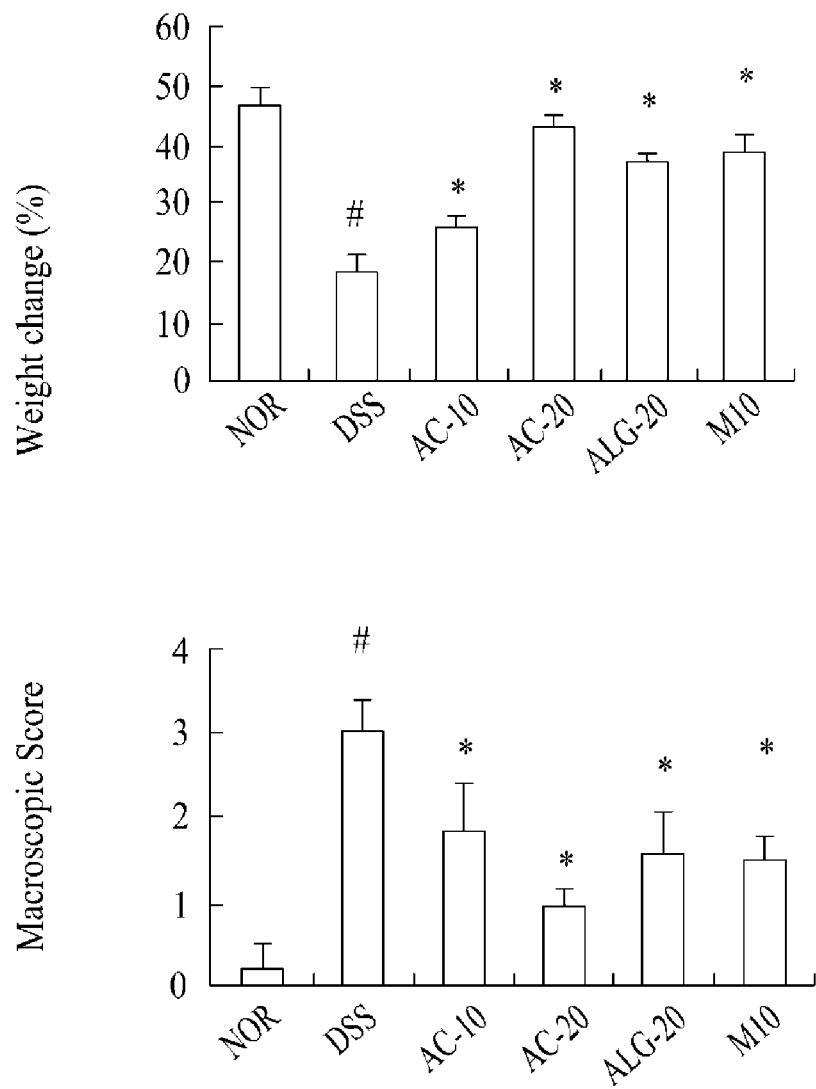
FIG. 25 illustrates graphs respectively illustrating the weight change and the score on external appearance of colon in model animals induced with chronic colitis by DSS when the combined extract was used as a drug sample.
Figure 26:
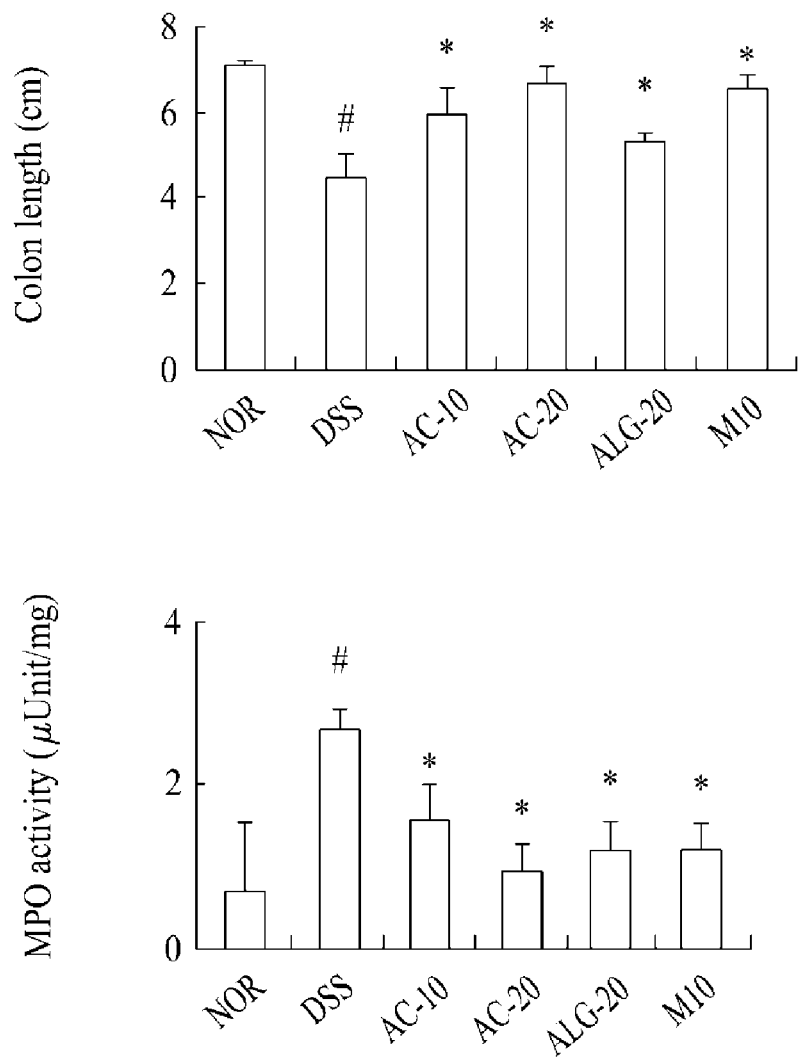
FIG. 26 illustrates the results of the colon length and the MPO activity measured in model animals induced with chronic colitis by DSS when the combined extract was used as a drug sample.

FIG. 25 illustrates graphs respectively illustrating the weight change and the score on external appearance of colon in model animals induced with chronic colitis by DSS when the combined extract was used as a drug sample, and FIG. 26 illustrates the results of the colon length and the MPO activity measured in model animals induced with chronic colitis by DSS when the combined extract was used as a drug sample. In FIGS. 25 and 26, "NOR" represents a normal group, "AC" represents the combined extract prepared in Preparation Example 13, and "ALG" represents the combined extract prepared in Preparation Example 12. Additionally, "AC-10" and "AC-20" respectively represent 10 mg/mouse kg and 20 mg/mouse kg as a unit dose of "AC", which is a drug sample. Additionally, in FIGS. 25 and 26, "M" represents Mesalazine® used as a positive control drug. As illustrated in FIGS. 25 and 26, the combined extract composed of the fraction of the *Anemarrhena asphodeloides* Bunge extract and the fraction of the *Coptis chinensis* extract and the combined extract composed of the fraction of the *Anemarrhena asphodeloides* Bunge extract, the fraction of the *Galla Rhois* extract, and the fraction of the *Codonopsis lanceolata* extract suppressed chronic colitis to a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolata* extract.

(4) Analysis of Effect on Expressions of Inflammation Marker Substances.

1) Effect on Expressions of Proinflammatory Cytokine and Anti-Inflammatory Cytokine.

The expression amount of proinflammatory cytokines and anti-inflammatory cytokines in colon tissues of model animals with chronic colitis induced by DSS, when administered with a drug sample, was measured in the same manner as in the experiment for the model animals with colitis induced by TNBS.

Figure 27:
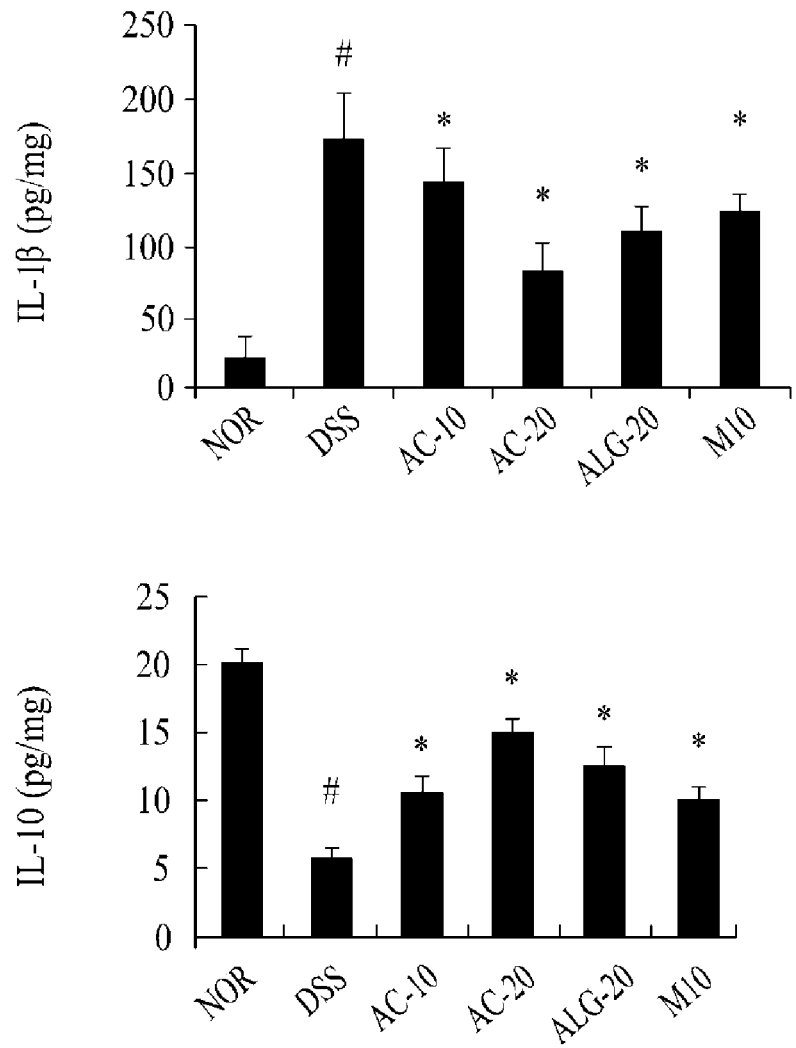
FIG. 27 illustrates graphs respectively illustrating the expression amount of IL-1β and IL-10 in colon tissues of model animals induced with chronic colitis by DSS when the combined extract was used as a drug sample.
Figure 28:
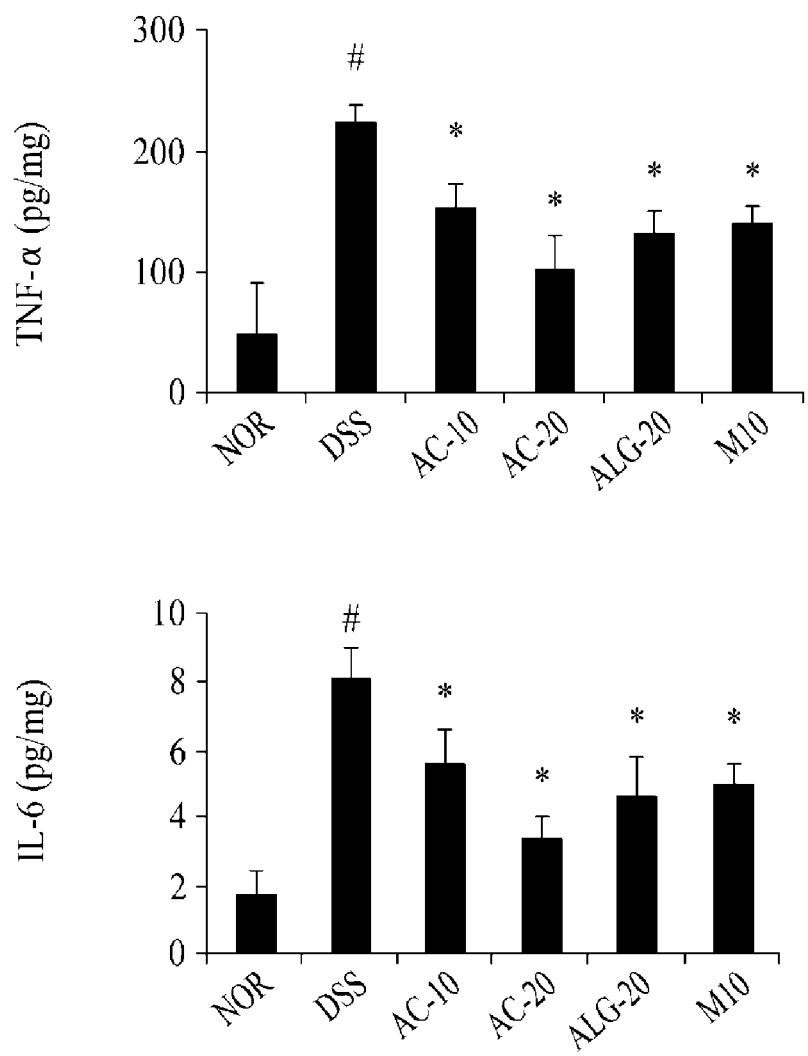
FIG. 28 illustrates graphs respectively illustrating the expression amount of TNF-α and IL-6 in colon tissues of model animals induced with chronic colitis by DSS when the combined extract was used as a drug sample.

FIG. 27 illustrates graphs respectively illustrating the expression amount of IL-1β and IL-10 in colon tissues of model animals induced with chronic colitis by DSS when the combined extract was used as a drug sample, and FIG. 28 illustrates graphs respectively illustrating the expression amount of TNF-α and IL-6 in colon tissues of model animals induced with chronic colitis by DSS when the combined extract was used as a drug sample. In FIGS. 27 and 28, "NOR" represents a normal group, "AC" represents the combined extract prepared in Preparation Example 13, and "ALG" represents the combined extract prepared in Preparation Example 12. Additionally, "AC-10" and "AC-20" respectively represent 10 mg/mouse kg and 20 mg/mouse kg as a unit dose of "AC", which is a drug sample. Additionally, in FIGS. 27 and 28, "M" represents Mesalazine® used as a positive control drug. As illustrated in FIGS. 27 and 28, the combined extract composed of the fraction of the *Anemarrhena asphodeloides* Bunge extract and the fraction of the

*Coptis chinensis* extract and the combined extract composed of the fraction of the *Anemarrhena asphodeloides* Bunge extract, the fraction of the *Galla Rhois* extract, and the fraction of the *Codonopsis lanceolate* extract decreased the expressions of proinflammatory cytokines while increasing the expressions of anti-inflammatory cytokines to a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolate* extract.

2) Presence of Inhibition on Expression of Inflammatory Marker Substances

The expression amount of COX-2, iNOS, p65 (NF-Kappa B), p-p65 (phosphor-NF-Kappa B), and β-actin in the colon tissues of model animals with chronic colitis induced by DSS, when administered with a drug sample, was measured in the same manner as in the experiment for model animals with colitis induced by TNBS.

Figure 29:
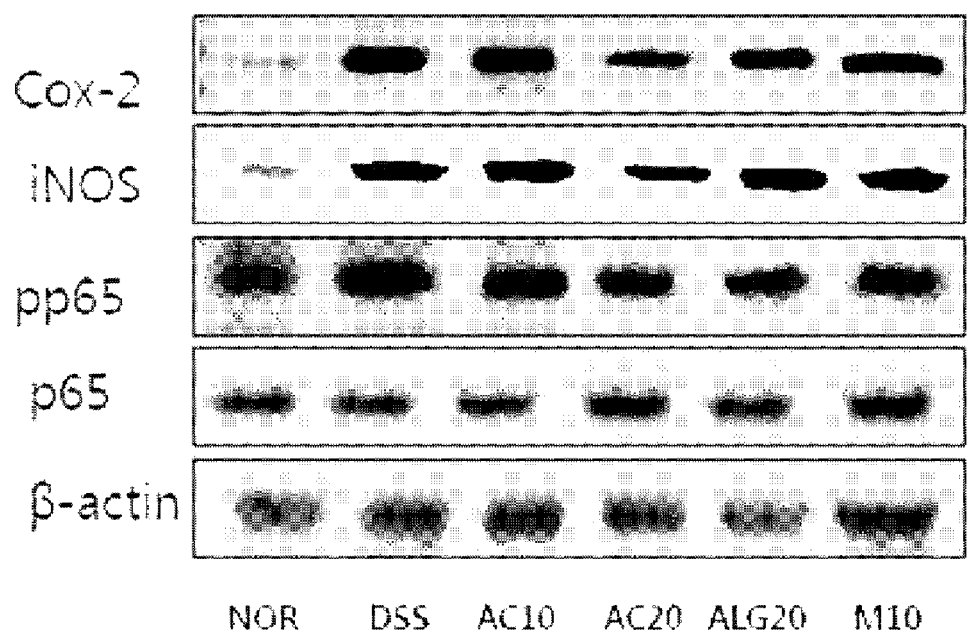
FIG. 29 illustrates the results of inhibition of inflammatory marker substance expression in colon tissues of model animals induced with chronic colitis by DSS when the model animals were administered with a combined extract.

FIG. 29 illustrates the results of inhibition of inflammatory marker substance expression in colon tissues of model animals induced with chronic colitis by DSS when the model animals were administered with a combined extract. In FIG. 29, "NOR" represents a normal group, "AC" represents the combined extract prepared in Preparation Example 13, and "ALG" represents the combined extract prepared in Preparation Example 12. Additionally, "AC10" and "AC20" respectively represent 10 mg/mouse kg and 20 mg/mouse kg as a unit dose of "AC", which is a drug sample. Additionally, in FIG. 29, "M" represents Mesalazine® used as a positive control drug. As illustrated in FIG. 29, the combined extract composed of the fraction of the *Anemarrhena asphodeloides* Bunge extract and the fraction of the *Coptis chinensis* extract and the combined extract composed of the fraction of the *Anemarrhena asphodeloides* Bunge extract, the fraction of the *Galla Rhois* extract, and the fraction of the *Codonopsis lanceolata* extract suppressed the expressions of COX-2, iNOS, p-p65 (phosphor-NF-Kappa B), and the like, to a level similar to that of Mesalazine®, which was used as a positive control drug. Specifically, the combined extract of the fraction of the *Anemarrhena asphodeloides* Bunge extract and the fraction of the *Coptis chinensis* extract exhibited more excellent effect, compared with the combined extract composed of the fraction of the *Anemarrhena asphodeloides* Bunge extract, the fraction of the *Galla Rhois* extract, and the fraction of the *Codonopsis lanceolata* extract.

II. Secondary Experiment for Confirmation of the Effects of an *Anemarrhena asphodeloides* Bunge Extract, and the like, and a Rhizoma Coptidis Extract, and the like, and a Combined Use Thereof for Preventing or Treating Colitis.

10. Preparation of an *Anemarrhena asphodeloides* Bunge Extract and a Fraction Thereof.

Preparation Example 14: Preparation of an Ethanol Extract of *Anemarrhena asphodeloides* Bunge.

After adding 2 L of an 80% aqueous ethanol solution to 500 g of *Anemarrhena asphodeloides* Bunge, the mixture was subjected to an extraction process in a water bath for about 2 hours, and then filtered. Additionally, the remaining residue was subjected to a re-extraction under the same condition after adding 2 L of the same solvent thereto and filtered. The filtered liquid extract was concentrated under reduced pressure and freeze-dried to obtain 158 g of an *Anemarrhena asphodeloides* Bunge extract.

Preparation Example 15: Preparation of a Water Extract of *Anemarrhena asphodeloides* Bunge.

After adding 2.5 L of distilled water to 500 g of *Anemarrhena asphodeloides* Bunge, the mixture was subjected to an extraction process in a water bath for about 2 hours, and then filtered. Additionally, the remaining residue was subjected to a re-extraction under the same condition after adding 2 L of the distilled water thereto and filtered. The filtered liquid extract was concentrated under reduced pressure and freeze-dried to obtain 164 g of a water extract of *Anemarrhena asphodeloides* Bunge.

Preparation Example 16: Preparation of a Butanol-Soluble Fraction from an Ethanol Extract of *Anemarrhena asphodeloides* Bunge.

After suspending 158 g of the ethanol extract of *Anemarrhena asphodeloides* Bunge obtained in Preparation Example 14 in 1.5 L of water, 1.5 L of n-butanol was added thereto, and the resultant was placed in a shaking bath to separate an n-butanol-soluble fraction layer and a water-soluble fraction layer therefrom. The n-butanol-soluble fraction layer was collected, concentrated under reduced pressure, and freeze-dried to obtain 42 g of the n-butanol-soluble fraction. The yield of the n-butanol-soluble fraction was 8.4% or higher based on the *Anemarrhena asphodeloides* Bunge.

11. Preparation of an Ethanol Extract of *Coptis chinensis* and a Fraction Thereof.

Preparation Example 17: Preparation of an Ethanol Extract of *Coptis chinensis*.

After adding 2.5 L of an 80% aqueous ethanol solution to 500 g of dried root of *Coptis chinensis* (Kyoung Dong Market, Seoul, Korea), the mixture was subjected to an extraction process in a water bath for about 2 hours, and then filtered. Additionally, the remaining residue was subjected to a re-extraction under the same condition after adding 2 L of the same solvent there to and filtered. The filtered liquid extract was concentrated under reduced pressure and freeze-dried to obtain 107 g of an ethanol extract of *Coptis chinensis*.

Preparation Example 18: Preparation of a Water Extract of *Coptis chinensis*.

After adding 2.5 L of distilled water to 500 g of dried root of *Coptis chinensis* (Kyoung Dong Market, Seoul, Korea), the mixture was subjected to an extraction process in a water bath for about 2 hours, and then filtered. Additionally, the remaining residue was subjected to a re-extraction under the same condition after adding 2 L of the distilled water there to and filtered. The filtered liquid extract was concentrated under reduced pressure and freeze-dried to obtain 122 g of a water extract of *Coptis chinensis*.

Preparation Example 19: Preparation of a Butanol-Soluble Fraction from an Ethanol Extract of *Coptis chinensis*.

After suspending 107 g of the ethanol extract of *Anemarrhena asphodeloides* Bunge obtained in Preparation Example 17 in 1.5 L of water, 1.5 L of n-butanol was added thereto, and the resultant was placed in a shaking bath to separate an n-butanol-soluble fraction layer and a water-soluble fraction layer therefrom. The n-butanol-soluble fraction layer was collected, concentrated under reduced pressure, and freeze-dried to obtain 64 g of the n-butanol-soluble fraction. The yield of the n-butanol-soluble fraction was 12.8% or higher based on the *Coptis chinensis*.

12. Preparation of a Combined Extract.

Preparation Example 20.

A combined extract was prepared by mixing the ethanol extract of *Anemarrhena asphodeloides* Bunge prepared in Preparation Example 14 and the ethanol extract of *Coptis chinensis* prepared in Preparation Example 17 at a weight ratio of 1:3.

Preparation Example 21.

A combined extract was prepared by mixing the ethanol extract of *Anemarrhena asphodeloides* Bunge prepared in Preparation Example 14 and the ethanol extract of *Coptis chinensis* prepared in Preparation Example 17 at a weight ratio of 1:1.

Preparation Example 22.

A combined extract was prepared by mixing the ethanol extract of *Anemarrhena asphodeloides* Bunge prepared in Preparation Example 14 and the ethanol extract of *Coptis chinensis* prepared in Preparation Example 17 at a weight ratio of 3:1.

Preparation Example 23.

A combined extract was prepared by mixing the ethanol extract of *Anemarrhena asphodeloides* Bunge prepared in Preparation Example 14 and the ethanol extract of *Coptis chinensis* prepared in Preparation Example 17 at a weight ratio of 5:1.

Preparation Example 24.

A combined extract was prepared by mixing the ethanol extract of *Anemarrhena asphodeloides* Bunge prepared in Preparation Example 14 and the ethanol extract of *Coptis chinensis* prepared in Preparation Example 17 at a weight ratio of 7:1.

Preparation Example 25.

A combined extract was prepared by mixing the ethanol extract of *Anemarrhena asphodeloides* Bunge prepared in Preparation Example 14 and the ethanol extract of *Coptis chinensis* prepared in Preparation Example 17 at a weight ratio of 10:1.

Preparation Example 26.

A combined extract was prepared by mixing the water extract of *Anemarrhena asphodeloides* Bunge prepared in Preparation Example 15 and the water extract of *Coptis chinensis* prepared in Preparation Example 18 at a weight ratio of 1:1.

Preparation Example 27.

A combined extract was prepared by mixing the butanol-soluble fraction of the ethanol extract of *Anemarrhena asphodeloides* Bunge prepared in Preparation Example 16 and the butanol-soluble fraction of the ethanol extract of *Coptis chinensis* prepared in Preparation Example 19 at a weight ratio of 1:3.

Preparation Example 28.

A combined extract was prepared by mixing the butanol-soluble fraction of the ethanol extract of *Anemarrhena asphodeloides* Bunge prepared in Preparation Example 16 and the butanol-soluble fraction of the ethanol extract of *Coptis chinensis* prepared in Preparation Example 19 at a weight ratio of 1:1.

Preparation Example 29.

A combined extract was prepared by mixing the butanol-soluble fraction of the ethanol extract of *Anemarrhena asphodeloides* Bunge prepared in Preparation Example 16 and the butanol-soluble fraction of the ethanol extract of *Coptis chinensis* prepared in Preparation Example 19 at a weight ratio of 3:1.

Preparation Example 30.

A combined extract was prepared by mixing the butanol-soluble fraction of the ethanol extract of *Anemarrhena asphodeloides* Bunge prepared in Preparation Example 16 and the butanol-soluble fraction of the ethanol extract of *Coptis chinensis* prepared in Preparation Example 19 at a weight ratio of 5:1.

Preparation Example 31.

A combined extract was prepared by mixing the butanol-soluble fraction of the ethanol extract of *Anemarrhena asphodeloides* Bunge prepared in Preparation Example 16 and the butanol-soluble fraction of the ethanol extract of *Coptis chinensis* prepared in Preparation Example 19 at a weight ratio of 7:1.

Preparation Example 32.

A combined extract was prepared by mixing the butanol-soluble fraction of the ethanol extract of *Anemarrhena asphodeloides* Bunge prepared in Preparation Example 16 and the butanol-soluble fraction of the ethanol extract of *Coptis chinensis* prepared in Preparation Example 19 at a weight ratio of 10:1.

13. Measurement of Effects of Treating Colitis in Experiments of Model Animals with Acute Colitis Induced by TNBS.

(1) Preparation of Experimental Animals.

6-week old male mice (C57BL/6, 18 g to 22 g) were purchased from OrientBio Inc. All the mice were bred under the controlled environmental conditions of 50±10% of humidity at a temperature of 20° C. to 22° C., and the lighting was provided by repeatedly turning on for 12 hours followed by turning off for 12 hours. A feed for a standard experiment (Samyang, Korea) was used as a feed, and ad libitum access to water was allowed. In all experiments, each group consisted of 6 mice.

(2) Induction of Acute Colitis by TNBS and Sample Administration.

Among the experimental groups, one group was set as a normal group, and the experimental animals in other groups were induced with acute colitis by 2,4,6-trinitrobenzenesulfonic acid (TNBS). In detail, after lightly anesthetizing the experimental animals with ether, 0.1 mL of the solution prepared by mixing 2.5 g of 2,4,6-Trinitrobenzene sulfonic acid (NBS) solution with 50% ethanol was injected into the colon through the anus using a syringe having 1 mL volume and an oval point, respectively; the syringe was vertically picked up, and then, maintained for 30 seconds to induce inflammation. Meanwhile, for the normal group, 0.1 mL of normal saline solution was orally administered. Subsequently, from the following day, the sample dissolved in normal saline solution was orally administered at a predetermined volume once daily for 3 days. On the following day after completing the sample administration, the experimental animals were suffocated to death with carbon dioxide, and the colon from the appendix to the region immediately before the anus was removed from the colon region. In this case, the experiments, where an ethanol extract of *Anemarrhena asphodeloides* Bunge, an ethanol extract of *Coptis chinensis*, a combined extract of the ethanol extract of *Anemarrhena asphodeloides* Bunge and the ethanol extract of *Coptis chinensis*, and a combined extract of a water extract of *Anemarrhena asphodeloides* Bunge and a water extract of *Coptis chinensis* were used as drug samples (hereinafter, "extract-based experiment"), and the experiments, where a butanol-soluble fraction of the ethanol extract of *Anemarrhena asphodeloides* Bunge, a butanol-soluble fraction of the ethanol extract of *Coptis chinensis*, and a combined extract of the butanol-soluble fraction of the ethanol extract of *Anemarrhena asphodeloides* Bunge and the butanol-soluble fraction of the ethanol extract of *Coptis chinensis* were used as drug samples (hereinafter, "fraction-based experiment") were separately performed with time intervals, respectively. Considering the characteristics of animal experiments, it is reasonable that the effects of the drug samples on preventing or treating colitis be evaluated within each of the experiments and that the normal group supplied with saline solution instead of a specific drug sample, for the experimental animals not treated with TNBS, be used as a standard.

(3) Measurements of Weight Change, Appearance of Colon and Myeloperoxidase (MPO) Activity.

1) Analysis of the Amount of Weight Change.

The sample administration to the model animals with colitis induced by TNBS was stopped, and on the following day, the weight of the experimental animals was measured were and then compared with their initial weight to calculate the change in the amount of weight.

2) Analysis of Appearances

The scores on the removed colons were estimated by observing the appearances and the length of the colons according to the criteria (Hollenbach et al., the criteria on the levels of colon in 2005) listed in Table 3. In this case, as a positive control group, the group administered with Mesalazine® (Sigma) was used. Additionally, a portion of the content in the colon was collected to analyze the intestinal microorganisms, and then stored in a freezer maintained at −80° C. From the tissues of colon, the content in the colon was completely removed and then the tissues of colon were washed with normal saline solution. Then, some of the tissues were fixed with 4% formaldehyde fixing solution in order to use them as samples for histopathological examination, and the rest was stored in a freezer maintained at −80° C. for molecular biological analysis.

TABLE 3

| Macroscopic score | Criteria |
| --- | --- |
| 0 | Presence of no ulcer and no inflammation |
| 1 | Presence of hyperemia without blood |
| 2 | Presence of ulcer with hyperemia |
| 3 | Presence of ulcer and inflammation only in one region |
| 4 | Presence of ulcer and inflammation in two or more regions |
| 5 | Presence of enlarged ulcer by 2 cm or more |

3) Myeloperoxidase (MPO) Activity Measurement 100 mg of colon tissues were homogenized after adding 200 μL of lysis buffer thereto. The homogenized colon tissues were centrifuged at 4° C. at a rate of 13000 rpm for 15 minutes, the supernatant therefrom was recovered, and the MPO activity was measured using a mouse MPO assay ELISA kit (Hbt HK210, USA). 100 μL of the supernatant was added into a 96-well plate and reacted at room temperature for 1 hour. Upon completion of the reaction, the plate was emptied by overturning, repeatedly washed three times with 200 μL of washing buffer, added with 100 μL of diluted tracer, and then the reaction was allowed to perform at room temperature for 1 hour. Upon completion of the reaction, the plate was emptied by overturning, and each well of the plate was washed using 200 μL of washing buffer. After repeatedly performing the washing process three times using 200 μL of washing buffer, 100 μL of diluted streptavidin-peroxidase conjugate was added thereto, and the reaction was allowed to perform at room temperature for 1 hour. Upon completion of the reaction, the plate was emptied by overturning, and each well of the plate was washed with 200 μL of washing buffer. After repeatedly washing three times using 200 μL of washing buffer, 100 μL of TMB substrate solution was added thereto, the plate was wrapped with an aluminum foil to block out the light, and the reaction was performed at room temperature for 30 minutes. Subsequently, 100 μL of a stop solution was added to terminate the reaction, and the absorbance was measured at 450 nm using an ELISA reader.

4) Results of the Measurements of the Amount of Weight Change, Appearances of Colon, Length of Colon, and MPO Activity Table 4 below lists the summary of the results of the extract-based experiments of model animals with acute colitis induced by TNBS. In the following Table 4, the values of analyzed item are represented as a percentage to the value of the normal group supplied with saline solution instead of the specific drug sample in the model animals not treated with TNBS.

As listed in the following Table 4, the administration of the combined extract, which was prepared by mixing the ethanol extract of Anemarrhena asphodeloides Bunge and the ethanol extract of Coptis chinensis, showed an improved anti-colitis effect in animal models with acute colitis induced by TNBS, compared with when the ethanol extract of Anemarrhena asphodeloides Bunge or the ethanol extract of Coptis chinensis was administered alone. Additionally, the anti-colitis effect of the combined extracts prepared by mixing the ethanol extract of Anemarrhena asphodeloides Bunge and the ethanol extract of Coptis chinensis was most significantly increased when the weight ratio between the ethanol extract of Anemarrhena asphodeloides Bunge and the ethanol extract of Coptis chinensis was 3:1, followed by 5:1 and 1:1, in this order. Additionally, based on the same amount of administration, the combined extract, which was prepared by mixing the ethanol extract of Anemarrhena asphodeloides Bunge and the ethanol extract of Coptis chinensis, exhibited a higher anti-colitis effect than Mesalazine®, which is currently used as a therapeutic drug for colitis.

TABLE 4

| Experimental Groups | | Unit dose of drug sample (mg/kg) | Values of analyzed items (Percentage to normal group supplied with saline solution without TNBS treatment, %) | | | |
| --- | --- | --- | --- | --- | --- | --- |
| Presence of TNBS treatment | Drug sample for administration | | Body weight | Colon length | Macroscopic score | MPO activity |
| − | vehicle | — | 100 | 100 | 100 | 100 |
| + | vehicle | — | −89.3 | 75 | 950 | 1180 |
| + | Prep. Ex. 14 | 20 | 71.43 | 87.5 | 475 | 420 |
| + | Prep. Ex. 20 | 20 | 67.86 | 93.65 | 434 | 420 |
| + | Prep. Ex. 21 | 20 | 82.14 | 95.31 | 300 | 280 |
| + | Prep. Ex. 22 | 20 | 85.71 | 98.44 | 225 | 180 |
| + | Prep. Ex. 23 | 20 | 89.29 | 96.88 | 350 | 260 |
| + | Prep. Ex. 24 | 20 | 85.71 | 93.75 | 450 | 320 |
| + | Prep. Ex. 25 | 20 | 78.57 | 89.06 | 450 | 320 |
| + | Prep. Ex. 17 | 20 | 53.57 | 84.38 | 525 | 500 |

TABLE 4-continued

| Experimental Groups | | Unit dose of drug sample (mg/kg) | Values of analyzed items (Percentage to normal group supplied with saline solution without TNBS treatment, %) | | | |
|---|---|---|---|---|---|---|
| Presence of TNBS treatment | Drug sample for administration | | Body weight | Colon length | Macroscopic score | MPO activity |
| + | Prep. Ex. 26 | 20 | 64.86 | 57.41 | 480 | 550 |
| + | Mesalazine ® | 10 | 59.46 | 89.06 | 420 | 360 |
| + | Mesalazine ® | 20 | 78.38 | 90.63 | 420 | 360 |
| + | Mesalazine ® | 50 | 75.68 | 90.63 | 450 | 390 |

Additionally, Table 5 below lists the summary of the results of the fraction-based experiments of model animals with acute colitis induced by TNBS. In the following Table 5, the values of analyzed item are represented as a percentage to the value of the normal group supplied with saline solution instead of the specific drug sample in the model animals not treated with TNBS.

As listed in the following Table 5, the administration of the combined extract, which was prepared by mixing the butanol-soluble fraction of the ethanol extract of *Anemarrhena asphodeloides* Bunge and the butanol-soluble fraction of the ethanol extract of *Coptis chinensis*, exhibited an improved anti-colitis effect in animal models with acute colitis induced by TNBS, compared with when the butanol-soluble fraction of the ethanol extract of *Anemarrhena asphodeloides* Bunge or the butanol-soluble fraction of the ethanol extract of *Coptis chinensis* was administered alone. Additionally, the anti-colitis effect of the combined extracts prepared by mixing the butanol-soluble fraction of the ethanol extract of *Anemarrhena asphodeloides* Bunge and the butanol-soluble fraction of the ethanol extract of *Coptis chinensis* was most significantly increased when the weight ratio between the butanol-soluble fraction of the ethanol extract of *Anemarrhena asphodeloides* Bunge and the butanol-soluble fraction of the ethanol extract of *Coptis chinensis* was 3:1, followed by 5:1 and 1:1, in this order. Additionally, based on the same amount of administration, the combined extract, which was prepared by mixing the butanol-soluble fraction of the ethanol extract of *Anemarrhena asphodeloides* Bunge and the butanol-soluble fraction of the ethanol extract of *Coptis chinensis*, exhibited a higher anti-colitis effect than Mesalazine®, which is currently used as a therapeutic drug for colitis.

TABLE 5

| Experimental Groups | | Unit dose of drug sample (mg/kg) | Values of analyzed items (Percentage to normal group supplied with saline solution without TNBS treatment, %) | | | |
|---|---|---|---|---|---|---|
| Presence of TNBS treatment | Drug sample for administration | | Body weight | Colon length | Macroscopic score | MPO activity |
| − | vehicle | — | 100 | 100 | 100 | 100 |
| + | vehicle | — | −100 | 74.6 | 1233 | 1020 |
| + | Prep. Ex. 16 | 20 | 66.67 | 87.3 | 667 | 410 |
| + | Prep. Ex. 27 | 20 | 67.86 | 89.48 | 597 | 340 |
| + | Prep. Ex. 28 | 20 | 96.3 | 93.65 | 533 | 233 |
| + | Prep. Ex. 29 | 20 | 93.65 | 96.83 | 400 | 200 |
| + | Prep. Ex. 30 | 20 | 85.19 | 95.24 | 500 | 250 |
| + | Prep. Ex. 31 | 20 | 70.37 | 88.89 | 567 | 283 |
| + | Prep. Ex. 32 | 20 | 66.67 | 88.89 | 633 | 300 |
| + | Prep. Ex. 19 | 20 | 70.37 | 85.71 | 700 | 383 |
| + | Mesalazine ® | 10 | 59.46 | 90.48 | 500 | 300 |
| + | Mesalazine ® | 20 | 78.38 | 92.06 | 500 | 300 |
| + | Mesalazine ® | 50 | 75.68 | 92.06 | 600 | 317 |

(4) Analysis of Effects on Expression of Inflammatory Marker Substances 100 mg of colon tissues of the experimental animals were homogenized after adding 250 μL of RIPA buffer including a protease inhibitor cocktail thereto. Then, the homogenized colon tissues were centrifuged at 4° C. at a rate of 13000 rpm for 15 minutes to obtain a supernatant. While storing the supernatant at −80° C., the expression amount of IL-6 and TNF-α, which correspond to proinflammatory cytokines, and the expression amount of IL-10, which corresponds to an anti-inflammatory cytokine, were measured using a 96-well ELISA plate kit (Pierce Biotechology, Inc., Rockford, Ill., USA). The following Table 6 lists the summary of the analysis results of inflammatory marker substances in extract-based experiments of model animals with acute colitis induced by TNBS.

TABLE 6

| Experimental Groups | | Unit dose of drug sample (mg/kg) | Conc. of inflammatory marker substances in colon tissues (pg/mg) | | |
|---|---|---|---|---|---|
| Presence of TNBS treatment | Drug sample for administration | | TNF-α | IL-6 | IL-10 |
| − | vehicle | — | 13.3 | 20.9 | 17.3 |
| + | vehicle | — | 102.7 | 83.6 | 7.3 |
| + | Prep. Ex. 14 | 20 | 49.4 | 32.8 | 11.3 |
| + | Prep. Ex. 21 | 20 | 33.3 | 25.3 | 16.3 |

TABLE 6-continued

| | | Unit dose | Conc. of inflammatory marker substances in colon tissues (pg/mg) | | |
|---|---|---|---|---|---|
| Presence of TNBS treatment | Drug sample for administration | of drug sample (mg/kg) | TNF-α | IL-6 | IL-10 |
| + | Prep. Ex. 22 | 20 | 27.3 | 17.9 | 18.3 |
| + | Prep. Ex. 23 | 20 | 37.7 | 24.3 | 15.2 |
| + | Prep. Ex. 24 | 20 | 47.91 | 28.3 | 13.2 |
| + | Prep. Ex. 25 | 20 | 45.1 | 27.6 | 10.7 |
| + | Prep. Ex. 17 | 20 | 53.3 | 43.3 | 10.3 |
| + | Mesalazine ® | 50 | 42.5 | 38.2 | 10.9 |

Additionally, the following Table 7 lists the summary of the analysis results of inflammatory marker substances in extract-based experiments of model animals with acute colitis induced by TNBS.

TABLE 7

| | Experimental Groups | | Conc. of inflammatory marker substances in colon tissues (pg/mg) | | |
|---|---|---|---|---|---|
| Presence of TNBS treatment | Drug sample for administration | Unit dose of drug sample (mg/kg) | TNF-α | IL-6 | IL-10 |
| − | vehicle | — | 14.8 | 23.5 | 17.5 |
| + | vehicle | — | 92.5 | 85.5 | 7.5 |
| + | Prep. Ex. 16 | 20 | 38.5 | 28.3 | 10.1 |
| + | Prep. Ex. 28 | 20 | 32.5 | 25.7 | 11.7 |
| + | Prep. Ex. 29 | 20 | 28.4 | 23.8 | 14.6 |
| + | Prep. Ex. 30 | 20 | 29.4 | 23.6 | 11.9 |
| + | Prep. Ex. 31 | 20 | 32.7 | 24.5 | 10.2 |
| + | Prep. Ex. 32 | 20 | 38.1 | 26.4 | 9.7 |
| + | Prep. Ex. 19 | 20 | 40.8 | 29.8 | 10.7 |
| + | Mesalazine ® | 50 | 42.5 | 38.2 | 10.9 |

III. Preparation of Pharmaceutical Compositions and Food Compositions

14. Preparation of Pharmaceutical Compositions.

In the following preparations of pharmaceutical compositions, the combined extract of Preparation Example 13 may be substituted with the combined extracts of Preparation Examples 20 to 32.

<14-1> Preparation of powders.

| the combined extract of Preparation Example 13 | 2 g |
|---|---|
| lactose | 1 g |

The above ingredients were mixed and then filled into an airtight container to prepare powders.

<14-2> Preparation of tablets.

| the combined extract of Preparation Example 13 | 100 mg |
|---|---|
| corn starch | 100 mg |
| lactose | 100 mg |
| magnesium stearate | 2 mg |

The above ingredients were mixed and then subjected to a tableting process according to a conventional tablet-manufacturing method to prepare tablets.

<14-3> Preparation of capsules.

| the combined extract of Preparation Example 13 | 100 mg |
|---|---|
| corn starch | 100 mg |
| lactose | 100 mg |
| magnesium stearate | 2 mg |

The above ingredients were mixed and then filled into gelatin capsules according to a conventional capsule-manufacturing method to prepare capsules.

<14-4> Preparation of pills.

| the combined extract of Preparation Example 13 | 1 g |
|---|---|
| lactose | 1.5 g |
| glycerin | 1 g |
| xylitol | 0.5 g |

The above ingredients were mixed and prepared into pills so that each pill can include 4 g.

<14-5> Preparation of granules.

| the combined extract of Preparation Example 13 | 150 mg |
|---|---|
| soybean extract | 50 mg |
| glucose | 200 mg |
| starch | 600 mg |

The above ingredients were mixed and then added with 100 mg of 30% ethanol, and the mixture was dried at 60° C. to prepare granules. The thus-prepared granules were filled into bags.

<14-6> Preparation of injections.

| the combined extract of Preparation Example 13 | 100 mg |
|---|---|
| sodium meta bisulfite | 3.0 mg |
| methylparaben | 0.8 mg |
| propylparaben | 0.1 mg |
| sterile distilled water for injection | adequate amount |

The above ingredients were mixed, and filled into ampoules (2 mL/ampoule), and the thus-prepared ampoules were sterilized to prepare injections.

15. Preparation of Food Compositions.

In the following preparations of food compositions, the combined extract of Preparation Example 13 may be substituted with the combined extracts of Preparation Examples 20 to 32.

<15-1> Preparation of Wheat Flour Foods.

The *Anemarrhena asphodeloides* Bunge extract obtained in Preparation Example 13, in the amount of 0.5 part by weight to 5.0 parts by weight, was added to 100 parts by weight of wheat flour, and prepared into breads, cakes, cookies, crackers, and noodles.

<15-2> Preparation of Soups and Gravies.

The *Anemarrhena asphodeloides* Bunge extract obtained in Preparation Example 13, in the amount of 0.1 part by weight to 5.0 parts by weight, was added to soups and gravies to prepare meat-processed products, soups and gravies for noodles and for health promotion.

<15-3> Preparation of Ground Beef.

The combined extract obtained in Preparation Example 13, in the amount of 10 parts by weight, was added to 100 parts by weight of ground beef to prepare ground beef for health promotion.

<15-4> Preparation of Dairy Products.

The combined extract obtained in Preparation Example 13, in the amount of 5 parts by weight to 10 parts by weight, was added to 100 parts by weight of milk, and the thus-obtained milk was used to prepare various dairy products, such as butter and ice cream.

<15-5> Preparation of Dry Cereals.

Brown rice, barley, glutinous rice, and adlay were dried by pregelatinizing them according to a known method and roasted. Then, the mixture was prepared into particles with 60 mesh using a grinder.

Black beans, black sesame, and perilla were steamed by a known method, dried, and then, roasted. Then, the mixture was prepared into particles with 60 mesh using a grinder.

The thus-prepared grains, seeds nuts, and the *Anemarrhena asphodeloides* Bunge extract of Preparation Example 13 were mixed at ratios exhibited below:

Grains (30 parts by weight of brown rice, 15 parts by weight of adlay, and 20 parts by weight of barley)

Seeds nuts (7 parts by weight of perilla, 8 parts by weight of black beans, and 7 parts by weight of black sesame)

*Anemarrhena asphodeloides* Bunge extract of Preparation Example 13 (3 parts by weight)

Lingzhi mushroom (0.5 part by weight)

Rehmannia (0.5 part by weight)

<15-6> Preparation of Health Drinks.

The minor ingredients, such as high fructose corn syrup (0.5 g), oligosaccharide (2 g), sugar (2 g), table salt (0.5 g), and water (75 g) were homogeneously combined with 5 g of the *Anemarrhena asphodeloides* Bunge extract of Preparation Example 13, and the resulting mixture was instantly sterilized. Then, the sterilized mixture was packaged in small containers, such as glass bottles and plastic bottles.

<15-7> Preparation of Vegetable Juices.

5 g of the *Anemarrhena asphodeloides* Bunge extract of Preparation Example 13 was added to 1,000 mL of tomato or carrot juice to prepare vegetable juices.

<15-8> Preparation of Fruit Juices.

1 g of the *Anemarrhena asphodeloides* Bunge extract of Preparation Example 13 was added to 1,000 mL of apple or grape juice to prepare fruit juices.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A method for preventing or treating colitis, comprising:
administering to a subject in need thereof an effective amount of a pharmaceutical composition comprising a combined extract,
wherein the combined extract consists of an *Anemarrhena asphodeloides* Bunge extract, and one or more selected from a *Rhizoma Coptidis* extract and a C3 to C8-alcohol-soluble fraction of the *Rhizoma Coptidis* extract,
wherein the extraction solvent for the *Anemarrhena asphodeloides* Bunge extract is selected from water, methanol, ethanol, a mixture of water and methanol, and a mixture of water and ethanol; and
wherein the extraction solvent for the *Rhizoma Coptidis* extract is selected from water, methanol, ethanol, a mixture of water and methanol, and a mixture of water and ethanol; and
wherein the alcohol-soluble fraction of the *Rhizoma Coptidis* extract is obtained by suspending the *Rhizoma Coptidis* extract by adding water thereto followed by fractionation after adding an alcohol having a carbon number of 3 to 8 thereto.

2. The method of claim 1, wherein the weight ratio between the *Anemarrhena asphodeloides* Bunge extract; and the one or more selected from a *Rhizoma Coptidis* extract and a C3 to C8-alcohol-soluble fraction of the *Rhizoma Coptidis* extract is in the range of from 10:1 to 1:10.

3. The method of claim 1, wherein the colitis is an inflammatory bowel disease or an irritable bowel syndrome.

4. The method of claim 1, wherein the *Anemarrhena asphodeloides* Bunge extract comprises mangiferin or neomangiferin.

5. The method of claim 1, wherein the *Rhizoma Coptidis* is *Coptis chinensis*.

6. The method of claim 1, wherein the alcohol-soluble fraction of the *Rhizoma Coptidis* extract is a butanol-soluble fraction of the *Rhizoma Coptidis* extract.

7. The method of claim 1, wherein the *Rhizoma Coptidis* extract or the alcohol-soluble fraction of the *Rhizoma Coptidis* extract comprises berberine.

8. The method of claim 1, wherein the composition comprises an *Anemarrhena asphodeloides* Bunge extract and a *Rhizoma Coptidis* extract, and the weight ratio between the *Anemarrhena asphodeloides* Bunge extract and the *Rhizoma Coptidis* extract is in the range of from 1:1 to 5:1.

9. The method of claim 1, wherein the composition comprises an *Anemarrhena asphodeloides* Bunge extract and a C3 to C8-alcohol-soluble fraction of the *Rhizoma Coptidis* extract, and the weight ratio between the *Anemarrhena asphodeloides* Bunge extract and the alcohol-soluble fraction of the *Rhizoma Coptidis* extract is in the range of from 1:1 to 5:1.

10. A method for preventing or improving colitis, comprising:
administering to a subject in need thereof an effective amount of a food composition comprising a combined extract,
wherein the combined extract consists of an *Anemarrhena asphodeloides* Bunge extract; and one or more selected from a *Rhizoma Coptidis* extract and a C3 to C8-alcohol-soluble fraction of the *Rhizoma Coptidis* extract,
wherein the extraction solvent for the *Anemarrhena asphodeloides* Bunge extract is selected from water, methanol, ethanol, a mixture of water and methanol, and a mixture of water and ethanol; and
wherein the extraction solvent for the *Rhizoma Coptidis* extract is selected from water, methanol, ethanol, a mixture of water and methanol, and a mixture of water and ethanol; and
wherein the alcohol-soluble fraction of the *Rhizoma Coptidis* extract is obtained by suspending the *Rhizoma Coptidis* extract by adding water thereto followed by fractionation after adding an alcohol having a carbon number of 3 to 8 thereto.

11. The method of claim 10, wherein the weight ratio between the *Anemarrhena asphodeloides* Bunge extract; and the one or more selected from a *Rhizoma Coptidis* extract and a C3 to C8-alcohol-soluble fraction of the *Rhizoma Coptidis* extract is in the range of from 10:1 to 1:10.

12. The method of claim 10, wherein the colitis is an inflammatory bowel disease or an irritable bowel syndrome.

13. The method of claim 10, wherein the *Anemarrhena asphodeloides* Bunge extract comprises mangiferin or neomangiferin.

14. The method of claim 10, wherein the *Rhizoma Coptidis* is *Coptis chinensis*.

15. The method of claim 10, wherein the alcohol-soluble fraction of the *Rhizoma Coptidis* extract is a butanol-soluble fraction of the *Rhizoma Coptidis* extract.

16. The method of claim 10, wherein the *Rhizoma Coptidis* extract or the alcohol-soluble fraction of the *Rhizoma Coptidis* extract comprises berberine.

17. The method of claim 10, wherein the composition comprises an *Anemarrhena asphodeloides* Bunge extract and a *Rhizoma Coptidis* extract, and the weight ratio between the *Anemarrhena asphodeloides* Bunge extract and the *Rhizoma Coptidis* extract is in the range of from 1:1 to 5:1.

18. The method of claim 10, wherein the composition comprises an *Anemarrhena asphodeloides* Bunge extract and a C3 to C8-alcohol-soluble fraction of the *Rhizoma Coptidis* extract, and the weight ratio between the *Anemarrhena asphodeloides* Bunge extract and the alcohol-soluble fraction of the *Rhizoma Coptidis* extract is in the range of from 1:1 to 5:1.

* * * * *